US012642936B2

(12) United States Patent
Holyoake et al.

(10) Patent No.: US 12,642,936 B2
(45) Date of Patent: Jun. 2, 2026

(54) COLLAPSIBLE CONDUIT, PATIENT INTERFACE AND HEADGEAR CONNECTOR

(71) Applicant: Fisher & Paykel Healthcare Limited, Auckland (NZ)

(72) Inventors: Bruce Gordon Holyoake, Auckland (NZ); German Klink, Auckland (NZ); Alicia Jerram Hunter Evans, Auckland (NZ); Craig Karl White, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 744 days.

(21) Appl. No.: 17/707,800

(22) Filed: Mar. 29, 2022

(65) Prior Publication Data

US 2022/0323708 A1 Oct. 13, 2022

Related U.S. Application Data

(63) Continuation of application No. 16/324,277, filed as application No. PCT/IB2017/054896 on Aug. 11, 2017, now Pat. No. 11,324,908.

(Continued)

(51) Int. Cl.
*A61M 16/06* (2006.01)
*A61M 16/01* (2006.01)
(Continued)

(52) U.S. Cl.
CPC ........ *A61M 16/0683* (2013.01); *A61M 16/01* (2013.01); *A61M 16/0666* (2013.01);
(Continued)

(58) Field of Classification Search
CPC ......... A61B 5/01; A61B 5/0205; A61B 5/038; A61B 5/082; A61B 5/083; A61B 5/0836;
(Continued)

(56) References Cited

U.S. PATENT DOCUMENTS

| | | | |
|---|---|---|---|
| 27,846 A | 4/1860 | Underwood |
| 207,626 A | 9/1878 | Sargent |

(Continued)

FOREIGN PATENT DOCUMENTS

| | | |
|---|---|---|
| AU | 2528471 A | 8/1972 |
| AU | 479953 B | 5/1973 |

(Continued)

OTHER PUBLICATIONS

Optiflow™ + Nasal Cannula Interface, posted at fphcare.com, earliest date available on Jun. 24, 2018, [online], acquired on uNov. 18, 2021, Available on internet. url:https://www.fphcare.com/us/hospital/adult-respiratory/optiflow/optiflow-plus-nasal-cannula/ (Year:2018).

(Continued)

*Primary Examiner* — Annette Dixon
(74) *Attorney, Agent, or Firm* — Knobbe, Martens, Olson & Bear, LLP

(57) ABSTRACT

A conduit with a collapsible portion, and a nasal Interface for providing a flow of gases to a user, is described. The interface comprises a manifold and at least one nasal prong or an outlet extending from the manifold to be received by a user's nare. A side member extends from each side of the manifold, each side member comprising a collapsible portion comprising a lumen. In an open configuration the lumen remains open and in a closed configuration the collapsible portion is pinched or flattened to occlude or substantially occlude the lumen. At least one of the side members is a conduit for a flow of gases from an Inlet of the patient interface to the manifold.

18 Claims, 29 Drawing Sheets

Related U.S. Application Data

(60) Provisional application No. 62/431,608, filed on Dec. 8, 2016, provisional application No. 62/399,893, filed on Sep. 26, 2016, provisional application No. 62/373,561, filed on Aug. 11, 2016.

(51) Int. Cl.

| | |
|---|---|
| *A61M 16/08* | (2006.01) |
| *A61M 16/16* | (2006.01) |
| *A61M 16/12* | (2006.01) |

(52) U.S. Cl.
CPC .... *A61M 16/0672* (2014.02); *A61M 16/0875* (2013.01); *A61M 16/16* (2013.01); *A61M 16/12* (2013.01); *A61M 2202/0208* (2013.01); *A61M 2202/0225* (2013.01); *A61M 2202/0266* (2013.01); *A61M 2202/0275* (2013.01); *A61M 2202/0283* (2013.01); *A61M 2202/0291* (2013.01); *A61M 2205/0216* (2013.01); *A61M 2205/3303* (2013.01); *A61M 2209/088* (2013.01); *A61M 2210/0662* (2013.01); *A61M 2230/205* (2013.01); *A61M 2230/432* (2013.01)

(58) Field of Classification Search
CPC ......... A61B 5/085; A61B 5/087; A61B 5/097; A61B 5/14542; A61B 5/14551; A61B 5/411; A61B 5/4806; A61B 5/4818; A61B 5/6819; A61B 5/682; A61B 5/6833; A61B 7/003; A61J 17/001; A61J 7/0053; A61K 33/00; A61K 9/0073; A61M 11/005; A61M 15/00; A61M 15/08; A61M 16/00; A61M 16/0003; A61M 16/0006; A61M 16/0051; A61M 16/0057; A61M 16/0063; A61M 16/0066; A61M 16/0069; A61M 16/0078; A61M 16/009; A61M 16/0093; A61M 16/01; A61M 16/021; A61M 16/022; A61M 16/024; A61M 16/0415; A61M 16/045; A61M 16/0488; A61M 16/049; A61M 16/06; A61M 16/0605; A61M 16/0611; A61M 16/0616; A61M 16/0622; A61M 16/0627; A61M 16/0633; A61M 16/065; A61M 16/0655; A61M 16/0666; A61M 16/0672; A61M 16/0677; A61M 16/0683; A61M 16/0688; A61M 16/0694; A61M 16/08; A61M 16/0808; A61M 16/0816; A61M 16/0825; A61M 16/0833; A61M 16/0841; A61M 16/085; A61M 16/0858; A61M 16/0866; A61M 16/0875; A61M 16/0883; A61M 16/10; A61M 16/1005; A61M 16/101; A61M 16/104; A61M 16/1045; A61M 16/1055; A61M 16/106; A61M 16/1065; A61M 16/107; A61M 16/1075; A61M 16/108; A61M 16/1085; A61M 16/109; A61M 16/1095; A61M 16/12; A61M 16/122; A61M 16/125; A61M 16/127; A61M 16/14; A61M 16/16; A61M 16/161; A61M 16/20; A61M 16/201; A61M 16/204; A61M 16/205; A61M 16/207; A61M 16/208; A61M 16/209; A61M 16/22; A61M 2016/0021; A61M 2016/0024; A61M 2016/0027; A61M 2016/003; A61M 2016/0033; A61M 2016/0036; A61M 2016/0039; A61M 2016/0661; A61M 2016/1025; A61M 2016/103; A61M 2021/0088; A61M 2025/0226; A61M 21/00; A61M 2202/0007; A61M 2202/0085; A61M 2202/0208; A61M 2202/0225; A61M 2202/0275; A61M 2202/0283; A61M 2202/03; A61M 2202/203; A61M 2202/206; A61M 2205/02; A61M 2205/0205; A61M 2205/0216; A61M 2205/0238; A61M 2205/0266; A61M 2205/075; A61M 2205/18; A61M 2205/273; A61M 2205/33; A61M 2205/3327; A61M 2205/3331; A61M 2205/3334; A61M 2205/3348; A61M 2205/3368; A61M 2205/3372; A61M 2205/3382; A61M 2205/3386; A61M 2205/3393; A61M 2205/3553; A61M 2205/3584; A61M 2205/3592; A61M 2205/36; A61M 2205/3633; A61M 2205/3653; A61M 2205/42; A61M 2205/50; A61M 2205/502; A61M 2205/52; A61M 2205/581; A61M 2205/583; A61M 2205/588; A61M 2205/59; A61M 2205/6045; A61M 2205/7509; A61M 2205/7518; A61M 2205/7527; A61M 2205/7545; A61M 2205/7554; A61M 2205/7563; A61M 2205/8206; A61M 2205/8225; A61M 2206/10; A61M 2206/14; A61M 2206/20; A61M 2207/00; A61M 2209/06; A61M 2209/082; A61M 2209/084; A61M 2209/088; A61M 2210/0618; A61M 2210/0625; A61M 2210/0662; A61M 2230/005; A61M 2230/06; A61M 2230/205; A61M 2230/30; A61M 2230/40; A61M 2230/42; A61M 2230/43; A61M 2230/432; A61M 2230/435; A61M 2230/60; A61M 2240/00; A61M 25/02; A61M 39/08; A62B 18/02; A62B 18/025; A62B 18/084; A62B 7/00; A63B 2024/0093; A63B 21/0085; A63B 23/18; B01D 2259/4533; B01D 2259/4541; B01D 53/00; B01D 53/34; B29C 45/00; B29C 64/112; B33Y 10/00; B33Y 30/00; C01B 21/24; F16K 17/02; F16K 31/084; F16L 11/111; G01N 33/497; H01H 3/48; Y02C 20/10; Y10S 128/26; Y10S 128/91; Y10S 128/912; Y10S 200/02; Y10T 137/3006; Y10T 137/309; Y10T 29/49826

See application file for complete search history.

(56) References Cited

U.S. PATENT DOCUMENTS

| | | | |
|---|---|---|---|
| 260,959 | A | 7/1882 | Emery |
| 286,561 | A | 10/1883 | Smith et al. |
| 396,528 | A | 1/1889 | Blake |
| 402,632 | A | 5/1889 | Traves |
| 495,439 | A | 4/1893 | Thacher |
| 509,409 | A | 11/1893 | Totten |
| 531,766 | A | 1/1895 | Block |
| 538,895 | A | 5/1895 | Casgrain |
| 540,255 | A | 6/1895 | Hirsch |
| 543,125 | A | 7/1895 | Brown |
| 553,000 | A | 1/1896 | Hunt |
| 584,501 | A | 6/1897 | Gates |
| 596,341 | A | 12/1897 | Seymour |
| 613,979 | A | 11/1898 | Eaglesfield |
| 614,676 | A | 11/1898 | Tucker |
| 639,193 | A | 12/1899 | Alliger |

(56)                References Cited

U.S. PATENT DOCUMENTS

| | | | |
|---|---|---|---|
| 642,549 A | 1/1900 | Kennedy |
| 727,385 A | 5/1903 | Kops |
| 733,852 A | 7/1903 | Lee |
| 827,243 A | 7/1906 | Larson |
| 829,677 A | 8/1906 | Sillamn |
| 897,955 A | 9/1908 | Barrett et al. |
| 899,670 A | 9/1908 | Hyde, Jr. |
| 906,215 A | 12/1908 | Gammeter |
| 939,726 A | 11/1909 | Magdiel |
| 973,242 A | 10/1910 | Wayson, Jr. |
| 1,125,542 A | 1/1915 | Humphries |
| 1,146,111 A | 7/1915 | Styl |
| 1,156,385 A | 10/1915 | Willson, Jr. |
| 1,364,513 A | 1/1921 | Ono |
| 1,431,052 A | 10/1922 | Shukie |
| 1,471,360 A | 10/1923 | Sangren |
| 1,471,726 A | 10/1923 | Ginty |
| 1,479,900 A | 1/1924 | Dorner et al. |
| 1,560,889 A | 11/1925 | Wearham |
| 1,705,115 A | 3/1929 | Hollestelle |
| 1,706,314 A | 3/1929 | Norris |
| 1,722,599 A | 7/1929 | Test et al. |
| 1,805,442 A | 5/1931 | Wallfisch |
| 1,806,586 A | 5/1931 | Christmas |
| 1,824,759 A | 9/1931 | Bainbridge |
| 1,894,467 A | 1/1933 | Heinrich |
| 1,918,998 A | 7/1933 | Wells |
| 1,945,617 A | 2/1934 | Nelson |
| 1,970,137 A | 8/1934 | Harte |
| 1,998,560 A | 4/1935 | Smith |
| 2,013,242 A | 9/1935 | Stinson |
| 2,073,471 A | 3/1937 | Franz |
| 2,111,053 A | 3/1938 | Olsen |
| 2,116,488 A | 5/1938 | Jackson |
| 2,116,490 A | 5/1938 | Arthur |
| 2,157,061 A | 5/1939 | Ernst |
| 2,169,968 A | 8/1939 | Clifford |
| 2,176,735 A | 10/1939 | Freedlander et al. |
| 2,220,453 A | 11/1940 | Lowres |
| 2,234,265 A | 3/1941 | Lowres |
| 2,236,304 A | 3/1941 | Snavely |
| 2,241,814 A | 5/1941 | Hansen |
| 2,267,051 A | 12/1941 | Stevens |
| 2,277,981 A | 3/1942 | Horton |
| 2,284,848 A | 6/1942 | Ryan |
| 2,287,409 A | 6/1942 | Samuel |
| 2,310,622 A | 2/1943 | Ray |
| 2,314,814 A | 3/1943 | Bruce |
| 2,338,145 A | 1/1944 | Webb |
| 2,348,277 A | 5/1944 | Boothyby et al. |
| 2,377,970 A | 6/1945 | Rives |
| 2,400,077 A | 5/1946 | Dauster |
| 2,514,432 A | 7/1950 | Whitford |
| 2,529,301 A | 11/1950 | Lykken |
| 2,533,271 A | 12/1950 | Livermon |
| 2,564,326 A | 8/1951 | Dray |
| 2,567,150 A | 9/1951 | Frazier et al. |
| 2,576,154 A | 11/1951 | Trautvetter |
| 2,589,439 A | 3/1952 | Seidel |
| 2,601,083 A | 6/1952 | Brouse |
| 2,609,699 A | 9/1952 | Rohn |
| 2,620,513 A | 12/1952 | Cryor et al. |
| 2,643,380 A | 6/1953 | David |
| 2,661,503 A | 12/1953 | Longstreet |
| 2,669,127 A | 2/1954 | Raser, Jr. |
| 2,687,333 A | 8/1954 | Kostolnik |
| 2,690,591 A | 10/1954 | Wallace |
| 2,709,371 A | 5/1955 | Hale |
| 2,718,255 A | 9/1955 | Samuel |
| 2,735,432 A | 2/1956 | Hudson |
| 2,738,688 A | 3/1956 | Eaton |
| 2,801,547 A | 8/1957 | Guibert |
| 2,811,967 A | 11/1957 | Stampe |
| 2,819,780 A | 1/1958 | Fallon et al. |
| 2,831,487 A | 4/1958 | Tafilaw |

| | | | |
|---|---|---|---|
| 2,868,199 A | 1/1959 | Hudson |
| 2,931,277 A | 4/1960 | La Bombard |
| 2,943,775 A | 7/1960 | Mack et al. |
| 2,969,081 A | 1/1961 | Pipes |
| 2,986,276 A | 5/1961 | Perine |
| 2,998,818 A | 9/1961 | Tabor et al. |
| 3,002,304 A | 10/1961 | Drese et al. |
| 3,004,535 A | 10/1961 | Nielson |
| 3,095,876 A | 7/1963 | Neal |
| 3,096,279 A | 7/1963 | Komline |
| 3,101,029 A | 8/1963 | Johnston et al. |
| 3,197,201 A | 7/1965 | Craig |
| 3,208,505 A | 9/1965 | Craemer |
| 3,234,806 A | 2/1966 | Albrecht et al. |
| 3,245,276 A | 4/1966 | Daon |
| 3,263,292 A | 8/1966 | Fekete |
| 3,362,403 A | 1/1968 | Fleming et al. |
| 3,365,966 A | 1/1968 | Heyer |
| 3,365,967 A | 1/1968 | Moogk |
| 3,377,712 A | 4/1968 | Farkas et al. |
| 3,429,761 A | 2/1969 | Bleher |
| 3,446,880 A | 5/1969 | Enicks |
| 3,513,844 A | 5/1970 | Smith |
| 3,542,116 A | 11/1970 | Machlin |
| 3,563,166 A | 2/1971 | Bajak et al. |
| 3,576,138 A | 4/1971 | Wildhagen |
| 3,585,639 A | 6/1971 | Enicks |
| 3,603,384 A | 9/1971 | Huggins et al. |
| 3,616,818 A | 11/1971 | Case et al. |
| 3,623,377 A | 11/1971 | Lewis et al. |
| 3,632,932 A | 1/1972 | Beaudoin et al. |
| 3,640,143 A | 2/1972 | Krohn-Holm |
| 3,654,640 A | 4/1972 | Katzman |
| 3,656,359 A | 4/1972 | Dorf et al. |
| 3,677,801 A | 7/1972 | Hardy |
| 3,679,214 A | 7/1972 | Boyte |
| 3,682,171 A * | 8/1972 | Dali .................. A61M 16/0672 |
| | | 128/207.18 |
| 3,695,264 A | 10/1972 | Laeral |
| 3,718,137 A | 2/1973 | Gaylord |
| 3,734,270 A | 5/1973 | Foody |
| 3,754,552 A | 8/1973 | King |
| 3,783,705 A | 1/1974 | Moogk |
| 3,799,164 A | 3/1974 | Rollins |
| 3,802,824 A | 4/1974 | Amster et al. |
| 3,834,439 A | 9/1974 | Mirtain |
| 3,839,738 A | 10/1974 | Coslett |
| 3,857,295 A | 12/1974 | Hall et al. |
| 3,858,615 A | 1/1975 | Weigl |
| 3,869,933 A | 3/1975 | Dorf |
| 3,894,900 A | 7/1975 | Redmond, Jr. |
| 3,910,025 A | 10/1975 | Takai |
| 3,915,075 A | 10/1975 | Luke et al. |
| 3,941,637 A | 3/1976 | Masuda et al. |
| 3,944,432 A | 3/1976 | Brinkmann et al. |
| 3,957,282 A | 5/1976 | Finnigan |
| 3,964,328 A | 6/1976 | Redmond, Jr. |
| 3,968,701 A | 7/1976 | Maruyama |
| 4,007,644 A | 2/1977 | Weinberger |
| 4,019,399 A | 4/1977 | Waugh |
| 4,030,300 A | 6/1977 | Thompson |
| 4,033,360 A | 7/1977 | Nienow et al. |
| 4,049,300 A | 9/1977 | Schneider |
| 4,051,741 A | 10/1977 | Marczewski |
| 4,079,633 A | 3/1978 | Cheema et al. |
| 4,106,505 A * | 8/1978 | Salter ............... A61M 16/0672 |
| | | 128/207.18 |
| 4,108,011 A | 8/1978 | Gregg et al. |
| 4,120,324 A | 10/1978 | Pahl |
| 4,147,069 A | 4/1979 | Derner |
| 4,168,024 A | 9/1979 | D'Alo |
| 4,196,760 A | 4/1980 | McDaniel et al. |
| 4,198,167 A | 4/1980 | Deal et al. |
| 4,201,205 A | 5/1980 | Bartholomew |
| 4,202,344 A | 5/1980 | Mills et al. |
| 4,241,775 A | 12/1980 | Jackson |
| 4,262,406 A | 4/1981 | Fredrickson et al. |
| 4,263,908 A | 4/1981 | Mizerak |
| 4,266,912 A | 5/1981 | Roman |

(56) References Cited

U.S. PATENT DOCUMENTS

| | | | |
|---|---|---|---|
| 4,270,888 A | 6/1981 | Kane et al. |
| 4,274,069 A | 6/1981 | Troebel et al. |
| 4,289,230 A | 9/1981 | McGee |
| 4,292,365 A | 9/1981 | Kane et al. |
| 4,330,287 A | 5/1982 | Fischer |
| 4,337,056 A | 6/1982 | Bruns |
| 4,355,741 A | 10/1982 | Kayss |
| 4,359,445 A | 11/1982 | Kane et al. |
| 4,367,067 A | 1/1983 | Chao |
| 4,377,162 A | 3/1983 | Staver |
| 4,409,995 A | 10/1983 | Nichols |
| 4,416,368 A | 11/1983 | Muramatsu et al. |
| 4,417,800 A | 11/1983 | Hirose et al. |
| 4,422,456 A | 12/1983 | Tiep |
| 4,427,226 A | 1/1984 | Shartzer |
| 4,449,959 A | 5/1984 | Matsumura |
| 4,465,067 A | 8/1984 | Koch et al. |
| 4,475,248 A | 10/1984 | L'Abbe et al. |
| 4,498,480 A | 2/1985 | Mortensen |
| 4,515,577 A | 5/1985 | Cathey et al. |
| 4,535,767 A | 8/1985 | Tiep et al. |
| 4,569,468 A | 2/1986 | Neer |
| 4,575,042 A | 3/1986 | Grimland et al. |
| 4,586,915 A | 5/1986 | Cathey et al. |
| 4,599,074 A | 7/1986 | Beckly |
| 4,603,442 A | 8/1986 | Barfield |
| 4,643,701 A | 2/1987 | Meyer et al. |
| 4,655,381 A | 4/1987 | Fontana |
| 4,674,994 A | 6/1987 | Tomiyori et al. |
| 4,706,683 A | 11/1987 | Chilton |
| 4,753,233 A | 6/1988 | Grimes |
| 4,786,274 A | 11/1988 | Robecchi et al. |
| 4,793,342 A | 12/1988 | Haber et al. |
| 4,809,640 A | 3/1989 | Pilley et al. |
| 4,810,153 A | 3/1989 | Armelin |
| 4,810,237 A | 3/1989 | Mantovaara |
| 4,824,502 A | 4/1989 | Nagayoshi et al. |
| 4,866,816 A | 9/1989 | Caveney |
| 4,873,100 A | 10/1989 | Dirksing et al. |
| 4,878,491 A | 11/1989 | McGilvray, III |
| 4,879,117 A | 11/1989 | Rombi |
| 4,885,127 A | 12/1989 | Yokoyama |
| 4,893,999 A | 1/1990 | Chmelir et al. |
| 4,915,105 A | 4/1990 | Lee |
| 4,944,442 A | 7/1990 | Buchko |
| 4,960,121 A | 10/1990 | Nelson et al. |
| 4,960,476 A | 10/1990 | White, Jr. et al. |
| 4,981,462 A | 1/1991 | White, Jr. et al. |
| 4,983,184 A | 1/1991 | Steinemann |
| 4,989,599 A * | 2/1991 | Carter ............... A61M 16/0666 |
| | | 128/207.18 |
| 4,993,998 A | 2/1991 | Tanaka et al. |
| 5,005,571 A | 4/1991 | Dietz |
| 5,007,462 A | 4/1991 | Kanao |
| 5,018,471 A | 5/1991 | Stevens |
| 5,023,023 A | 6/1991 | Elenewski |
| 5,030,174 A | 7/1991 | Eguchi |
| 5,046,993 A | 9/1991 | Macchiarulo et al. |
| 5,052,084 A | 10/1991 | Braun |
| 5,088,162 A | 2/1992 | Allan |
| 5,089,189 A | 2/1992 | Staneluis et al. |
| 5,121,916 A | 6/1992 | Sanchez |
| 5,138,666 A | 8/1992 | Bauer et al. |
| 5,145,188 A | 9/1992 | Bartelt et al. |
| 5,154,446 A | 10/1992 | Blake |
| 5,171,310 A | 12/1992 | Chisena |
| 5,176,249 A | 1/1993 | Esterson et al. |
| 5,192,178 A | 3/1993 | Silbernagel |
| 5,201,398 A | 4/1993 | Clugston |
| 5,214,986 A | 6/1993 | Roberts |
| 5,224,719 A | 7/1993 | Goodspeed |
| 5,237,986 A | 8/1993 | Seppala et al. |
| 5,254,049 A | 10/1993 | Gregg |
| 5,269,296 A | 12/1993 | Landis |
| 5,291,880 A | 3/1994 | Almqvist et al. |
| 5,348,000 A | 9/1994 | Teves |
| 5,349,949 A | 9/1994 | Schegerin |
| 5,355,184 A | 10/1994 | Varveris et al. |
| 5,373,980 A | 12/1994 | Rowell et al. |
| 5,390,373 A | 2/1995 | Flory |
| 5,400,776 A | 3/1995 | Bartholomew |
| 5,435,321 A | 7/1995 | McMillen et al. |
| 5,441,046 A | 8/1995 | Starr et al. |
| 5,444,750 A | 8/1995 | Stewart et al. |
| 5,457,891 A | 10/1995 | Taylor |
| 5,458,831 A | 10/1995 | Saeki et al. |
| 5,477,852 A | 12/1995 | Landis et al. |
| 5,485,850 A | 1/1996 | Dietz |
| 5,487,461 A | 1/1996 | Focke et al. |
| 5,488,948 A | 2/1996 | Dubruille et al. |
| 5,509,409 A | 4/1996 | Weatherholt |
| 5,510,721 A | 4/1996 | Walles et al. |
| 5,533,506 A | 7/1996 | Wood |
| 5,538,000 A | 7/1996 | Rudolph |
| 5,618,266 A | 4/1997 | Liprie |
| 5,618,267 A | 4/1997 | Palestrant |
| 5,632,837 A | 5/1997 | Carmien |
| 5,640,744 A | 6/1997 | Allan |
| 5,655,643 A | 8/1997 | Bonnet |
| 5,697,107 A | 12/1997 | Takimoto |
| 5,697,362 A | 12/1997 | Albrecht |
| 5,697,363 A | 12/1997 | Hart |
| 5,713,542 A | 2/1998 | Benoit |
| 5,722,218 A | 3/1998 | Lerner |
| 5,734,995 A | 4/1998 | Chiang |
| 5,762,373 A | 6/1998 | Sugimoto |
| 5,771,886 A | 6/1998 | Maire et al. |
| 5,792,018 A | 8/1998 | Winninger |
| 5,827,243 A | 10/1998 | Palestrant |
| 5,861,116 A | 1/1999 | Mandich |
| 5,868,639 A | 2/1999 | Hormann |
| 5,901,607 A | 5/1999 | Kimura |
| 5,911,369 A | 6/1999 | Yamazaki |
| 5,915,542 A | 6/1999 | Swiet |
| 5,924,546 A | 7/1999 | Funaya |
| 5,934,275 A | 8/1999 | Gazzara |
| 5,935,086 A | 8/1999 | Beacon et al. |
| 6,010,304 A | 1/2000 | Moniz et al. |
| 6,019,101 A | 2/2000 | Cotner et al. |
| 6,035,852 A | 3/2000 | Hoftman |
| 6,038,706 A | 3/2000 | Seiler |
| 6,044,844 A | 4/2000 | Kwok et al. |
| 6,050,916 A | 4/2000 | Hunkert |
| 6,065,756 A | 5/2000 | Eignor |
| 6,070,579 A | 6/2000 | Bryant et al. |
| 6,109,578 A | 8/2000 | Guthrie et al. |
| 6,116,637 A | 9/2000 | Takeuchi et al. |
| 6,123,071 A | 9/2000 | Berthon-jones et al. |
| 6,148,817 A | 11/2000 | Bryant et al. |
| 6,170,249 B1 | 1/2001 | Blase et al. |
| 6,196,090 B1 | 3/2001 | Dumont |
| 6,202,957 B1 | 3/2001 | Bannert et al. |
| 6,209,705 B1 | 4/2001 | Drewitz |
| 6,216,853 B1 | 4/2001 | Fujita |
| 6,244,621 B1 | 6/2001 | Kameyoshi et al. |
| 6,270,595 B1 | 8/2001 | Takayama et al. |
| 6,332,465 B1 | 12/2001 | Xue et al. |
| 6,341,383 B1 | 1/2002 | Beltrani |
| 6,346,800 B1 | 2/2002 | Mano et al. |
| 6,364,086 B1 | 4/2002 | Blaurock et al. |
| 6,367,732 B1 | 4/2002 | Bobren et al. |
| 6,390,915 B2 | 5/2002 | Brantley et al. |
| 6,402,194 B1 | 6/2002 | Takeuchi |
| 6,422,240 B1 | 7/2002 | Levitsky et al. |
| 6,431,172 B1 | 8/2002 | Bordewick |
| 6,443,507 B1 | 9/2002 | Korvemaker |
| 6,443,552 B1 | 9/2002 | Inoue et al. |
| 6,454,899 B1 | 9/2002 | Campbell et al. |
| 6,478,025 B1 | 11/2002 | Yort et al. |
| 6,478,026 B1 | 11/2002 | Wood |
| 6,484,871 B2 | 11/2002 | van Leeuwen |
| 6,485,384 B1 | 11/2002 | Ochiai et al. |
| 6,488,026 B2 | 12/2002 | Lauer |
| 6,527,474 B2 | 3/2003 | Nabeshima |

(56)                References Cited

U.S. PATENT DOCUMENTS

| | | | |
|---|---|---|---|
| 6,536,435 B1 | 3/2003 | Fecteau et al. | |
| 6,561,344 B1 | 5/2003 | Basse | |
| 6,571,797 B1 | 6/2003 | Magidson et al. | |
| 6,574,449 B2 | 6/2003 | Yoda et al. | |
| 6,580,894 B1 | 6/2003 | Kobashigawa | |
| 6,588,424 B2 | 7/2003 | Bardel | |
| 6,595,215 B2 | 7/2003 | Wood | |
| 6,597,888 B1 | 7/2003 | Abe et al. | |
| 6,631,253 B2 | 10/2003 | Nakafuji et al. | |
| 6,637,434 B2 | 10/2003 | Noble | |
| 6,652,691 B1 | 11/2003 | Yu et al. | |
| 6,669,712 B1 | 12/2003 | Cardoso | |
| 6,679,265 B2 | 1/2004 | Strickland et al. | |
| 6,684,882 B1 | 2/2004 | Morine | |
| 6,688,843 B2 | 2/2004 | Saeki | |
| 6,695,771 B2 | 2/2004 | Takada | |
| 6,709,552 B2 | 3/2004 | Sakuma et al. | |
| 6,745,770 B2 | 6/2004 | McAuliffe et al. | |
| 6,776,162 B2 | 8/2004 | Wood | |
| 6,776,163 B2 | 8/2004 | Dougill et al. | |
| 6,783,186 B1 | 8/2004 | McGanty | |
| 6,792,787 B1 | 9/2004 | Coalson | |
| 6,877,792 B2 | 4/2005 | Kanie et al. | |
| 6,886,564 B2 | 5/2005 | Sullivan et al. | |
| 6,938,806 B2 | 9/2005 | James | |
| 6,941,710 B2 | 9/2005 | Eden | |
| 6,962,101 B2 | 11/2005 | Granger | |
| 6,981,503 B1 | 1/2006 | Shapiro | |
| 6,999,732 B2 | 2/2006 | Fukuda | |
| 7,017,577 B2 | 3/2006 | Matich | |
| 7,036,503 B2 | 5/2006 | Miyazawa et al. | |
| 7,073,688 B2 | 7/2006 | Choi et al. | |
| 7,128,070 B2 | 10/2006 | Wiener et al. | |
| 7,132,120 B2 | 11/2006 | Okaizumi et al. | |
| 7,134,433 B2 | 11/2006 | Sato | |
| 7,146,898 B2 | 12/2006 | O'Dwyer | |
| 7,178,528 B2 | 2/2007 | Lau et al. | |
| 7,185,653 B2 | 3/2007 | Lee | |
| 7,190,915 B2 | 3/2007 | Akizuki et al. | |
| 7,201,169 B2 | 4/2007 | Wilkie et al. | |
| 7,225,811 B2 | 6/2007 | Ruiz et al. | |
| 7,242,895 B2 | 7/2007 | Inada et al. | |
| 7,243,649 B2 | 7/2007 | Moenning et al. | |
| 7,254,353 B2 | 8/2007 | Koyama et al. | |
| 7,255,107 B1 | 8/2007 | Gomez | |
| 7,257,341 B2 | 8/2007 | Hanamoto et al. | |
| 7,260,337 B2 | 8/2007 | Koyama et al. | |
| 7,261,105 B2 | 8/2007 | Fukunaga et al. | |
| 7,275,541 B2 | 10/2007 | Fukunaga et al. | |
| 7,277,651 B2 | 10/2007 | Hanamoto et al. | |
| 7,283,763 B2 | 10/2007 | Akizuki et al. | |
| 7,305,988 B2 | 12/2007 | Acker et al. | |
| 7,308,968 B2 | 12/2007 | Denison | |
| 7,331,349 B2 | 2/2008 | Brady et al. | |
| 7,391,983 B2 | 6/2008 | Tatematsu et al. | |
| 7,406,966 B2 | 8/2008 | Wondka | |
| 7,407,279 B2 | 8/2008 | Nakashima | |
| 7,416,073 B1 | 8/2008 | Talken et al. | |
| 7,426,950 B2 | 9/2008 | Takagi | |
| 7,462,154 B2 | 12/2008 | Yamamori et al. | |
| 7,472,707 B2 | 1/2009 | Wood et al. | |
| 7,481,219 B2 | 1/2009 | Lewis et al. | |
| 7,481,220 B2 | 1/2009 | Meyer et al. | |
| 7,490,359 B2 | 2/2009 | Landis | |
| 7,491,351 B2 | 2/2009 | Taylor et al. | |
| 7,493,900 B1 | 2/2009 | Japuntich et al. | |
| 7,493,902 B2 | 2/2009 | White et al. | |
| 7,550,243 B2 | 6/2009 | Matsumoto et al. | |
| D597,200 S | 7/2009 | Grimsley | |
| 7,588,139 B1 | 9/2009 | Campbell, III | |
| 7,597,190 B2 | 10/2009 | Lee | |
| 7,614,401 B2 * | 11/2009 | Thompson | A61M 25/02 |
| | | | 128/207.18 |
| 7,618,431 B2 | 11/2009 | Roehm, III et al. | |
| 7,635,323 B2 | 12/2009 | Halbridge | |
| 7,661,309 B2 | 2/2010 | Lan et al. | |
| 7,726,309 B2 | 6/2010 | Ho et al. | |
| 7,726,314 B1 | 6/2010 | Ming | |
| 7,735,490 B2 | 6/2010 | Rinaldi | |
| 7,753,051 B2 | 7/2010 | Burrow et al. | |
| 7,768,473 B2 | 8/2010 | Kardohely | |
| 7,814,911 B2 | 10/2010 | Bordewick et al. | |
| 7,841,026 B2 | 11/2010 | Makris et al. | |
| 7,845,352 B2 | 12/2010 | Sleeper et al. | |
| 7,850,052 B2 | 12/2010 | Thatcher | |
| 7,856,979 B2 | 12/2010 | Doshi et al. | |
| 7,856,982 B2 | 12/2010 | Matula, Jr. et al. | |
| 7,874,293 B2 | 1/2011 | Gunaratnam et al. | |
| 7,878,200 B2 | 2/2011 | Zollinger et al. | |
| 7,905,028 B2 | 3/2011 | Sieber | |
| 7,907,882 B2 | 3/2011 | Hara | |
| 7,971,590 B2 | 7/2011 | Frater et al. | |
| 7,975,693 B2 | 7/2011 | Geiselhart et al. | |
| 7,993,553 B2 | 8/2011 | Brown | |
| 8,042,691 B2 | 10/2011 | Brosseuk et al. | |
| 8,136,527 B2 | 3/2012 | Wondka | |
| 8,171,934 B1 | 5/2012 | Ho | |
| 8,171,935 B2 | 5/2012 | Cortez et al. | |
| 8,211,152 B2 | 7/2012 | Snyder et al. | |
| 8,224,219 B2 | 7/2012 | Ishino et al. | |
| 8,256,421 B2 | 9/2012 | Ho et al. | |
| 8,262,864 B2 | 9/2012 | Takamura | |
| 8,290,387 B2 | 10/2012 | Hara | |
| 8,297,285 B2 | 10/2012 | Henry et al. | |
| 8,346,140 B2 | 1/2013 | Yasumoto | |
| 8,353,294 B2 | 1/2013 | Frater et al. | |
| 8,365,735 B2 | 2/2013 | Chang | |
| 8,365,736 B2 | 2/2013 | Doshi et al. | |
| 8,385,801 B2 | 2/2013 | Sugaya | |
| 8,393,324 B1 | 3/2013 | Saad | |
| 8,393,327 B2 | 3/2013 | Omura et al. | |
| 8,402,966 B2 | 3/2013 | Morgan, III et al. | |
| 8,434,249 B2 | 5/2013 | Wieneke | |
| 8,434,485 B2 | 5/2013 | Osier et al. | |
| 8,464,709 B2 | 6/2013 | Wedemeyer | |
| 8,478,180 B2 | 7/2013 | Arimoto et al. | |
| 8,483,603 B2 | 7/2013 | Nihonyanagi et al. | |
| 8,509,668 B2 | 8/2013 | Takemura | |
| 8,517,022 B2 | 8/2013 | Halling et al. | |
| 8,573,201 B2 | 11/2013 | Rummery et al. | |
| 8,573,219 B2 | 11/2013 | Wondka | |
| 8,596,271 B2 | 12/2013 | Matula, Jr. et al. | |
| 8,616,209 B2 | 12/2013 | Amarasinghe | |
| 8,631,793 B2 | 1/2014 | Omura et al. | |
| 8,631,799 B2 | 1/2014 | Davenport et al. | |
| 8,632,455 B2 | 1/2014 | Woodruff et al. | |
| 8,636,007 B2 | 1/2014 | Rummery et al. | |
| 8,639,313 B2 | 1/2014 | Westbrook et al. | |
| 8,640,697 B2 | 2/2014 | Reed | |
| 8,640,710 B2 | 2/2014 | Matthews | |
| 8,667,964 B2 | 3/2014 | Ho | |
| 8,673,433 B2 | 3/2014 | Reif et al. | |
| 8,701,667 B1 | 4/2014 | Ho et al. | |
| 8,728,280 B2 | 5/2014 | Eagles et al. | |
| 8,746,743 B2 | 6/2014 | Kawai et al. | |
| 8,752,551 B2 | 6/2014 | Chandran et al. | |
| 8,764,927 B2 | 7/2014 | Bäck | |
| 8,813,749 B2 | 8/2014 | Hernandez et al. | |
| 8,820,377 B2 | 9/2014 | Ueda et al. | |
| 8,826,909 B2 | 9/2014 | Nashed | |
| 8,838,000 B2 | 9/2014 | Tamura | |
| 8,851,078 B2 | 10/2014 | Newman et al. | |
| 8,857,435 B2 | 10/2014 | Matula, Jr. et al. | |
| 8,887,725 B2 | 11/2014 | Hernandez et al. | |
| 8,910,626 B2 | 12/2014 | Matula, Jr. et al. | |
| 8,950,404 B2 | 2/2015 | Formica et al. | |
| 8,956,373 B2 | 2/2015 | Ford et al. | |
| 8,958,735 B2 | 2/2015 | Arimoto | |
| 8,978,648 B2 | 3/2015 | Formica et al. | |
| 8,985,115 B2 | 3/2015 | Baecke et al. | |
| 8,985,117 B2 | 3/2015 | Gunaratnam et al. | |
| 8,997,747 B2 | 4/2015 | Hobson et al. | |
| 9,010,330 B2 | 4/2015 | Barlow et al. | |
| 9,044,562 B2 | 6/2015 | Dillingham et al. | |

(56) References Cited

U.S. PATENT DOCUMENTS

| | | | |
|---|---|---|---|
| 9,061,113 B2 | 6/2015 | Thomas et al. |
| 9,072,855 B2 | 7/2015 | McAuley et al. |
| 9,119,708 B2 | 9/2015 | Wanderer et al. |
| 9,119,975 B2 | 9/2015 | Hu et al. |
| 9,126,767 B2 | 9/2015 | Carter |
| 9,131,894 B2 | 9/2015 | Kato et al. |
| 9,138,554 B2 | 9/2015 | Colbaugh |
| 9,162,034 B2 | 10/2015 | Veliss et al. |
| 9,179,209 B2 | 11/2015 | Emilsson |
| 9,182,062 B2 | 11/2015 | Kwok et al. |
| 9,199,053 B1 | 12/2015 | Allum et al. |
| 9,199,512 B2 | 12/2015 | Ueyoko et al. |
| 9,215,998 B2 | 12/2015 | Reinhold, Jr. et al. |
| 9,216,264 B2 | 12/2015 | Ho |
| 9,247,775 B2 | 2/2016 | Suzuki et al. |
| 9,248,251 B2 | 2/2016 | Gunaratnam |
| 9,259,542 B2 | 2/2016 | Acker et al. |
| 9,273,738 B2 | 3/2016 | Rehfus et al. |
| 9,274,555 B2 | 3/2016 | Otsuka et al. |
| 9,302,064 B2 | 4/2016 | Hussain |
| 9,316,974 B2 | 4/2016 | Yamaguchi et al. |
| 9,320,923 B2 | 4/2016 | Koehler |
| 9,375,545 B2 | 6/2016 | Darkin et al. |
| 9,381,106 B2 | 7/2016 | Gilmer et al. |
| 9,387,300 B2 | 7/2016 | Javier et al. |
| 9,393,378 B2 | 7/2016 | Fearnot et al. |
| 9,415,182 B2 | 8/2016 | Schneider et al. |
| 9,480,958 B2 | 11/2016 | Hollmann et al. |
| 9,492,627 B2 | 11/2016 | Amarasinghe |
| 9,526,857 B2 | 12/2016 | Rummery et al. |
| 9,541,235 B2 | 1/2017 | Travis |
| 9,562,636 B2 | 2/2017 | Zivanovic et al. |
| 9,582,035 B2 | 2/2017 | Connor |
| 9,597,541 B2 | 3/2017 | Hinds et al. |
| 9,599,009 B2 | 3/2017 | Smemo et al. |
| 9,600,030 B2 | 3/2017 | Bailey et al. |
| 9,625,065 B2 | 4/2017 | Feldhahn et al. |
| 9,651,278 B2 | 5/2017 | Palmieri et al. |
| 9,655,783 B2 | 5/2017 | McNeal |
| 9,656,037 B2 | 5/2017 | Guyette |
| 9,668,694 B2 | 6/2017 | Badower |
| 9,685,265 B2 | 6/2017 | Stutz |
| 9,687,195 B2 | 6/2017 | Sims et al. |
| 9,687,619 B2 | 6/2017 | Stuebiger et al. |
| 9,687,624 B2 | 6/2017 | Haas |
| 9,694,930 B2 | 7/2017 | Lane et al. |
| 9,704,412 B2 | 7/2017 | Wells et al. |
| 9,707,366 B2 | 7/2017 | Metelits |
| 9,707,393 B2 | 7/2017 | Hsueh et al. |
| 9,724,546 B2 | 8/2017 | Huggins et al. |
| 9,731,090 B2 | 8/2017 | Ovinsky et al. |
| 9,737,678 B2 | 8/2017 | Formica et al. |
| 9,744,325 B2 | 8/2017 | Ho |
| 9,754,079 B2 | 9/2017 | Knight et al. |
| 9,763,580 B2 | 9/2017 | Sadleir et al. |
| 9,802,018 B2 | 10/2017 | Ging et al. |
| 9,808,589 B2 | 11/2017 | Gunaratnam et al. |
| 9,826,789 B2 | 11/2017 | Dey et al. |
| 9,826,935 B2 | 11/2017 | Martinez et al. |
| 9,827,391 B2 | 11/2017 | Kwok et al. |
| 9,833,591 B1 | 12/2017 | Ormrod |
| 9,833,938 B2 | 12/2017 | Lane et al. |
| 9,839,798 B2 | 12/2017 | Franke et al. |
| 9,867,571 B2 | 1/2018 | Aimone et al. |
| D811,581 S | 2/2018 | Danford |
| 9,889,267 B2 | 2/2018 | Wells et al. |
| 9,901,699 B2 | 2/2018 | Veliss et al. |
| 9,909,953 B2 | 3/2018 | Shen et al. |
| 9,925,348 B2 | 3/2018 | Payton et al. |
| 9,937,312 B2 | 4/2018 | Kwok et al. |
| 9,943,443 B2 | 4/2018 | Schwartz |
| 9,949,688 B2 | 4/2018 | Goldman et al. |
| 9,961,969 B2 | 5/2018 | Kawabata et al. |
| 9,981,102 B2 | 5/2018 | Veliss et al. |
| 9,993,605 B2 | 6/2018 | Barlow et al. |

| | | | | |
|---|---|---|---|---|
| 9,999,392 B1 | 6/2018 | Wordham et al. | | |
| 9,999,738 B2 | 6/2018 | Chimenti et al. | | |
| 10,004,866 B2 | 6/2018 | Davis | | |
| 10,016,572 B2 | 7/2018 | Haibach | | |
| 10,022,073 B2 | 7/2018 | Baxi et al. | | |
| 10,029,062 B2 | 7/2018 | Kwok et al. | | |
| 10,039,893 B2 | 8/2018 | Frater et al. | | |
| 10,039,894 B2 | 8/2018 | Walls et al. | | |
| 10,046,132 B2 | 8/2018 | Eifler et al. | | |
| 10,046,251 B2 | 8/2018 | Grave et al. | | |
| 10,052,448 B2 | 8/2018 | Barlow et al. | | |
| 10,058,259 B1 | 8/2018 | Kryzpow et al. | | |
| 10,061,352 B1 | 8/2018 | Trail | | |
| D828,917 S | 9/2018 | Prentice et al. | | |
| 10,076,251 B2 | 9/2018 | Tu et al. | | |
| 10,076,624 B2 | 9/2018 | Ozolins et al. | | |
| 10,080,858 B2 | 9/2018 | Chodkowski et al. | | |
| 10,086,220 B2 | 10/2018 | Dolan et al. | | |
| 10,117,599 B2 | 11/2018 | Orr et al. | | |
| 10,130,785 B2 | 11/2018 | Dravitzki et al. | | |
| 10,137,271 B2 | 11/2018 | McAuley et al. | | |
| 10,155,096 B2 | 12/2018 | Amarasinghe | | |
| 10,159,779 B2 | 12/2018 | Olivarez | | |
| 10,166,358 B2 | 1/2019 | Swift et al. | | |
| 10,172,533 B2 | 1/2019 | Kulach et al. | | |
| D841,149 S | 2/2019 | Collazo et al. | | |
| D841,150 S | 2/2019 | Collazo et al. | | |
| 10,194,702 B2 | 2/2019 | Cobbett et al. | | |
| 10,195,385 B2 | 2/2019 | Lang et al. | | |
| 10,198,930 B2 | 2/2019 | Melton et al. | | |
| 10,207,071 B2 | 2/2019 | Hobson et al. | | |
| 10,226,208 B2 | 3/2019 | Emery et al. | | |
| 10,231,669 B2 | 3/2019 | Wordham et al. | | |
| 10,232,136 B2 | 3/2019 | Kapust et al. | | |
| D849,933 S | 5/2019 | Collazo et al. | | |
| 10,279,138 B2 | 5/2019 | Ovzinsky et al. | | |
| D851,750 S | 6/2019 | Collazo et al. | | |
| D863,544 S | 10/2019 | Collazo et al. | | |
| 10,478,580 B2 * | 11/2019 | Klenner | A61M 16/0003 | |
| 10,500,424 B2 | 12/2019 | Rummery et al. | | |
| D885,559 S | 5/2020 | Gabriel | | |
| 10,716,912 B2 | 7/2020 | Holyoake et al. | | |
| 11,040,165 B2 | 6/2021 | Kooij et al. | | |
| 11,110,245 B2 * | 9/2021 | White | A61M 16/0672 | |
| D950,709 S | 5/2022 | Holyoake et al. | | |
| 11,324,908 B2 | 5/2022 | Holyoake et al. | | |
| 11,666,723 B2 * | 6/2023 | Schwaiger | A61M 16/0672 | |
| | | | 128/207.18 | |
| 2001/0004894 A1 | 6/2001 | Bourdon | | |
| 2001/0022180 A1 | 9/2001 | Serneia | | |
| 2002/0055685 A1 | 5/2002 | Levitsky et al. | | |
| 2002/0068654 A1 | 6/2002 | Luk et al. | | |
| 2002/0086752 A1 | 7/2002 | Friedrich et al. | | |
| 2002/0096173 A1 | 7/2002 | Berthon-Jones et al. | | |
| 2002/0115513 A1 | 8/2002 | Yuan | | |
| 2002/0155911 A1 | 10/2002 | Hummel et al. | | |
| 2003/0004025 A1 | 1/2003 | Okuno et al. | | |
| 2003/0006646 A1 | 1/2003 | Musselman et al. | | |
| 2003/0079749 A1 * | 5/2003 | Strickland | A61M 16/0833 | |
| | | | 128/203.22 | |
| 2003/0092522 A1 | 5/2003 | Sauter et al. | | |
| 2003/0116163 A1 * | 6/2003 | Wood | A61M 16/0666 | |
| | | | 128/207.18 | |
| 2003/0154978 A1 | 8/2003 | Gradon | | |
| 2003/0154980 A1 | 8/2003 | Berthon-Jones et al. | | |
| 2003/0172936 A1 * | 9/2003 | Wilkie | A61M 16/0633 | |
| | | | 128/207.18 | |
| 2004/0016432 A1 | 1/2004 | Genger et al. | | |
| 2004/0020493 A1 * | 2/2004 | Wood | A61M 16/208 | |
| | | | 128/207.18 | |
| 2004/0094149 A1 | 5/2004 | Natale | | |
| 2004/0106485 A1 | 6/2004 | Prinsen et al. | | |
| 2004/0129273 A1 | 7/2004 | Hickle | | |
| 2004/0134250 A1 | 7/2004 | Durney et al. | | |
| 2004/0139973 A1 * | 7/2004 | Wright | A61M 16/0672 | |
| | | | 128/207.18 | |
| 2004/0164613 A1 | 8/2004 | Konickson et al. | | |
| 2004/0244799 A1 | 12/2004 | Landis | | |
| 2005/0000024 A1 | 1/2005 | Jakubowski | | |

(56) References Cited

U.S. PATENT DOCUMENTS

| | | |
|---|---|---|
| 2005/0009655 A1 | 1/2005 | Kubo et al. |
| 2005/0011522 A1 | 1/2005 | Ho et al. |
| 2005/0028822 A1 | 2/2005 | Sleeper et al. |
| 2005/0061321 A1 | 3/2005 | Jones |
| 2005/0090618 A1 | 4/2005 | Okuno |
| 2005/0113200 A1 | 5/2005 | Okuno et al. |
| 2005/0199239 A1 | 9/2005 | Lang et al. |
| 2005/0205096 A1 | 9/2005 | Matula et al. |
| 2005/0215373 A1 | 9/2005 | Lodge |
| 2005/0265151 A1 | 12/2005 | Kimura et al. |
| 2005/0279351 A1 | 12/2005 | Lewis et al. |
| 2006/0084542 A1 | 4/2006 | Kubo et al. |
| 2006/0112962 A1 | 6/2006 | Tebbutt et al. |
| 2006/0163039 A1 | 7/2006 | Marshall et al. |
| 2006/0213521 A1 | 9/2006 | Radney |
| 2006/0243279 A1 | 11/2006 | Hinkle |
| 2006/0270504 A1 | 11/2006 | Krause |
| 2007/0045152 A1 | 3/2007 | Kwok et al. |
| 2007/0060429 A1 | 3/2007 | Ono et al. |
| 2007/0087878 A1 | 4/2007 | Ogawa et al. |
| 2007/0105674 A1 | 5/2007 | Hogn |
| 2007/0107732 A1 | 5/2007 | Dennis et al. |
| 2007/0235034 A1 | 10/2007 | Weaver |
| 2007/0246043 A1 | 10/2007 | Kwok et al. |
| 2007/0277828 A1 | 12/2007 | Ho et al. |
| 2007/0290248 A1 | 12/2007 | Weis |
| 2008/0000472 A1 | 1/2008 | Wall |
| 2008/0011305 A1 | 1/2008 | Chandran et al. |
| 2008/0038101 A1 | 2/2008 | Klatt |
| 2008/0047560 A1 | 2/2008 | Veliss et al. |
| 2008/0060649 A1 | 3/2008 | Veliss et al. |
| 2008/0064548 A1 | 3/2008 | Abate et al. |
| 2008/0099022 A1 | 5/2008 | Gebrewold et al. |
| 2008/0142015 A1 | 6/2008 | Groll |
| 2008/0194997 A1 | 8/2008 | Zhang |
| 2009/0028617 A1 | 1/2009 | Katakabe et al. |
| 2009/0042683 A1 | 2/2009 | Tohara |
| 2009/0054189 A1 | 2/2009 | Tani et al. |
| 2009/0055999 A1 | 3/2009 | Garcia |
| 2009/0078259 A1 | 3/2009 | Kooij et al. |
| 2009/0091432 A1 | 4/2009 | Koser et al. |
| 2009/0173350 A1* | 7/2009 | Swanson ............. A61M 16/085 |
| | | 128/207.18 |
| 2009/0183739 A1* | 7/2009 | Wondka ............ A61M 16/0875 |
| | | 128/207.18 |
| 2009/0191998 A1 | 7/2009 | De Meco et al. |
| 2009/0199610 A1 | 8/2009 | Sato et al. |
| 2009/0223518 A1 | 9/2009 | Kwok et al. |
| 2009/0234201 A1 | 9/2009 | Huang et al. |
| 2009/0254012 A1 | 10/2009 | Gavriely et al. |
| 2009/0283096 A1 | 11/2009 | Cerbini |
| 2009/0291796 A1 | 11/2009 | Mitsutomi et al. |
| 2009/0321191 A1 | 12/2009 | Broyan |
| 2010/0012221 A1 | 1/2010 | Lien |
| 2010/0018534 A1 | 1/2010 | Veliss et al. |
| 2010/0122704 A1 | 5/2010 | Moenning |
| 2010/0132716 A1* | 6/2010 | Selvarajan ........ A61M 16/0666 |
| | | 128/207.18 |
| 2010/0152564 A1 | 6/2010 | Nguyen et al. |
| 2010/0261019 A1 | 10/2010 | Sano et al. |
| 2010/0313891 A1 | 12/2010 | Veliss et al. |
| 2011/0067704 A1 | 3/2011 | Kooij et al. |
| 2011/0108041 A1 | 5/2011 | Sather et al. |
| 2011/0120460 A1 | 5/2011 | Wallnewitz et al. |
| 2011/0185541 A1 | 8/2011 | Guptill |
| 2011/0197893 A1 | 8/2011 | Ziv et al. |
| 2011/0247619 A1 | 10/2011 | Formica et al. |
| 2011/0259331 A1 | 10/2011 | Witt |
| 2011/0259335 A1 | 10/2011 | Sullivan |
| 2011/0265796 A1 | 11/2011 | Amarasinghe et al. |
| 2011/0272986 A1 | 11/2011 | Iacovoni et al. |
| 2011/0284347 A1 | 11/2011 | MacLachlan et al. |
| 2011/0308517 A1 | 12/2011 | Emilsson et al. |
| 2012/0017901 A1 | 1/2012 | Mainusch et al. |
| 2012/0029145 A1 | 2/2012 | Brown |
| 2012/0030912 A1 | 2/2012 | Turdjian et al. |
| 2012/0035435 A1 | 2/2012 | Choi et al. |
| 2012/0047614 A1 | 3/2012 | Choi |
| 2012/0049533 A1 | 3/2012 | Kelly |
| 2012/0065621 A1 | 3/2012 | Steegers et al. |
| 2012/0067349 A1 | 3/2012 | Barlow et al. |
| 2012/0071285 A1 | 3/2012 | Tay |
| 2012/0094795 A1 | 4/2012 | Wang |
| 2012/0125338 A1 | 5/2012 | Yarahmadi |
| 2012/0150119 A1 | 6/2012 | Schaeffer |
| 2012/0198952 A1 | 8/2012 | Mamba |
| 2012/0298104 A1 | 11/2012 | Müller et al. |
| 2012/0318270 A1 | 12/2012 | McAuley et al. |
| 2012/0318271 A1 | 12/2012 | Ho |
| 2012/0318274 A1 | 12/2012 | Ho |
| 2012/0325219 A1 | 12/2012 | Smith et al. |
| 2013/0008448 A1 | 1/2013 | Todd |
| 2013/0019870 A1 | 1/2013 | Collazo et al. |
| 2013/0052014 A1 | 2/2013 | Kelly |
| 2013/0133646 A1 | 5/2013 | Rose et al. |
| 2013/0199537 A1 | 8/2013 | Formica |
| 2013/0206139 A1 | 8/2013 | Krepel et al. |
| 2013/0211208 A1 | 8/2013 | Varadan et al. |
| 2013/0230674 A1 | 9/2013 | Curti et al. |
| 2013/0237355 A1 | 9/2013 | Lubojatzky |
| 2013/0237397 A1 | 9/2013 | Seiler |
| 2013/0276781 A1 | 10/2013 | Steelman et al. |
| 2014/0000626 A1 | 1/2014 | O'Connor et al. |
| 2014/0053844 A1 | 2/2014 | Rummery et al. |
| 2014/0102456 A1 | 4/2014 | Ovizinsky et al. |
| 2014/0116429 A1 | 5/2014 | Patil et al. |
| 2014/0137870 A1 | 5/2014 | Barlow et al. |
| 2014/0186909 A1 | 7/2014 | Calzia et al. |
| 2014/0216452 A1* | 8/2014 | Miller .................... B01D 53/34 |
| | | 128/202.26 |
| 2014/0261440 A1 | 9/2014 | Chodkowski |
| 2014/0264975 A1 | 9/2014 | Bath et al. |
| 2014/0283841 A1 | 9/2014 | Chodkowski et al. |
| 2014/0299131 A1 | 10/2014 | Chodkowski et al. |
| 2014/0311492 A1 | 10/2014 | Stuebiger et al. |
| 2014/0345604 A1 | 11/2014 | Wang et al. |
| 2015/0059764 A1 | 3/2015 | Metelits |
| 2015/0065904 A1 | 3/2015 | Stenzler et al. |
| 2015/0075524 A1 | 3/2015 | Millar |
| 2015/0139703 A1 | 5/2015 | Takazawa |
| 2015/0151070 A1 | 6/2015 | Capra et al. |
| 2015/0151071 A1 | 6/2015 | Von Moger et al. |
| 2015/0157220 A1 | 6/2015 | Fish et al. |
| 2015/0201867 A1 | 7/2015 | Peindl et al. |
| 2015/0231355 A1 | 8/2015 | Kuo |
| 2015/0246198 A1 | 9/2015 | Bearne et al. |
| 2015/0246200 A1 | 9/2015 | Neff et al. |
| 2015/0250237 A1 | 9/2015 | Shoham et al. |
| 2015/0258823 A1 | 9/2015 | Otsuka et al. |
| 2015/0283350 A1 | 10/2015 | Miller et al. |
| 2015/0352306 A1 | 12/2015 | Scheiner et al. |
| 2015/0355585 A1 | 12/2015 | Suzuki et al. |
| 2015/0360060 A1 | 12/2015 | Dehmke et al. |
| 2016/0008564 A1 | 1/2016 | Grashow |
| 2016/0022954 A1 | 1/2016 | Bath et al. |
| 2016/0030696 A1 | 2/2016 | Klenner et al. |
| 2016/0089261 A1 | 3/2016 | Quinn |
| 2016/0095996 A1* | 4/2016 | Gusky ............... A61M 16/0816 |
| | | 128/205.25 |
| 2016/0106367 A1 | 4/2016 | Jorov et al. |
| 2016/0114118 A1 | 4/2016 | Gunaratnam et al. |
| 2016/0144144 A1 | 5/2016 | Smith et al. |
| 2016/0150958 A1 | 6/2016 | Kranz |
| 2016/0153853 A1 | 6/2016 | Brenner et al. |
| 2016/0157779 A1 | 6/2016 | Baxi et al. |
| 2016/0199612 A1 | 7/2016 | Foote et al. |
| 2016/0213281 A1 | 7/2016 | Eckerbom et al. |
| 2016/0228666 A1 | 8/2016 | Sullivan et al. |
| 2016/0256653 A1 | 9/2016 | McAuley et al. |
| 2016/0256655 A1 | 9/2016 | Mah et al. |
| 2016/0297505 A1 | 10/2016 | Caprice et al. |
| 2016/0317770 A1 | 11/2016 | Kushida et al. |
| 2016/0324487 A1 | 11/2016 | Guo et al. |
| 2016/0346530 A1 | 12/2016 | Jeffrey et al. |

(56) References Cited

U.S. PATENT DOCUMENTS

| | | | |
|---|---|---|---|
| 2016/0361512 A1 | 12/2016 | Lawrenson et al. | |
| 2016/0367189 A1 | 12/2016 | Aimone et al. | |
| 2016/0375205 A1 | 12/2016 | Cressman | |
| 2016/0377149 A1 | 12/2016 | Furusawa | |
| 2017/0002905 A1 | 1/2017 | Sessions | |
| 2017/0028150 A1 | 2/2017 | McNulty | |
| 2017/0042478 A1 | 2/2017 | Zheng et al. | |
| 2017/0043113 A1 | 2/2017 | Ng et al. | |
| 2017/0059984 A1 | 3/2017 | Kim et al. | |
| 2017/0065785 A1 | 3/2017 | Roberts | |
| 2017/0065787 A1 | 3/2017 | Rummery et al. | |
| 2017/0081124 A1 | 3/2017 | Steinhert | |
| 2017/0151408 A1 | 6/2017 | Lun et al. | |
| 2017/0157435 A1 | 6/2017 | Choi | |
| 2017/0157436 A1 | 6/2017 | Hosmer | |
| 2017/0173290 A1 | 6/2017 | Pedro et al. | |
| 2017/0202514 A1 | 7/2017 | Nousiainen et al. | |
| 2017/0203070 A1 | 7/2017 | Lei | |
| 2017/0203071 A1 | 7/2017 | Lawrenson et al. | |
| 2017/0224065 A1 | 8/2017 | Nipke et al. | |
| 2017/0224943 A1 | 8/2017 | Creusot et al. | |
| 2017/0266403 A1 | 9/2017 | Prentice et al. | |
| 2017/0274167 A1 | 9/2017 | Huddart et al. | |
| 2017/0281394 A1 | 10/2017 | Viken | |
| 2017/0304576 A1 | 10/2017 | Lawrenson et al. | |
| 2017/0304577 A1 | 10/2017 | Bearne et al. | |
| 2017/0312465 A1 | 11/2017 | Kwok et al. | |
| 2017/0312468 A1 | 11/2017 | Formica et al. | |
| 2017/0314641 A1 | 11/2017 | Kamba et al. | |
| 2017/0333662 A1 | 11/2017 | Ovizinsky et al. | |
| 2017/0347923 A1 | 12/2017 | Roh | |
| 2017/0348500 A1 | 12/2017 | Johnson et al. | |
| 2018/0001046 A1 | 1/2018 | Rummery et al. | |
| 2018/0036503 A1 | 2/2018 | Mohamed | |
| 2018/0036505 A1 | 2/2018 | Bornholdt et al. | |
| 2018/0043121 A1 | 2/2018 | Goulitski et al. | |
| 2018/0043123 A1 | 2/2018 | Lei | |
| 2018/0064897 A1 | 3/2018 | Kwok et al. | |
| 2018/0064968 A1 | 3/2018 | Taslagyan | |
| 2018/0071476 A1 | 3/2018 | Neff | |
| 2018/0077481 A1 | 3/2018 | Kim | |
| 2018/0078727 A1 | 3/2018 | Johnson et al. | |
| 2018/0099112 A1 | 4/2018 | Belenkiy | |
| 2018/0160749 A1 | 6/2018 | Kim | |
| 2018/0162697 A1 | 6/2018 | Schmidt et al. | |
| 2018/0185598 A1 | 7/2018 | Olsen et al. | |
| 2018/0192727 A1 | 7/2018 | Chen | |
| 2018/0192954 A1 | 7/2018 | Lumme et al. | |
| 2018/0193581 A1 | 7/2018 | Frater et al. | |
| 2018/0207385 A1 | 7/2018 | Freestone et al. | |
| 2018/0213918 A1 | 8/2018 | Graves | |
| 2018/0214655 A1 | 8/2018 | Kooij et al. | |
| 2018/0214656 A1 | 8/2018 | McLaren | |
| 2018/0221191 A1 | 8/2018 | Scott et al. | |
| 2018/0236198 A1 | 8/2018 | Veliss et al. | |
| 2018/0236276 A1 | 8/2018 | Moon | |
| 2018/0244499 A1 | 8/2018 | Zapf | |
| 2018/0250482 A1 | 9/2018 | Barlow et al. | |
| 2018/0256844 A1 | 9/2018 | Galgali et al. | |
| 2018/0264220 A1 | 9/2018 | Hurt | |
| 2018/0289914 A1 | 10/2018 | Kwok et al. | |
| 2018/0301224 A1 | 10/2018 | Matichuk et al. | |
| 2018/0318540 A1 | 11/2018 | Barlow et al. | |
| 2018/0338704 A1 | 11/2018 | Laman et al. | |
| 2018/0355682 A1 | 12/2018 | Pessin et al. | |
| 2018/0361096 A1 | 12/2018 | Grashow et al. | |
| 2018/0361099 A1 | 12/2018 | Wells | |
| 2019/0009046 A1 | 1/2019 | Kooij et al. | |
| 2019/0021668 A1 | 1/2019 | Fujita | |
| 2019/0022343 A1 | 1/2019 | Kooij | |
| 2019/0038226 A1 | 2/2019 | Davidson et al. | |
| 2019/0053568 A1 | 2/2019 | Choukeir | |
| 2019/0062118 A1 | 2/2019 | Valjus et al. | |
| 2019/0076613 A1 | 3/2019 | Amarasinghe | |
| 2019/0082968 A1 | 3/2019 | Karnik et al. | |
| 2019/0083733 A1 | 3/2019 | Gulliver et al. | |
| 2019/0090763 A1 | 3/2019 | Woerlee et al. | |
| 2019/0091068 A1 | 3/2019 | Schwartz | |
| 2019/0091430 A1 | 3/2019 | Barlow et al. | |
| 2019/0091433 A1 | 3/2019 | Barlow et al. | |
| 2019/0134332 A1 | 5/2019 | Kwok et al. | |
| 2019/0151589 A1 | 5/2019 | Kwok et al. | |
| 2019/0175861 A1 | 6/2019 | Holyoake et al. | |
| 2019/0209799 A1 | 7/2019 | Ovzinsky et al. | |
| 2019/0344036 A1 | 11/2019 | O'Donnell et al. | |
| 2020/0360637 A1 | 11/2020 | Holyoake et al. | |
| 2020/0368471 A1 | 11/2020 | Holyoake et al. | |
| 2020/0368479 A1 | 11/2020 | Flynn et al. | |
| 2022/0152334 A1* | 5/2022 | Bell | A61M 16/0683 |
| 2024/0335632 A1 | 10/2024 | Holyoake et al. | |

FOREIGN PATENT DOCUMENTS

| | | | |
|---|---|---|---|
| AU | 505422 | B2 | 11/1979 |
| AU | 198317585 | A | 2/1984 |
| AU | 542540 | B2 | 2/1985 |
| AU | 543022 | B2 | 3/1985 |
| AU | 580417 | B | 1/1989 |
| AU | 587397 | B | 8/1989 |
| AU | 1999063955 | A1 | 3/2001 |
| AU | 2002330895 | A1 | 5/2003 |
| AU | 2004203100 | A1 | 7/2004 |
| AU | 2004202274 | | 12/2004 |
| AU | 20042666693 | B2 | 3/2005 |
| AU | 2004303643 | A1 | 7/2005 |
| AU | 784321 | B2 | 3/2006 |
| AU | 2005287747 | A1 | 3/2006 |
| AU | 2008203174 | A1 | 8/2008 |
| AU | 2005206344 | B2 | 9/2009 |
| AU | 2007245691 | B2 | 12/2010 |
| AU | 2006299938 | B2 | 5/2011 |
| AU | 2005253641 | B2 | 12/2011 |
| AU | 2009326861 | B2 | 12/2013 |
| AU | 2013200267 | B2 | 4/2014 |
| AU | 2011308094 | B2 | 5/2014 |
| AU | 2011308095 | B2 | 10/2014 |
| AU | 2008/316306 | B2 | 2/2015 |
| AU | 2014201200 | B2 | 8/2015 |
| AU | 2014224136 | B2 | 4/2016 |
| AU | 2016101634 | A4 | 10/2016 |
| AU | 2017216448 | A1 | 3/2018 |
| AU | 2018100107 | A4 | 3/2018 |
| AU | 2018201087 | | 4/2018 |
| CA | 1058914 | A | 7/1979 |
| CA | 1137793 | A1 | 12/1982 |
| CA | 1142234 | A1 | 3/1983 |
| CA | 1158071 | A1 | 12/1983 |
| CA | 1165593 | A | 4/1984 |
| CA | 1178752 | A | 12/1984 |
| CA | 1267257 | A | 4/1990 |
| CA | 2004020 | A1 | 5/1990 |
| CA | 1291349 | C | 10/1991 |
| CA | 1307395 | C | 9/1992 |
| CA | 2087812 | C | 12/1995 |
| CA | 2269819 | A1 | 6/1998 |
| CA | 2246823 | A1 | 3/1999 |
| CA | 2263627 | A1 | 9/1999 |
| CA | 2214732 | C | 5/2002 |
| CA | 2310350 | C | 12/2004 |
| CA | 2587526 | A1 | 5/2006 |
| CA | 2798822 | A1 | 11/2011 |
| CA | 2750638 | A1 | 2/2013 |
| CA | 2602653 | C | 1/2016 |
| CH | 701564 | A2 | 1/2011 |
| CH | 701918 | A2 | 3/2011 |
| CN | 2114727 | U | 9/1992 |
| CN | 2116121 | U | 9/1992 |
| CN | 2305523 | Y | 1/1999 |
| CN | 2334953 | Y | 8/1999 |
| CN | 1826151 | A | 8/2006 |
| CN | 2903582 | Y | 5/2007 |
| CN | 101204328 | | 6/2007 |
| CN | 201043586 | Y | 4/2008 |
| CN | 101495170 | | 7/2009 |

(56) References Cited

FOREIGN PATENT DOCUMENTS

| | | |
|---|---|---|
| CN | 101516427 | 8/2009 |
| CN | 101629612 A | 1/2010 |
| CN | 201496473 U | 6/2010 |
| CN | 202040271 U | 11/2011 |
| CN | 202251664 U | 5/2012 |
| CN | 102537208 A | 7/2012 |
| CN | 102762249 A | 10/2012 |
| CN | 203033307 U | 7/2013 |
| CN | 103153379 A | 12/2013 |
| CN | 203486450 U | 3/2014 |
| CN | 203614658 U | 5/2014 |
| CN | 203614659 U | 5/2014 |
| CN | 104114637 A | 10/2014 |
| CN | 104254709 A | 12/2014 |
| CN | 104295665 A | 1/2015 |
| CN | 104295710 A | 1/2015 |
| CN | 104302337 | 1/2015 |
| CN | 104315082 A | 1/2015 |
| CN | 104455310 A | 3/2015 |
| CN | 204200955 U | 3/2015 |
| CN | 104476789 A | 4/2015 |
| CN | 104524675 A | 4/2015 |
| CN | 204312619 U | 5/2015 |
| CN | 204327859 U | 5/2015 |
| CN | 204344806 U | 5/2015 |
| CN | 105102048 A | 11/2015 |
| CN | 204736990 U | 11/2015 |
| CN | 204805430 U | 11/2015 |
| CN | 105190089 A | 12/2015 |
| CN | 204985507 U | 1/2016 |
| CN | 205226231 U | 5/2016 |
| CN | 105752809 A | 7/2016 |
| CN | 205534007 U | 8/2016 |
| CN | 205555824 U | 9/2016 |
| CN | 106005898 A | 10/2016 |
| CN | 205639467 U | 10/2016 |
| CN | 106170641 A | 11/2016 |
| CN | 106352034 A | 1/2017 |
| CN | 205859041 U | 1/2017 |
| CN | 106438881 A | 2/2017 |
| CN | 106763488 A | 5/2017 |
| CN | 106969092 A | 7/2017 |
| CN | 107191539 A | 9/2017 |
| CN | 206592477 U | 10/2017 |
| CN | 206770516 U | 12/2017 |
| CN | 206988367 U | 2/2018 |
| CN | 108087494 A | 5/2018 |
| CN | 207406705 U | 5/2018 |
| CN | 108180254 A | 6/2018 |
| CN | 108506433 A | 9/2018 |
| CN | 108996374 A | 12/2018 |
| CN | 109073041 A | 12/2018 |
| CN | 208237006 U | 12/2018 |
| CN | 208381203 U | 1/2019 |
| CN | 208381207 U | 1/2019 |
| CN | 208417402 U | 1/2019 |
| CN | 208457110 U | 2/2019 |
| CN | 208519118 U | 2/2019 |
| DE | 2726319 A1 | 12/1978 |
| DE | 2836030 A1 | 3/1979 |
| DE | 3542990 A1 | 6/1987 |
| DE | 3719009 A1 | 12/1988 |
| DE | 4101293 A1 | 10/1991 |
| DE | 10315636 A1 | 10/2004 |
| DE | 102011011500 A1 | 12/2011 |
| DK | 434583 A | 3/1985 |
| DK | 198304345 A | 3/1985 |
| EP | 0001518 A1 | 4/1979 |
| EP | 0011986 B1 | 12/1982 |
| EP | 0087969 A1 | 9/1983 |
| EP | 0125424 A1 | 11/1984 |
| EP | 0050174 B1 | 5/1985 |
| EP | 0151396 A2 | 8/1985 |
| EP | 0180143 A2 | 5/1986 |
| EP | 0201562 A1 | 11/1986 |
| EP | 0255333 A1 | 2/1988 |
| EP | 0278545 A1 | 8/1988 |
| EP | 0285406 A2 | 10/1988 |
| EP | 0316197 A1 | 5/1989 |
| EP | 0320698 A2 | 6/1989 |
| EP | 0327873 A1 | 8/1989 |
| EP | 0384049 A1 | 8/1990 |
| EP | 0398562 B1 | 11/1990 |
| EP | 0412453 B1 | 2/1991 |
| EP | 0482735 A2 | 4/1992 |
| EP | 0506490 A1 | 9/1992 |
| EP | 0571178 A1 | 11/1993 |
| EP | 0633408 A2 | 1/1995 |
| EP | 0677682 A1 | 10/1995 |
| EP | 0933094 A2 | 1/1998 |
| EP | 0847940 B1 | 5/1999 |
| EP | 0529053 B1 | 1/2000 |
| EP | 0697225 B1 | 5/2000 |
| EP | 0928757 B1 | 4/2002 |
| EP | 0917692 B1 | 9/2002 |
| EP | 1239184 A2 | 9/2002 |
| EP | 1190616 B1 | 12/2002 |
| EP | 1026038 B1 | 9/2004 |
| EP | 1660004 A2 | 5/2006 |
| EP | 1391222 B1 | 10/2006 |
| EP | 1749705 A2 | 2/2007 |
| EP | 1452770 B1 | 9/2007 |
| EP | 1837439 A2 | 9/2007 |
| EP | 0965670 B1 | 1/2008 |
| EP | 1929179 A1 | 6/2008 |
| EP | 2159448 A1 | 3/2010 |
| EP | 2163424 A1 | 3/2010 |
| EP | 2489899 A1 | 8/2012 |
| EP | 1481702 B1 | 9/2012 |
| EP | 1740247 B1 | 9/2012 |
| EP | 1787670 B1 | 10/2012 |
| EP | 2605993 A1 | 6/2013 |
| EP | 2101855 B1 | 8/2013 |
| EP | 2621572 A1 | 8/2013 |
| EP | 2670491 A2 | 12/2013 |
| EP | 2051760 B1 | 3/2014 |
| EP | 2717954 A1 | 4/2014 |
| EP | 1623745 B1 | 7/2014 |
| EP | 2425868 B1 | 11/2014 |
| EP | 2846064 A1 | 3/2015 |
| EP | 2894115 A1 | 7/2015 |
| EP | 2519295 B1 | 9/2015 |
| EP | 2717806 B1 | 9/2015 |
| EP | 2928532 A1 | 10/2015 |
| EP | 2428240 B1 | 2/2016 |
| EP | 2481435 B1 | 2/2016 |
| EP | 2022528 B1 | 3/2016 |
| EP | 2046430 B1 | 4/2016 |
| EP | 2481434 B1 | 4/2016 |
| EP | 2428241 B1 | 7/2016 |
| EP | 3053621 A1 | 8/2016 |
| EP | 3085405 A1 | 10/2016 |
| EP | 2621573 B1 | 12/2016 |
| EP | 3130371 A1 | 2/2017 |
| EP | 3157601 A1 | 4/2017 |
| EP | 2723430 B1 | 7/2017 |
| EP | 1773195 B1 | 8/2017 |
| EP | 3231470 A1 | 10/2017 |
| EP | 3266482 A1 | 1/2018 |
| EP | 3034286 B1 | 5/2018 |
| EP | 3323458 A1 | 5/2018 |
| EP | 3235544 B1 | 8/2018 |
| EP | 1765443 B1 | 1/2019 |
| EP | 2828183 B1 | 3/2019 |
| EP | 2114500 B1 | 6/2019 |
| EP | 2844325 B1 | 11/2019 |
| EP | 2744554 A1 | 12/2019 |
| FR | 2394457 A1 | 1/1979 |
| FR | 2660039 A3 | 9/1991 |
| FR | 2861445 A1 | 4/2005 |
| GB | 190419761 A | 7/1905 |
| GB | 190826914 A | 7/1909 |
| GB | 191228764 A | 5/1913 |
| GB | 155079 A | 12/1920 |

(56) References Cited

FOREIGN PATENT DOCUMENTS

| | | |
|---|---|---|
| GB | 216224 A | 5/1924 |
| GB | 268133 A | 3/1927 |
| GB | 311747 A | 5/1929 |
| GB | 344485 A | 3/1931 |
| GB | 353777 A | 7/1931 |
| GB | 390005 A | 3/1933 |
| GB | 395932 A | 7/1933 |
| GB | 425152 A | 3/1935 |
| GB | 443649 A | 3/1936 |
| GB | 474843 A | 11/1937 |
| GB | 477368 A | 12/1937 |
| GB | 486401 A | 6/1938 |
| GB | 500525 A | 2/1939 |
| GB | 505229 A | 5/1939 |
| GB | 506795 A | 6/1939 |
| GB | 509048 A | 6/1939 |
| GB | 514910 A | 11/1939 |
| GB | 566171 A | 12/1944 |
| GB | 570861 A | 7/1945 |
| GB | 571283 A | 8/1945 |
| GB | 573704 A | 12/1945 |
| GB | 746711 A | 3/1956 |
| GB | 755865 A | 8/1956 |
| GB | 814268 A | 6/1959 |
| GB | 840638 A | 7/1960 |
| GB | 843810 A | 8/1960 |
| GB | 877472 A | 9/1961 |
| GB | 877473 A | 9/1961 |
| GB | 915886 A | 1/1963 |
| GB | 925067 A | 5/1963 |
| GB | 945622 A | 1/1964 |
| GB | 962714 A | 7/1964 |
| GB | 971939 A | 10/1964 |
| GB | 1095321 A | 12/1966 |
| GB | 1065362 A | 4/1967 |
| GB | 1073129 A | 6/1967 |
| GB | 1105267 A | 3/1968 |
| GB | 1197700 A | 7/1970 |
| GB | 1215682 A | 12/1970 |
| GB | 1229390 A | 4/1971 |
| GB | 1265008 A | 3/1972 |
| GB | 1294104 A | 10/1972 |
| GB | 1357935 A | 6/1974 |
| GB | 1364838 A | 8/1974 |
| GB | 1369198 A | 10/1974 |
| GB | 1369199 A | 10/1974 |
| GB | 1369348 A | 10/1974 |
| GB | 1380573 A | 1/1975 |
| GB | 1400431 A | 7/1975 |
| GB | 1427985 A | 3/1976 |
| GB | 1483216 A | 8/1977 |
| GB | 1492009 A | 11/1977 |
| GB | 1498893 A | 1/1978 |
| GB | 1499105 A | 1/1978 |
| GB | 2011577 A | 7/1979 |
| GB | 2024605 A | 1/1980 |
| GB | 1603557 A | 11/1981 |
| GB | 2092704 A | 8/1982 |
| GB | 2116287 A | 9/1983 |
| GB | 2155134 A | 9/1985 |
| GB | 2194207 A | 3/1988 |
| GB | 2218726 A | 11/1989 |
| GB | 2266614 A | 11/1993 |
| GB | 2266671 A | 11/1993 |
| GB | 2373777 A | 10/2002 |
| GB | 2439152 A | 12/2007 |
| GB | 2467122 A | 7/2010 |
| GB | 2475044 A | 5/2011 |
| GB | 2500860 A | 10/2013 |
| GB | 2529238 A | 2/2016 |
| GB | 2540153 B | 10/2018 |
| IT | 1117812 B | 2/1986 |
| JP | S51151844 U | 12/1976 |
| JP | S52160041 U | 12/1977 |
| JP | S55119441 U | 9/1980 |
| JP | S55152945 A | 11/1980 |
| JP | S55161948 U | 12/1980 |
| JP | S55175650 U | 12/1980 |
| JP | S564057 U | 1/1981 |
| JP | S5683635 A | 7/1981 |
| JP | S5684146 U | 7/1981 |
| JP | S5689057 U | 7/1981 |
| JP | S56109939 A | 8/1981 |
| JP | S56141245 U | 10/1981 |
| JP | S56167955 A | 12/1981 |
| JP | S5723451 U | 2/1982 |
| JP | S5794153 A | 6/1982 |
| JP | S58106642 U | 7/1983 |
| JP | S58134249 A | 8/1983 |
| JP | S58169244 U | 10/1983 |
| JP | S58184338 A | 10/1983 |
| JP | S58187637 A | 11/1983 |
| JP | S58220720 A | 12/1983 |
| JP | S5945346 U | 3/1984 |
| JP | S5977146 A | 5/1984 |
| JP | S6040846 U | 3/1985 |
| JP | S6095233 A | 5/1985 |
| JP | S60113843 A | 6/1985 |
| JP | S60234172 A | 11/1985 |
| JP | H0126928 Y2 | 2/1986 |
| JP | S61127942 A | 6/1986 |
| JP | S6280321 A | 4/1987 |
| JP | S62159857 A | 7/1987 |
| JP | S636246 A | 1/1988 |
| JP | H0159888 B2 | 12/1989 |
| JP | H01307544 A | 12/1989 |
| JP | H0221046 A | 1/1990 |
| JP | H0242230 A | 2/1990 |
| JP | H0269225 A | 3/1990 |
| JP | H0299236 A | 4/1990 |
| JP | H02122910 A | 5/1990 |
| JP | H02199339 A | 8/1990 |
| JP | H0248773 B2 | 10/1990 |
| JP | H02248740 A | 10/1990 |
| JP | H0362536 B2 | 9/1991 |
| JP | H0449076 A | 2/1992 |
| JP | H0513821 B2 | 2/1993 |
| JP | H0557457 B2 | 8/1993 |
| JP | H0562656 B2 | 9/1993 |
| JP | H0650398 A | 2/1994 |
| JP | H0627528 B2 | 4/1994 |
| JP | H0630548 U | 4/1994 |
| JP | H0694081 A | 4/1994 |
| JP | H0640503 U | 5/1994 |
| JP | H06123333 A | 5/1994 |
| JP | H0665650 U | 9/1994 |
| JP | H0640352 Y2 | 10/1994 |
| JP | H06328590 A | 11/1994 |
| JP | H074469 A | 1/1995 |
| JP | H07243483 A | 9/1995 |
| JP | 2500290 B2 | 5/1996 |
| JP | 2516855 B2 | 7/1996 |
| JP | 2534192 B2 | 9/1996 |
| JP | 2566319 B2 | 12/1996 |
| JP | H08326851 A | 12/1996 |
| JP | H0942381 A | 2/1997 |
| JP | H09257103 A | 9/1997 |
| JP | H09329205 A | 12/1997 |
| JP | H1078086 A | 3/1998 |
| JP | H10132031 A | 5/1998 |
| JP | H10132061 A | 5/1998 |
| JP | H10141446 A | 5/1998 |
| JP | H10153239 A | 6/1998 |
| JP | H10153243 A | 6/1998 |
| JP | H10205584 A | 8/1998 |
| JP | H10213183 A | 8/1998 |
| JP | 2802039 B2 | 9/1998 |
| JP | H10235742 A | 9/1998 |
| JP | H10311390 A | 11/1998 |
| JP | H10318336 A | 12/1998 |
| JP | H11132291 A | 5/1999 |
| JP | H11166596 A | 6/1999 |
| JP | 2002-098195 A | 4/2002 |
| JP | 2002-098196 A | 4/2002 |

(56)　　　　References Cited

FOREIGN PATENT DOCUMENTS

| | | |
|---|---|---|
| JP | 2002-098201 A | 4/2002 |
| JP | 2002-098202 A | 4/2002 |
| JP | 2004-225749 A | 8/2004 |
| JP | 3143503 U | 7/2008 |
| JP | 2014-516601 | 7/2014 |
| JP | 2014-521471 | 8/2014 |
| JP | 2016-517765 A | 6/2016 |
| JP | 2016-124160 A | 7/2016 |
| JP | 2016-135213 A | 7/2016 |
| JP | 2016-183707 A | 10/2016 |
| JP | 2016-183779 A | 10/2016 |
| JP | 6159907 B1 | 7/2017 |
| JP | WO2016/047052 A1 | 7/2017 |
| JP | 2017-177545 A | 10/2017 |
| JP | 2018-025296 A | 2/2018 |
| JP | 2017-082377 A | 6/2018 |
| JP | 6371763 B2 | 8/2018 |
| JP | 2018-146048 A | 9/2018 |
| JP | 2018-170841 A | 11/2018 |
| JP | 2018-185040 A | 11/2018 |
| JP | 2018-193710 A | 12/2018 |
| JP | 2018-197496 A | 12/2018 |
| JP | 2019-011861 A | 1/2019 |
| KR | 10-0505555 | 11/2005 |
| KR | 10-0655193 | 12/2006 |
| KR | 10-0735214 | 7/2007 |
| KR | 10-2007-0104332 | 10/2007 |
| KR | 10-2013-0035156 | 4/2013 |
| KR | 10-1265565 | 5/2013 |
| KR | 10-2013-0138733 | 12/2013 |
| KR | 10-1399680 | 5/2014 |
| KR | 10-1454053 | 10/2014 |
| KR | 10-1476013 | 12/2014 |
| KR | 10-1495453 | 2/2015 |
| KR | 10-2017-0063917 A | 6/2017 |
| KR | 10-2018-0029646 | 3/2018 |
| KR | 10-2018-0137524 | 12/2018 |
| KR | 10-1927274 | 12/2018 |
| KR | 10-1933204 | 12/2018 |
| NZ | 552296 | 11/2010 |
| NZ | 550423 | 1/2011 |
| NZ | 551715 | 2/2011 |
| NZ | 567432 | 3/2012 |
| NZ | 587820 | 3/2012 |
| NZ | 583929 | 4/2012 |
| NZ | 580173 | 6/2012 |
| NZ | 575405 | 9/2012 |
| NZ | 595133 | 6/2013 |
| NZ | 597302 | 8/2013 |
| NZ | 599372 | 10/2013 |
| NZ | 596570 | 2/2014 |
| NZ | 596802 | 2/2014 |
| NZ | 607679 | 7/2014 |
| NZ | 608551 | 10/2014 |
| NZ | 607879 | 11/2014 |
| NZ | 612086 | 12/2014 |
| NZ | 610731 | 2/2015 |
| NZ | 610755 | 3/2015 |
| NZ | 615330 | 3/2015 |
| NZ | 618892 | 7/2015 |
| NZ | 701074 | 10/2015 |
| NZ | 701501 | 10/2015 |
| NZ | 625429 | 12/2015 |
| NZ | 630741 | 3/2016 |
| NZ | 702644 | 6/2016 |
| NZ | 701722 | 7/2016 |
| NZ | 700217 | 11/2016 |
| NZ | 709784 | 2/2017 |
| NZ | 713055 | 4/2017 |
| NZ | 713455 | 4/2017 |
| NZ | 714595 | 6/2017 |
| NZ | 720629 | 12/2017 |
| NZ | 721025 | 1/2018 |
| NZ | 727624 | 7/2018 |
| NZ | 728600 | 10/2018 |
| NZ | 730762 | 10/2018 |
| NZ | 732004 | 11/2018 |
| NZ | 736962 | 5/2019 |
| NZ | 738046 | 6/2019 |
| NZ | 739208 | 7/2019 |
| PL | 201840 B1 | 5/2009 |
| RU | 2141979 C1 | 11/1999 |
| RU | 2253773 C1 | 6/2005 |
| RU | 92605 U1 | 3/2010 |
| RU | 125225 U1 | 2/2013 |
| RU | 159556 U1 | 2/2016 |
| RU | 2015117275 A | 11/2016 |
| RU | 172161 U1 | 6/2017 |
| TW | 201007027 A | 2/2010 |
| TW | 201114647 A | 5/2011 |
| TW | 201328933 | 7/2013 |
| TW | 201343213 A | 11/2013 |
| WO | WO 1985/004844 | 11/1985 |
| WO | WO 1988/003036 | 5/1988 |
| WO | WO 1993/018813 | 9/1993 |
| WO | WO 1995/016865 | 6/1995 |
| WO | WO 1996/000181 | 1/1996 |
| WO | WO 2000/053389 | 9/2000 |
| WO | WO 2000/074612 | 12/2000 |
| WO | WO 2001/075834 | 10/2001 |
| WO | WO 2003/026808 | 4/2003 |
| WO | WO 2003/066145 | 8/2003 |
| WO | WO 2004/028897 | 4/2004 |
| WO | WO 2004/030723 | 4/2004 |
| WO | WO 2005/065480 | 7/2005 |
| WO | WO 2005/075732 | 8/2005 |
| WO | WO 2005/075736 | 8/2005 |
| WO | WO 2005/076874 | 8/2005 |
| WO | WO 2005/079726 | 9/2005 |
| WO | WO 2005/099801 | 10/2005 |
| WO | WO 2006/111875 | 10/2006 |
| WO | WO 2006/114327 | 11/2006 |
| WO | WO 2007/019624 | 2/2007 |
| WO | WO 2007/036959 | 4/2007 |
| WO | WO 2007/041786 | 4/2007 |
| WO | WO 2007/124966 | 11/2007 |
| WO | WO 2007/139890 | 12/2007 |
| WO | WO 2007/142318 | 12/2007 |
| WO | WO 2008/011683 | 1/2008 |
| WO | WO 2008/040050 | 4/2008 |
| WO | WO 2008/078558 | 7/2008 |
| WO | WO 2008/100150 | 8/2008 |
| WO | WO 2008/102459 | 8/2008 |
| WO | WO 2008/106716 | 9/2008 |
| WO | WO 2008/117695 | 10/2008 |
| WO | WO 2008/142766 | 11/2008 |
| WO | WO 2009/003137 | 12/2008 |
| WO | WO 2009/011344 | 1/2009 |
| WO | WO 2009/109005 | 9/2009 |
| WO | WO 2010/021645 | 2/2010 |
| WO | WO 2010/035645 | 4/2010 |
| WO | WO 2010/047051 | 4/2010 |
| WO | WO 2010/061599 | 6/2010 |
| WO | WO 2010/131189 | 11/2010 |
| WO | WO 2010/139087 | 12/2010 |
| WO | WO 2011/019582 | 2/2011 |
| WO | WO 2011/077274 | 6/2011 |
| WO | WO 2011/078703 | 6/2011 |
| WO | WO 2011/085427 | 7/2011 |
| WO | WO 2012/040791 | 4/2012 |
| WO | WO 2012/040792 | 4/2012 |
| WO | WO 2012/066984 | 5/2012 |
| WO | WO 2012/132567 | 10/2012 |
| WO | WO 2012/133922 | 10/2012 |
| WO | WO 2012/174602 | 12/2012 |
| WO | WO 2013/022356 A1 | 2/2013 |
| WO | WO 2013/061538 | 5/2013 |
| WO | WO 2013/088439 A1 | 6/2013 |
| WO | WO 2013/163685 | 11/2013 |
| WO | WO 2014/015382 | 1/2014 |
| WO | WO 2014/025591 | 2/2014 |
| WO | WO 2014/069588 | 5/2014 |
| WO | 2014/083594 A1 | 6/2014 |
| WO | WO 2014/089506 | 6/2014 |

(56) References Cited

FOREIGN PATENT DOCUMENTS

| WO | WO 2014/138804 | 9/2014 |
|----|----------------|--------|
| WO | WO 2014/142681 | 9/2014 |
| WO | WO 2014/169241 | 10/2014 |
| WO | WO 2014/208628 | 12/2014 |
| WO | WO 2015/005055 | 1/2015 |
| WO | WO 2015/025318 | 2/2015 |
| WO | WO 2015/029840 | 3/2015 |
| WO | WO 2015/031349 | 3/2015 |
| WO | WO 2015/034942 | 3/2015 |
| WO | WO 2015/043119 | 4/2015 |
| WO | WO 2015/043229 | 4/2015 |
| WO | WO 2015/106726 | 7/2015 |
| WO | WO 2015/122113 | 8/2015 |
| WO | WO 2015/178391 | 11/2015 |
| WO | WO 2015/178615 | 11/2015 |
| WO | WO 2015/192186 | 12/2015 |
| WO | WO 2016/024373 | 2/2016 |
| WO | WO 2016/044881 | 3/2016 |
| WO | WO 2016/046776 | 3/2016 |
| WO | WO 2016/051160 | 4/2016 |
| WO | WO 2016/114079 | 7/2016 |
| WO | WO 2016/157105 | 10/2016 |
| WO | WO 2016/203211 | 12/2016 |
| WO | WO 2017/073647 | 5/2017 |
| WO | WO 2017/110784 | 6/2017 |
| WO | WO 2017/110790 | 6/2017 |
| WO | WO 2017/121662 | 7/2017 |
| WO | WO 2017/150990 | 9/2017 |
| WO | WO 2017/158476 | 9/2017 |
| WO | WO 2017/168920 | 10/2017 |
| WO | WO 2017/182987 | 10/2017 |
| WO | WO 2017/185140 | 11/2017 |
| WO | WO 2017/204207 | 11/2017 |
| WO | WO 2017/204250 | 11/2017 |
| WO | WO 2017/206104 | 12/2017 |
| WO | WO 2017/213297 | 12/2017 |
| WO | WO 2018/008204 | 1/2018 |
| WO | WO 2018/017209 | 1/2018 |
| WO | WO 2018/021454 | 2/2018 |
| WO | WO 2018/025853 | 2/2018 |
| WO | WO 2018/029638 | 2/2018 |
| WO | WO 2018/029689 | 2/2018 |
| WO | WO 2018/042376 | 3/2018 |
| WO | WO 2018/085951 | 5/2018 |
| WO | WO 2018/124889 | 7/2018 |
| WO | WO 2018/134767 | 7/2018 |
| WO | WO 2018/155722 | 8/2018 |
| WO | WO 2018/159627 | 9/2018 |
| WO | WO 2018/179636 | 10/2018 |
| WO | WO 2018/198657 | 11/2018 |
| WO | WO 2018/202952 | 11/2018 |
| WO | WO 2018/204969 | 11/2018 |
| WO | WO 2019/042486 | 3/2019 |

OTHER PUBLICATIONS

U.S. Appl. No. 60/808,034, filed May 23, 2006, Doshi et al.
Australian Examination Report in Application No. 2016241572, dated Feb. 15, 2021, in 4 pages.
European Supplemental Search Report for Application No. EP 16 77 1501, dated Oct. 9, 2018 in 7 pages.
Extended European Search Report for Application No. 17838905.2 dated Mar. 2, 2020 in 4 pages.
International Search Report, PCT/IB2017/054896; Dec. 18, 2017; 12 pages.
International Search Report for Application No. PCT/IB2016/051819, mailed Jun. 29, 2016 in 7 pages.
International Search Report & Written Opinion for Application No. PCT/2019/051137 dated Jun. 4, 2019, in 22 pages.
Japanese Examination Report in Application No. 2017-551052, dated Oct. 1, 2020 in 5 pages.
United Kingdom Examination Report in Application No. GB1715236. 4, dated Mar. 26, 2020, in 3 pages.
United Kingdom Examination Report in Application No. GB1715236. 4, dated Oct. 20, 2020, in 1 page.
European Search Report for Application No. 16771501.0 dated May 25, 2020, 4 pages.

* cited by examiner

Upper Respiratory Region

Lower Respiratory Region

712

713

710

112

707

710

712

711

703, 705

702

708

711

704

701

700

700

700

700

713

20°

924

943

903

902

901

902

904

924

906

941

942

926

952

935

941

943

942

954

951

950

925

112

COLLAPSIBLE CONDUIT, PATIENT INTERFACE AND HEADGEAR CONNECTOR

TECHNICAL FIELD

This disclosure relates to various patient interfaces and particularly to patient interfaces for use with a high flow system. The patient interfaces include deliberately collapsible features to facilitate the stopping of gas flow through the patient interface and/or allow a face mask to be used over the patient interface while positioned on a user's face. The disclosure also relates to headgear connectors, and to breathing conduits with a collapsible portion.

BACKGROUND ART

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation and $CO_2$ flushing/washout may be carried out with a high flow therapy via a nasal cannula or other patient interface.

Once under general anaesthesia, patients must be intubated to ventilate the patient. In some cases, intubation is completed in 30 to 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and increase the patient's oxygen saturation to adequate levels. The interruption of the intubation process may happen several times for difficult intubation processes, which is time consuming and puts the patient at severe health risk. After approximately three attempts at intubation the medical procedure, such as an intubation method will be abandoned.

In the event that manual ventilation of the apnoeic, non-intubated, patient is urgently required (such as due to unsuccessful intubation of the patient) it is necessary to quickly remove the high flow patient interface and then apply a non-invasive ventilation mask, e.g. a face mask and bag, to the patient. A cannula may be difficult to remove quickly from the patient, for example connectors between headgear and a cannula may be difficult to release quickly or manipulate with one hand. Failure to remove the patient interface may result in the cushion of the face mask overlying the patient interface or patient interface gases supply tube, disrupting the seal between the face mask and the patient's face. Gases may consequently leak from the face mask during ventilation, rendering ventilation ineffective or inefficient.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

SUMMARY

It is an object of this disclosure to provide a breathing conduit or a patient interface or a headgear connector which goes at least some way towards overcoming one or more of the above mentioned problems or difficulties, or to provide the industry/public with a useful choice.

In accordance with at least one of the embodiments disclosed herein, a breathing conduit for providing a flow of respiratory gases, whether formed with a patient interface or as a separate conduit, comprises a collapsible portion, a lateral cross section of the collapsible portion comprising:

a first side comprising a flat portion for positioning against a user's face, a second side opposite the first side and facing away from the user's face, the first and second sides joined by first and second fold points, in an open configuration the fold points spaced away from the flat portion of the first side in a direction away from the user's face in use, wherein an inner length of the first side between the fold points and an inner length of the second side between the fold points are substantially equal, and in a partially closed or closed configuration the second side being moved towards or against the first side with the collapsible portion folding at the first and second fold points.

In some embodiments, the first side comprises an outwardly curved portion between the flat portion and each of the first and second fold points when in the open configuration.

In some embodiments, the thickness of the outwardly curved portion tapers from the flat portion towards the respective fold point, from a greater thickness to a reduced thickness.

In some embodiments, the first side is curved outwardly when in the open configuration.

In some embodiments, the second side is curved outwardly when in the open configuration.

In some embodiments, in the closed configuration the fold points are moved to be against or adjacent the face of a user.

In some embodiments, the thickness of the first side and/or the second side tapers towards each fold point, from a greater thickness to a reduced thickness.

In some embodiments, a maximum thickness of the first side is at an apex of the first side and/or a maximum thickness of the second side is at an apex of the second side.

In some embodiments, the thickness of the fold points is less than the thickness of the remainder of the cross section of the collapsible portion.

In some embodiments, the second side is thinner than the first side.

In some embodiments, in the open configuration the first side adjacent each fold point is at an angle to the flat portion such that an external angle between the first side adjacent the fold point and the flat portion is less than 80 degrees, or less than 75 degrees, or less than 70 degrees, or less than 65 degrees, or less than 60 degrees, or less than 55 degrees, or less than 50 degrees, or less than 45 degrees, or less than 40 degrees, or less than 35 degrees, or less than 30 degrees, or is between 50 and 70 degrees, or is between 60 and 70 degrees, or about 62 to 68 degrees, or is about 64 to 66 degrees, or is about 65 degrees.

In some embodiments, in the open configuration a line tangential to the portion of the first side adjacent to each folding point is an angle to a line extending between the first and second fold points such that an angle (beta) between the line and the portion adjacent the fold point is less than 70 degrees, or less than 65 degrees, or less than 60 degrees, or less than 55 degrees, or less than 50 degrees, or less than 45 degrees, or less than 40 degrees, or less than 35 degrees, or less than 30 degrees, or is between 30 and 60 degrees, or is between 40 and 50 degrees, or may be about 45 degrees.

In some embodiments, the flat portion has a thickness of about 0.5 mm, and the fold points have a thickness of about 0.2 mm.

In some embodiments, the flat portion has a length of about 5 mm to 10 mm or about 7 mm, and/or wherein a lateral width of the cross section of the collapsible portion is between 10 mm and 15 mm or about 13 mm.

In some embodiments, the first side tapers from a thickness of 0.5 mm to a thinner thickness at the fold point.

In some embodiments, the ratio of:

i) the thickness of the (thicker) centre of the first and/or second sides of the lateral cross section and thickness of the (thinner) fold points is in the range of about 1 to 8, or about 1.5 to 3.5, or ii) the thickest part of the lateral cross section to the thinnest part of the lateral cross section being the fold points is in the range of about 1 to 8, or about 1.5 to 3.5

In some embodiments, the ratio of the relative thicknesses between the (thicker) flat portion of the first side and the (thinner) fold points is in the range of about 1 to 8, or about 1.5 to 3.5.

In some embodiments, the first and second fold points delimit or define the extent of the first and second sides, or the first and second sides each extend fully between the fold points, e.g. from the first fold point to the second fold point.

In some embodiments, the collapsible section has reflective symmetry about a centre line of the cross section, the centre line extending through a centre of the first and second sides of the cross section.

In some embodiments, a distance between the fold points is greater than a width of the flat portion.

In some embodiments, a maximum width of the cross section is defined by a distance between the fold points.

In some embodiments, the first and second sides are curved outwardly, the lateral cross section being substantially oval or elliptical but with the first and second sides converging to a point at each fold point.

In some embodiments, the first side diverges outwardly either side of the flat portion towards the respective fold point.

In some embodiments, the conduit is a conduit portion of a patient interface.

In some embodiments, the patient interface is a nasal interface.

In some embodiments, the nasal interface is a nasal cannula.

In some embodiments, the collapsible portion is formed from an elastomeric/resilient material, for example silicone.

In accordance with at least one of the embodiments disclosed herein, a breathing conduit for providing a flow of respiratory gases, whether formed with a patient interface or as a separate conduit, comprises a collapsible portion, a lateral cross section of the collapsible portion comprising:

a first side for positioning against a user's face, a second side opposite the first side to face away from the user's face, the first and second sides joined by first and second fold points, the conduit adapted to collapse from an open configuration to a closed configuration by folding at the fold points so that the first side and the second side are positioned in contact or adjacent each other to substantially occlude flow through the conduit when in the closed configuration.

In some embodiments, an inner length of the first side between the fold points and an inner length of the second side between the fold points are substantially equal.

In some embodiments, the lateral cross section has reflective symmetry about a line extending through the first and second fold points.

In some embodiments, the lateral cross section has reflective symmetry about a centre line of the cross section, the centre line extending through a centre of the first and second sides of the cross section.

In some embodiments, the second side is curved outwardly when in the open configuration.

In some embodiments, the first side is curved outwardly when in the open configuration.

In some embodiments, in the closed configuration the fold points are moved to be against or adjacent the face of a user.

In some embodiments, the thickness of the first side and/or the second side tapers towards each fold point, from a greater thickness to a reduced thickness, the maximum thickness being at an apex of each of the first side and second side respectively.

In some embodiments, the thickness of the fold points is less than the thickness of the remainder of the cross section of the collapsible portion.

In some embodiments, the second side is thinner than the first side.

In some embodiments, the ratio of:

i) the thickness of the (thicker) centre of the first and/or second sides of the lateral cross section and the thickness of the (thinner) fold points is in the range of about 1 to 8, or about 1.5 to 3.5, or ii) the thickest part of the lateral cross section to the thinnest part of the lateral cross section being the fold points is in the range of about 1 to 8, or about 1.5 to 3.5.

In some embodiments, in the open configuration a line tangential to the portion of the first side adjacent to each folding point is an angle to a line extending between the first and second fold points such that an angle (beta) between the line and the portion adjacent the fold point is less than 70 degrees, or less than 65 degrees, or less than 60 degrees, or less than 55 degrees, or less than 50 degrees, or less than 45 degrees, or less than 40 degrees, or less than 35 degrees, or less than 30 degrees, or is about 30 to 60 degrees, or about 40 to 50 degrees, or may be about 45 degrees.

In some embodiments, the first and second fold points delimit or define the extent of the first and second sides, or the first and second sides each extend fully between the fold points, e.g. from the first fold point to the second fold point.

In some embodiments, a maximum width of the cross section is defined by a distance between the fold points.

In some embodiments, the first and second sides are curved outwardly, the lateral cross section being substantially oval or elliptical but with the first and second sides converging to a point at each fold point.

In some embodiments, the conduit is a conduit portion of a patient interface.

In some embodiments, the patient interface is a nasal interface.

In some embodiments, the nasal interface is a nasal cannula.

In some embodiments, the collapsible portion is formed from an elastomeric/resilient material, for example silicone.

In accordance with at least one of the embodiments disclosed herein, a breathing conduit for providing a flow of respiratory gases, whether formed with a patient interface or as a separate conduit, comprises a collapsible portion, a lateral cross section of the collapsible portion being substantially rhombus or parallelogram shaped, the four corners of the rhombus or parallelogram shaped cross section providing fold points, in an open configuration the four sides of the rhombus or parallelogram spaced apart, and in a closed configuration the cross section folding at the corners so that adjacent sides of the rhombus or parallelogram come together into contact and with the corners comprising acute internal angles located at edges of the cross section.

In some embodiments, the lateral cross section of the collapsible portion being substantially parallelogram shaped and adapted such that a long side of the parallelogram is located against a user's face in use.

In some embodiments, an acute angle of the rhombus or parallelogram is less than 70 degrees, or less than 65 degrees, or less than 60 degrees, or less than 55 degrees, or less than 50 degrees, or less than 45 degrees, or less than 40 degrees, or less than 35 degrees, or less than 30 degrees, or is between 45 and 65 degrees, or is between 55 and 65 degrees, or may be about 60 degrees.

In some embodiments, the thickness of the sides of the rhombus or parallelogram taper towards each corner (fold point) with an acute angle, from a greater thickness to a reduced thickness.

In some embodiments, the thickness of the corners (fold points) comprising an acute angle is less than the thickness of the sides or a remainder of the cross section of the collapsible portion.

In some embodiments, a side of the rhombus or parallelogram shaped cross section for locating against a user's face is thicker than other sides of the rhombus or parallelogram shaped cross section.

In some embodiments, the ratio of:
i) the relative thicknesses between the (thicker) sides of the lateral cross section and the (thinner) fold points is in the range of about 1 to 8, or about 1.5 to 3.5, or
ii) the thickest part of the lateral cross section to the thinnest part of the lateral cross section being the fold points is in the range of about 1 to 8, or about 1.5 to 3.5.

In some embodiments, the cross section comprises an internal notch at the corners comprising an acute angle so that the thickness at the corners comprising an acute angle is less than the thickness of the sides of the cross section.

In some embodiments, the sides of the rhombus or parallelogram have a thickness of about 0.5 mm, and wherein the corners comprising an acute angle have a thickness of about 0.2 mm.

In some embodiments, the cross section of the collapsible portion comprises a tail portion extending from one or both corners of the section comprising acute internal angles, each tail portion providing a ramp from the edge of the section onto a top of the section in the closed configuration.

In some embodiments, a side of the rhombus or parallelogram shaped cross section for locating against a user's face is thicker than other sides of the rhombus or parallelogram shaped cross section, and
the cross section comprises only one tail portion that extends from the corner of the cross section comprising an acute angle at the thicker side of the cross section.

In some embodiments, the thickness of the sides of the cross section taper to be thicker at at least one corner of the cross section comprising an obtuse angle.

In some embodiments, the thickness of the cross section provides for a tapering collapsed cross section that tapers in thickness from the edges of the cross section to a thicker section between the edges of the collapsed cross section.

In some embodiments, the cross section has reflective symmetry on a line extending through the corners comprising an obtuse angle.

In some embodiments, the conduit is a conduit portion of a patient interface.

In some embodiments, the patient interface is a nasal interface.

In some embodiments, the nasal interface is a nasal cannula.

In some embodiments, the collapsible portion is formed from an elastomeric/resilient material, for example silicone.

In accordance with at least one of the embodiments disclosed herein, a patient interface comprises a breathing conduit as described in any one or more of the above statements.

In some embodiments, the interface is a nasal interface comprising a single inlet, at least one nasal outlet, and the breathing conduit extending between the single inlet and the at least one nasal outlet.

In accordance with at least one of the embodiments disclosed herein, a connector adapted to connect a headgear to a patient interface comprises:
a first connector part (e.g. a male part) and a second connector part (e.g. a female part), the second connector part comprising a pair of spaced apart tines to receive the first part therebetween when the first and second parts are connected together.

In some embodiments, the tines each extend from a base of the second part, an end of each tine distal from the base free to deflect laterally relative to the base.

In some embodiments, one or both of the tines comprises an aperture or a lateral projection, and the first part comprises a corresponding lateral projection or aperture, such that with the first part received between the tines the lateral projection is received in the aperture to retain the first and second parts together.

In some embodiments, the aperture is a slot oriented with a major axis lateral to a longitudinal axis of a headgear strap to be attached to the patient interface.

In some embodiments, each tine comprises a said aperture and the first connector comprises a said lateral projection on each lateral side of the first part.

In some embodiments, the first and second parts are complementarily adapted to rotate relative to one another from a engaged position to disengage, the first and second parts comprising complementary features such that relative rotation between the first and second parts causes the tines to deflect and spread apart to release the second part from the first part.

In some embodiments, the aperture and projection are complementarily adapted so that relative rotation between the first and second parts causes the projection to release from the aperture and deflect a said tine over the projection.

In some embodiments, the lateral projection comprising a bevelled edge to deflect the tines apart when inserting the first part in between the tines of the second part in an axial direction of the connector parts.

In some embodiments, the second connector part is releasably coupled to a headgear.

In accordance with at least one of the embodiments disclosed herein, a connector adapted to connect a headgear to a patient interface comprises:
a first connector part (e.g. a male part) and a complementary second connector part (e.g. a female part) comprising a pair of spaced apart resilient tines to receive the first connector part therebetween, the second connector part adapted to be removably coupled to a headgear, the second connector part comprising a base, each tine extending from the base, and an end of each tine distal from the base free to deflect laterally relative to the base so that the tines deflect laterally apart to release the first connector part from the second connector part.

In some embodiments, the first and second connector parts are adapted to be connected together by moving the second connector part axially towards the first connector part, and the connector parts adapted to be disconnected by relative rotation about a lateral projection on one of the first and second parts received in an aperture on the other one of the first and second parts.

In accordance with at least one of the embodiments disclosed herein, a patient interface comprises:

a manifold and at least one nasal prong or an outlet extending from the manifold to be received by a user's nare or mouth, a side member extending from each side of the manifold, each side member comprising a collapsible portion comprising a lumen, in an open configuration the lumen remaining open and the collapsible portion adapted to be pinched or flattened to a closed configuration (e.g. by an external force) to occlude or substantially occlude the lumen, and wherein at least one of the side members is a conduit for a flow of gases from an inlet of the patient interface to the manifold.

In some embodiments, the patient interface comprises a plug and a conduit connector, the plug adapted to fit to an end of one or both side members, and the conduit connector adapted to fit to an end of the other one or both side members.

In some embodiments, each side member is formed as a conduit, and the patient interface comprises a plug and a conduit connector, the plug and conduit connector both adapted to fit to an inlet end of both side members, so that the patient interface is configurable to a dual inlet patient interface or a left or right sided single patient interface.

In some embodiments, the patient interface comprises a wall near to and on an inlet side of a said nasal prong or outlet, to separate the lumen of one side member from the manifold and the other side member, such that only one of the side members acts as a conduit to provide a flow of gases from an inlet of the patient interface to the manifold.

In some embodiments, the lumen of the side member that is separate from the manifold comprises a relief hole so that the lumen of the side arm separate from the manifold is in communication with the atmosphere.

In some embodiments, the wall is curved or shaped to direct a flow from the manifold to the at least one nasal prong or outlet and/or to reduce resistance to flow.

In some embodiments, the side members, manifold and the at least one nasal prong or outlet are integrally formed as a unitary member.

In some embodiments, the side members are formed from a relatively soft or compliant material and the plug and/or conduit connector is formed from a relatively rigid or hard material.

In some embodiments, the patient interface comprises a removable shield to configure the patient interface for use without collapsing.

In some embodiments, the shield is adapted to fit over and cover a side member, or both side members and the manifold.

In some embodiments, the shield comprises one or more pair of jaws, each pair of jaws configured to grab around a portion of the patient interface to hold the shield to the patient interface.

In some embodiments, the patient interface is a nasal cannula comprising the manifold and at least one said nasal prong or a nasal outlet extending from the manifold to be received by a user's nare.

In some embodiments, a part of a headgear connector is integrally formed with each side member.

In some embodiments, wherein a part of a headgear connector is integrally formed with the conduit connector and/or a part of a headgear connector is integrally formed with the plug.

In some embodiments, the cannula comprises a pair of headgear connector parts (e.g. a pair of male parts or a pair of female parts), each part adapted to connect to a corresponding headgear connector part to attach a headgear to the cannula, and wherein each headgear connector part is arranged at an angle to the side members in a side view of the cannula, so that in use the cannula is positioned horizontally on the user's face and with a headgear extending above the user's ears.

In some embodiments, the angle is 10 to 30 degrees, or 15 to 25 degrees, or about 20 degrees.

In some embodiments, in plan view the cannula comprises an obtuse angle between the side members when in a neutral or unbent configuration.

In some embodiments, the obtuse angle in the range of 100 to 130 degrees, or about 100 to 120 degrees, or about 100 to 110 degrees, or about 105 degrees (e.g. 106 degrees).

In some embodiments, the side members are substantially straight in a neutral or unbent configuration, and the manifold is curved to provide the obtuse angle between the side members.

In some embodiments, the cannula comprises a pair of headgear connector parts (e.g. a pair of male parts or a pair of female parts), each part adapted to connect to a corresponding headgear connector part to attach a headgear to the cannula, and wherein each headgear connector part is arranged at an angle to the side members in a plan view of the cannula, wherein the angle is in the range of 130 degrees to 170 degrees, or 140 degrees to 160 degrees, or 145 degrees to 155 degrees.

In some embodiments, the cannula comprises a pair of headgear connector parts (e.g. a pair of male parts or a pair of female parts), each part adapted to connect to a corresponding headgear connector part to attach a headgear to the cannula, and wherein a distance between distal ends of the side arms, or between the pair of headgear connector parts is about 100 mm to 150 mm, or about 110 mm to 140 mm, or about 110 mm to 130 mm or about 120 mm.

In accordance with at least one of the embodiments disclosed herein, a nasal cannula comprises:

a manifold and at least one nasal prong or outlet extending from the manifold to be received by a user's nare, and a side member extending from each side of the manifold, and wherein in plan view the cannula comprises an obtuse angle between the side members when in a neutral or unbent configuration.

In some embodiments, the obtuse angle in the range of 100 to 130 degrees, or about 100 to 120 degrees, or about 100 to 110 degrees, or about 105 degrees (e.g. 106 degrees).

In some embodiments, the side members are substantially straight in a neutral or unbent configuration, and the manifold is curved to provide the obtuse angle between the side members.

In some embodiments, the cannula comprises a pair of headgear connector parts (e.g. a pair of male parts or a pair of female parts), each part adapted to connect to a corresponding headgear connector part to attach a headgear to the cannula, and wherein each headgear connector part is arranged at an angle to the side members in a plan view of the cannula, wherein the angle is in the range of 130 degrees to 170 degrees, or 140 degrees to 160 degrees, or 145 degrees to 155 degrees.

In some embodiments, the cannula comprises a pair of headgear connector parts (e.g. a pair of male parts or a pair of female parts), each part adapted to connect to a corresponding headgear connector part to attach a headgear to the cannula, and wherein each headgear connector part is arranged at an angle to the side members in a side view of the cannula, so that in use the cannula is positioned horizontally on the user's face and with a headgear extending above the user's ears.

In some embodiments, the angle is 10 to 30 degrees, or 15 to 25 degrees, or about 20 degrees.

In some embodiments, the nasal cannula comprises a wall near to and on an inlet side of a said nasal prong or outlet, to separate the lumen of one side member from the manifold and the other side member, such that only one of the side members acts as a conduit to provide a flow of gases from an inlet of the cannula to the manifold.

In some embodiments, the lumen of the side member that is separate from the manifold comprises a relief hole so that the lumen of the side arm separate from the manifold is in communication with the atmosphere.

In accordance with at least one of the embodiments disclosed herein, a conduit for a respiratory support system comprises:

a collapsible portion, in an open configuration the collapsible portion remaining open and in a closed configuration the collapsible portion being pinched or flattened to occlude or substantially occlude the conduit, and a relatively rigid component adapted to move from a first configuration in which the collapsible portion is in the open configuration to a second configuration in which the component presses against an outside of the collapsible portion to pinch or flatten the collapsible portion into the closed configuration.

In some embodiments, the component comprises a shield attached to the outside of the collapsible portion, the shield adapted to distribute an external force applied to the shield to a predetermined collapsible area of the collapsible portion.

In some embodiments, the component comprises a lever adapted to pivot from the first configuration to the second configuration.

In some embodiments, the conduit comprises the collapsible portion and a non-collapsible portion and the lever is pivotally attached to the non-collapsible potion of the conduit.

In some embodiments, the conduit comprises a vent aperture upstream of the collapsible portion and wherein the lever comprises a first arm extending from a first side of a pivot and a second arm extending from an opposite second side of the pivot, and in the first configuration the lever is pivoted about the pivot so that the first arm does not pinch or flatten the collapsible portion and the second arm substantially occludes the vent aperture, and in the second configuration the lever is pivoted about the pivot so that the first arm pinches or flattens the collapsible portion and the second arm lifts away from the vent aperture to allow gases in the conduit upstream of the collapsible portion to vent to atmosphere.

In some embodiments, the vent aperture is in the non-collapsible portion of the conduit.

In some embodiments, the lever comprises a projection or rim to press against the collapsible portion in the second configuration.

In accordance with at least one of the embodiments disclosed herein a patient interface comprises:

an interface portion for interfacing with a user's nasal or oral airway, and a conduit as described in any one or more of the preceding statements, the conduit extending from the interface portion, and the relatively rigid component attached to the conduit or interface portion to move from the first configuration to the second configuration.

In some embodiments, the component comprises a lever pivotally attached to the conduit or interface portion to pivot from the first configuration to the second configuration.

In some embodiments, the conduit comprises the collapsible portion and a non-collapsible portion and the lever is pivotally attached to the non-collapsible potion of the conduit, and wherein the collapsible portion is located between the interface portion and the non-collapsible portion of the conduit.

In some embodiments, the patient interface is a nasal cannula and the interface portion comprises a manifold and at least one nasal prong or outlet extending from the manifold.

In some embodiments, the patient interface is an oral interface to be received in a user's mouth.

In accordance with at least one of the embodiments disclosed herein a patient interface comprises:

a body comprising:

a manifold and at least one nasal prong or an outlet extending from the manifold, and a left hand side member extending from a left side of the manifold and a right hand side member extending from a right side of the manifold, each side member comprising an inlet portion and a lumen to provide a conduit for a flow of gases from the inlet portion to the manifold, and a frame comprising a tube connector and a blanked hollow projection, the tube connector and the blanked hollow projection adapted to receive a said inlet portion of the body with the frame attached to the body, the frame movably attached to the body to selectively configure the patient interface between a left hand inlet configuration and a right hand inlet configuration, in the left hand inlet configuration the inlet portion of the left hand side member received in the tube connector and the inlet portion of the right hand side member received in the blanked hollow projection, and in the right hand inlet configuration the inlet portion of the right hand side member received in the tube connector and the inlet portion of the left hand side member received in the blanked hollow projection.

In some embodiments, the conduit of each side member comprises a collapsible portion, in an open configuration the collapsible portion remaining open and in a closed configuration the collapsible portion being pinched or flattened to occlude or substantially occlude the conduit.

In some embodiments, the frame is adapted to deform so that a force applied to the front of the frame elastically bends the frame to collapse the conduit of a said member to the closed configuration.

In some embodiments, the frame is rotationally attached to the body rotate the frame relative to the body to selectively configure the cannula between the left hand inlet configuration and the right hand inlet configuration.

In some embodiments, the frame comprises a concave interior to receive a correspondingly shaped convex shape of the body.

In some embodiments, the patient interface is a nasal cannula, said body being a cannula body comprising the manifold and said at least one nasal prong or a nasal outlet extending from the manifold to be received by a user's nare.

In accordance with at least one of the embodiments disclosed herein a patient interface comprises a headgear, the headgear comprising a pair of arms, each arm comprising an ear plug, each ear plug adapted to fit within a user's ear to retain the patient interface in position on the user's face.

In some embodiments, one or both arms is length adjustable

In some embodiments, one or both arms is telescopic, one or both arms comprising a first portion slidingly received in a second portion, relative movement between the first and second arms adjusting the length of the arm.

In some embodiments, one of the first and second portions of each arm is integrally formed with a frame attached to a body of the patient interface.

In some embodiments, one of the first and second portions of the arm is more rigid than the other one of the first and second portions of the arm.

In some embodiments, the patient interface is a nasal cannula.

The term 'conduit' as used in this specification and claims is intended to broadly mean, unless the context suggests otherwise, any member that forms or provides a lumen for directing a flow of gases. For example a conduit or conduit portion may be part of a patient interface or may be a separate conduit attachable to a patient interface to provide a flow of gases to the patient interface The phrase 'lateral cross section' of a conduit means a cross section transverse to the flow path of the conduit, e.g. perpendicular to a flow path or longitudinal axis of the conduit. As a further example, the lateral cross section may be viewed from an end of the conduit.

Unless the context suggests otherwise, the thickness of a side or a portion of a lateral cross section of a conduit is the lateral wall thickness of the side or portion of the cross section. For example, the thickness at a point (i.e. a fold point) on the cross section is the smallest distance across the wall of the cross section from an outer surface to an inner surface of the wall at that point. For example, in FIG. 6A, the thickness of a fold point 522 is the distance from the outside surface to the inside surface at the fold point 522, for example along a line extending through a centre of the cross section, or a line extending across the cross section extending through both fold points 522 of the cross section.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The disclosure consists in the foregoing and also envisages constructions of which the following gives examples only.

BRIEF DESCRIPTION OF THE FIGURES

Preferred embodiments of the disclosure will be described by way of example only and with reference to the following drawings.

FIG. 6*a* shows the conduit in a first or open configuration, and FIG. 6*b* shows the conduit in a second or closed configuration.

FIG. 9A is a perspective view, FIG. 9B is an exploded perspective view, FIG. 9C is a top (plan) view, FIG. 9D is a front view, FIG. 9E is a side view, FIGS. 9F to 9H are 'transparent top, front and side views respectively.

FIG. 10A is a perspective view, FIG. 10B is an exploded perspective view, FIG. 10C is a top (plan) view, FIG. 10D is a side view on a connector of the cannula.

FIG. 11A shows the connector parts separated, FIG. 11B shows the connector parts connected together, FIG. 11C shows the parts rotated relative to one another to disengage, and FIG. 11D is a cross section on line I-I in FIG. 11C.

FIG. 16A is a perspective view, FIG. 16B is a front view, FIG. 16C is an exploded view, FIG. 16D is a perspective view showing a compliant cannula body rotated relative to a relatively rigid cannula member, and FIG. 16E is a cross section on line I-I in FIG. 16B.

FIG. 18A is a front perspective view, FIG. 18B is a rear perspective view, FIG. 18C is a cross sectional view showing an actuating lever in an open position to allow a flow of gases to flow from nasal prongs of the cannula, and FIG. 18D is a cross sectional view showing an actuating lever in a closed position to block a flow of gases flowing from nasal prongs of the cannula.

DETAILED DESCRIPTION

Figure 1:
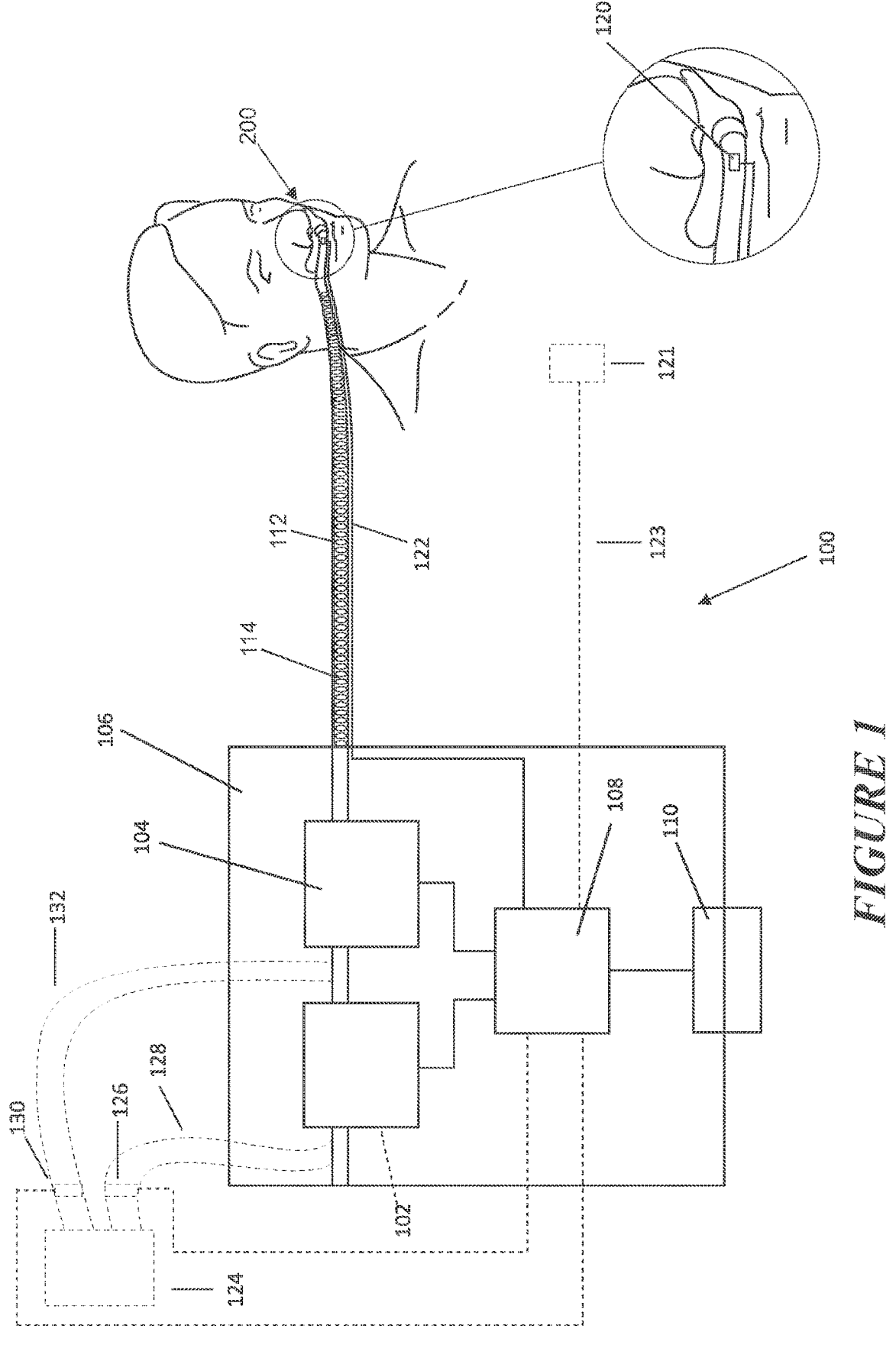
FIG. 1 shows a respiratory therapy system.

Various embodiments are described with reference to the Figures. Throughout the Figures and specification, the same reference numerals may be used to designate the same or similar components, and redundant descriptions thereof may be omitted.

FIG. 1 shows a respiratory therapy system 100. The respiratory therapy system 100 comprises a flow generator 102. The flow generator 102 is configured to generate gas flows that are passed through the respiratory therapy system 100. The flow generator 102 passes the air to a humidifier 104. The humidifier 104 is configured to heat and humidify gas flows generated by the flow generator 102. In some configurations, the flow generator 102 comprises a blower adapted to receive gases from the environment outside of the respiratory therapy system 100 and propel them through the respiratory therapy system 100. In some configurations, the flow generator 102 may comprise some other gas generation means. For example, in some configurations, the flow generator 102 may comprise a source available from a hospital gas outlet (e.g. oxygen or air), or one or more containers of compressed air and/or another gas and one or more valve arrangements adapted to control the rate at which gases leave the one or more containers. As another example, in some configurations, the flow generator 102 may comprise an oxygen concentrator. In some configurations, the flow generator 102 may be adapted to deliver a high flow therapy.

According to various configurations and embodiments described herein, a flowrate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100

L/min, about 70 to 80 L/min). Flowrates above about 15 L/min in some embodiments may be used in such configurations or embodiments, in particular but not limited to flowrates of about 60-70 L/min. 'High flow' or 'high flow therapy' may refer to the delivery of gases to a patient at a flow rate of between about 5 or 10 L/min and about 100 L/min, or between about 15 L/min and about 95 L/min, or between about 20 L/min and about 90 L/min, or between about 25 L/min and about 85 L/min, or between about 30 L/min and about 80 L/min, or between about 35 L/min and about 75 L/min, or between about 40 L/min and about 70 L/min, or between about 45 L/min and about 65 L/min, or between about 50 L/min and about 60 L/min.

Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's normal peak inspiratory demand, to increase oxygenation of the patient and/or reduce the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising rebreathing of carbon dioxide, nitrogen, etc.

As relatively high gas delivery flow rates may be used with the embodiments or configurations described herein, the gases being supplied or delivered to the user or patient may be delivered to different parts of the user's or a patient's airway.

Such relatively high flow rates of gases may assist in providing the supplied gases into a user's airway, or to different parts of a user's airway, for example such flow rates may allow for a delivery of such gases to the upper or lower airway regions. Upper airway region typically includes the nasal cavity, pharynx and larynx, while the lower airway region typically includes the trachea, primary bronchi and lungs.

Figure 5:
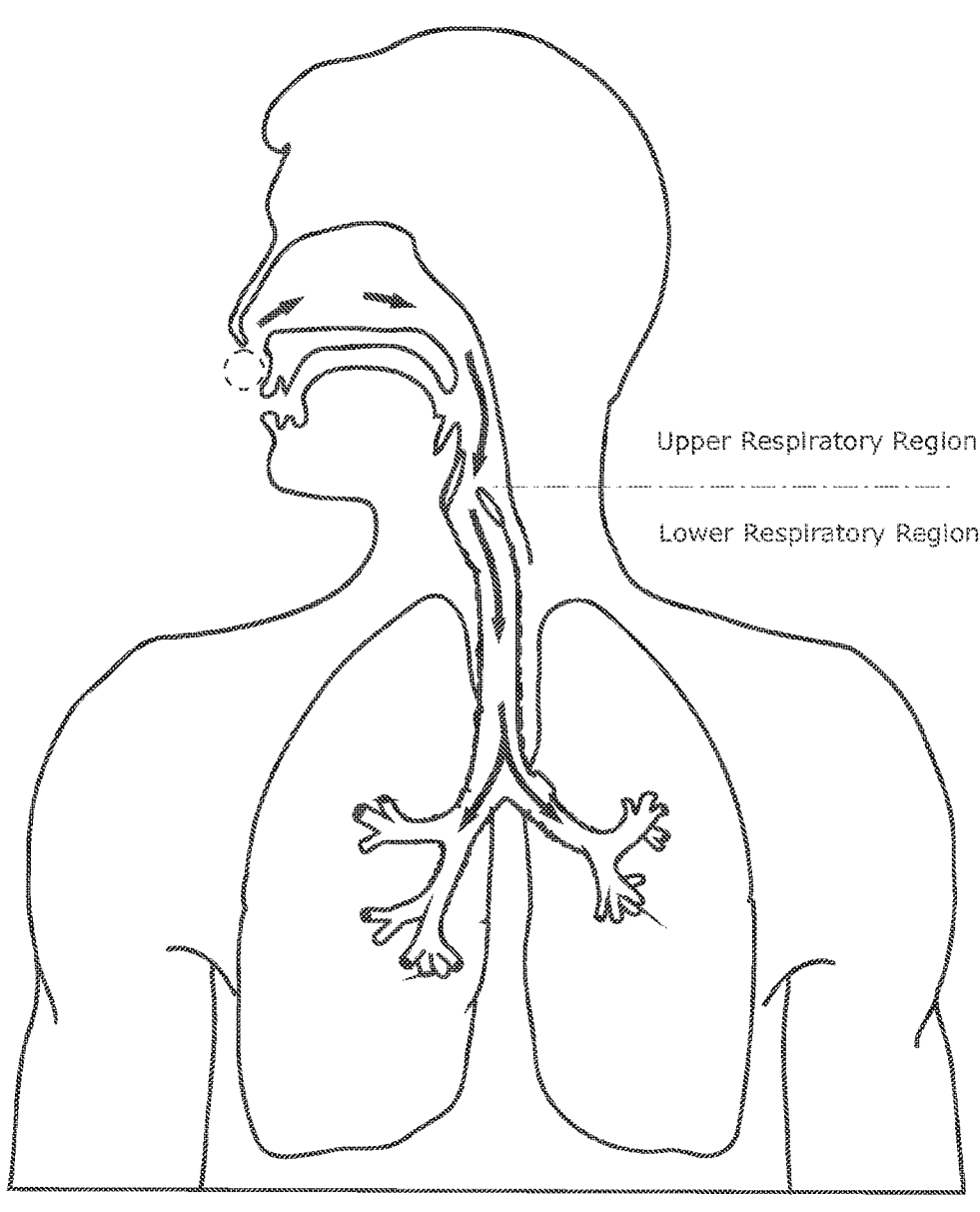
FIG. 5 shows a typical airway of a patient.

FIG. 5 shows a typical airway of a person, and includes arrows to indicate how a relatively high flow rate of gases supplied to a user may be utilised to effectively push or drive the supplied gases further or deeper into a user's airway than when the person is under normal or typical self-driven respiratory conditions, or when a patient has a diminished respiratory drive.

The respiratory therapy system 100 comprises a housing 106 that at least partially houses both the flow generator 102 and the humidifier 104 (e.g. the respiratory therapy system 100 may comprise an integrated flow generator/humidifier apparatus). In other configurations the flow generator 102 and humidifier 104 may have separate housings. A hardware controller 108, also referred to herein as controller 108 or hardware 108, is shown to be in electronic communication with the flow generator 102 and the humidifier 104, although in some configurations the hardware controller 108 might only communicate with the flow generator 102 or the humidifier 104. The hardware controller 108 may comprise a microcontroller or some other architecture configured to direct the operation of controllable components of the respiratory therapy system 100, including but not limited to the flow generator 102 and/or the humidifier 104. An input/ output module 110 is shown to be in electronic communication with the controller 108. The input/output module 110 may be configured to allow a user to interface with the controller 108 to facilitate the control of controllable components of the respiratory therapy system 100, including but not limited to the flow generator 102 and/or the humidifier 104, and/or view data regarding the operation of the respiratory therapy system 100 and/or its components. The input/output module 110 might comprise, for example, one or more buttons, knobs, dials, switches, levers, touch screens, speakers, displays and/or other input or output peripherals that a user might use to view data and/or input commands to control components of the respiratory therapy system 100.

As further shown in FIG. 1, a supplementary gas source 124 may be used to add one or more supplementary gases to the gases flowing through the respiratory therapy system 100. The one or more supplementary gases join the gas flow generated by the flow generator 102. The supplementary gas source 124 may be configured to deliver one or more supplementary gases including but not limited to air, oxygen ($O_2$), carbon dioxide ($CO_2$), nitrogen ($N_2$), nitrous oxide (NO), and/or heliox (a mixture of helium and oxygen). The supplementary gas source 124 may deliver the one or more supplementary gases via a first supplementary gas conduit 128 to a location upstream of the flow generator 102, and/or may deliver the one or more supplementary gases via a second supplementary gas conduit 132 to a location downstream of the flow generator 102 and/or upstream of the humidifier 104. One or more supplementary flow valves 126, 130 may be used to control the rates at which the one or more supplementary gases can flow from the supplementary gas source 124 and through the first and/or second supplementary gas conduits 128, 132. One or more of the supplementary flow valves 126, 130 may be in electronic communication with the controller 108, which may in turn control the operation and/or state of the one or more of the supplementary flow valves 126, 130. In other configurations, the supplementary gas source 124 may be configured to add one or more supplementary gases downstream of the humidifier 104.

Figure 19:
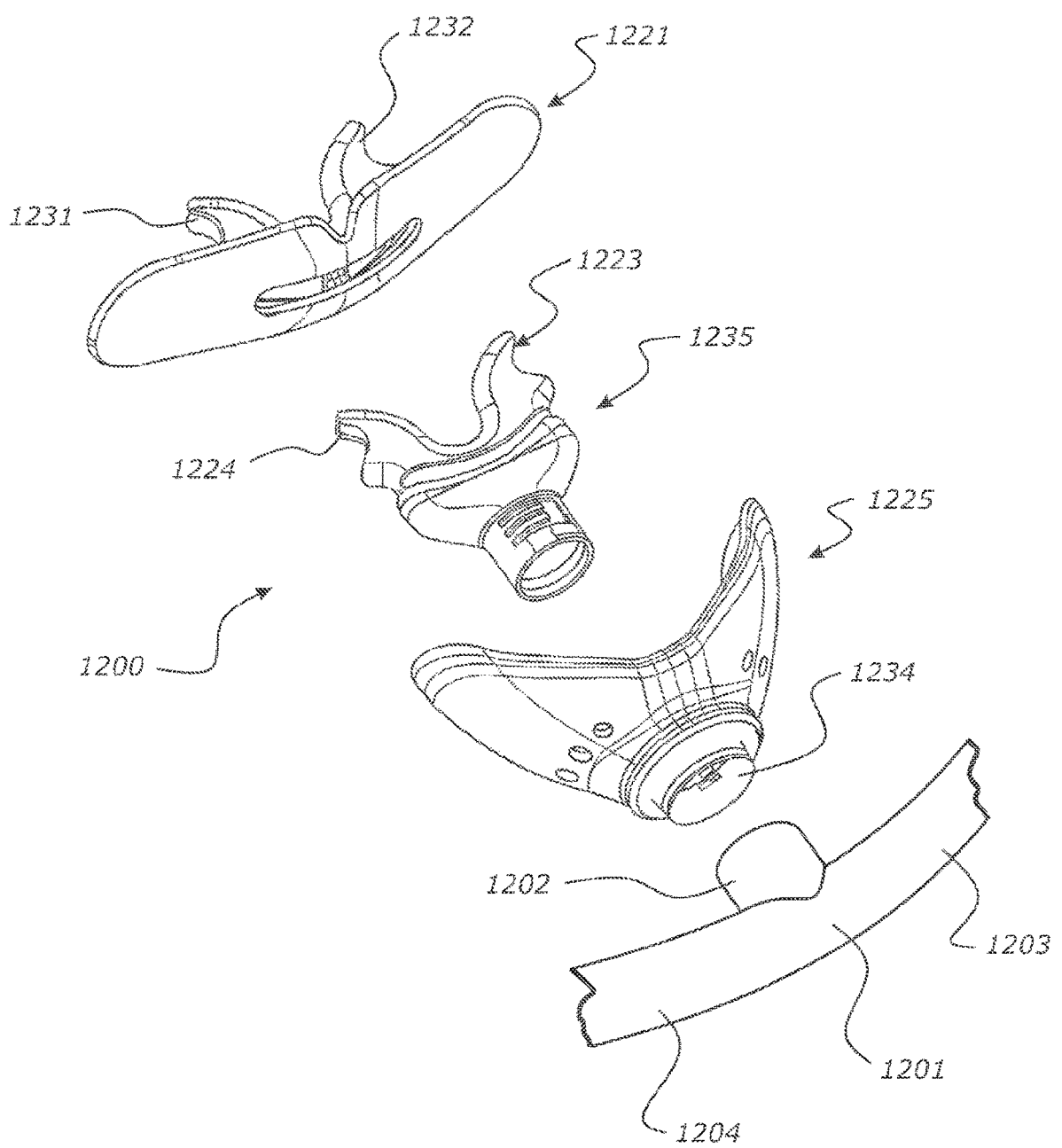
FIG. 19 is an exploded view of an oral interface.

As shown in FIG. 1, a conduit 112, also referred to herein as inspiration conduit 112, inspiratory conduit 112, inspiratory tube patient conduit 112, single patient conduit 112, or two patients conduits 112, extending from the humidifier 104 links the humidifier 104 to a patient interface 200, also referred to herein as cannula 200, first interface 200, first patient interface 200, nasal cannula 200, or nasal interface 200. The conduit 112 may comprise a conduit heater 114 adapted to heat gases passing through the conduit 112. In other configurations the conduit heater 114 may not be present. The patient interface 200 is shown to be a nasal cannula, although it should be understood that in some configurations, other patient interfaces may be suitable. For example, in some configurations, the patient interface 200 may comprise a sealing or non-sealing interface, and may comprise a nasal mask, an oral mask, an oro-nasal mask, a full face mask, a nasal pillows mask, a nasal cannula, an endotracheal tube, tracheostomy tube, a combination of the above or some other gas conveying system. In a preferred embodiment, the patient interface 200 is a non-sealing interface such as a nasal cannula, which allows gases to be exchanged with the environment. For example, the non-sealing cannula allows carbon dioxide to be removed and/or cleared from the patient's airways while the patient receives flow therapy from the system 100. Further, in some preferred embodiments, the patient interface 200 is in the form of a nasal interface, such that the system does not interfere with other oral airway equipment and/or devices, for example, a tracheal tube in an intubation procedure. Accordingly, the patient may continue to receive flow therapy throughout the intubation procedure. In other embodiments, the patient interface 200 is an oral interface, for example an oral interface that is received in a user's mouth. An oral interface may be preferred in situations involving medical procedures via the nose, such that the interface does not interfere with nasal airway equipment and/or devices, for example a tracheal tube used in a nasal intubation procedure. In other embodiments the interface may be suitable for both nasal and oral placement or may be adapted between a nasal and an oral configuration. An example oral interface is illustrated in FIG. 19.

As shown, in some configurations the patient interface 200 may also comprise a gas sensing module 120 adapted to measure a characteristic of gases passing through the patient interface 200. In other configurations the gas sensing module 120 could be positioned and adapted to measure the characteristics of gases at or near other parts of the respiratory therapy system 100. The gas sensing module 120 may comprise one or more sensors adapted to measure various characteristics of gases, including but not limited to pressure, flow rate, temperature, absolute humidity, relative humidity, enthalpy, gas composition, oxygen concentration, carbon dioxide concentration, and/or nitrogen concentration. Gas properties determined by the gas sensing module 120 may be utilized in a number of ways, including but not limited to closed loop control of parameters of the gases. For example, in some configurations flow rate data taken by a gas sensing module 120 may be used to determine the instantaneous flow, which in turn may be used to determine the respiratory cycle of the patient to facilitate the delivery of flow in synchronicity with portions of the respiratory cycle. The gas sensing module 120 may communicate with the controller 108 over a first transmission line 122. In some configurations, the first transmission line 122 may comprise a data communication connection adapted to transmit a data signal. The data communication connection could comprise a wired data communication connection such as but not limited to a data cable, or a wireless data communication connection such as but not limited to Wi-Fi or Bluetooth. In some configurations, both power and data may be communicated over the same first transmission line 122. For example, the gas sensing module 120 may comprise a modulator that may allow a data signal to be 'overlaid' on top of a power signal. The data signal may be superimposed over the power signal and the combined signal may be demodulated before use by the controller 108. In other configurations the first transmission line 122 may comprise a pneumatic communication connection adapted to transmit a gas flow for analysis at a portion of the respiratory therapy system 100.

Additionally as shown a physiological sensor module 121 may be present. The physiological sensor module 121 may be configured to detect various characteristics of the patient or of the health of the patient, including but not limited to heart rate, EEG signal, EKG/ECG signal, inertial sensors attached to the patient (e.g.: chest) to detect movement, blood oxygen concentration (via, for example, a pulse oximeter), blood $CO_2$ concentration, transcutaneous $CO_2$ (TcCO2) and/or blood glucose. Similarly, the physiological sensor module 121 may communicate with the controller 108 over a second transmission line 123. The second transmission line 123 may comprise wired or wireless data communication connections similarly to the first transmission line 122, and power and data may be communicated similarly. The physiological sensor module 121 may be used, for example, to determine the blood oxygen saturation of the patient.

Figure 2:
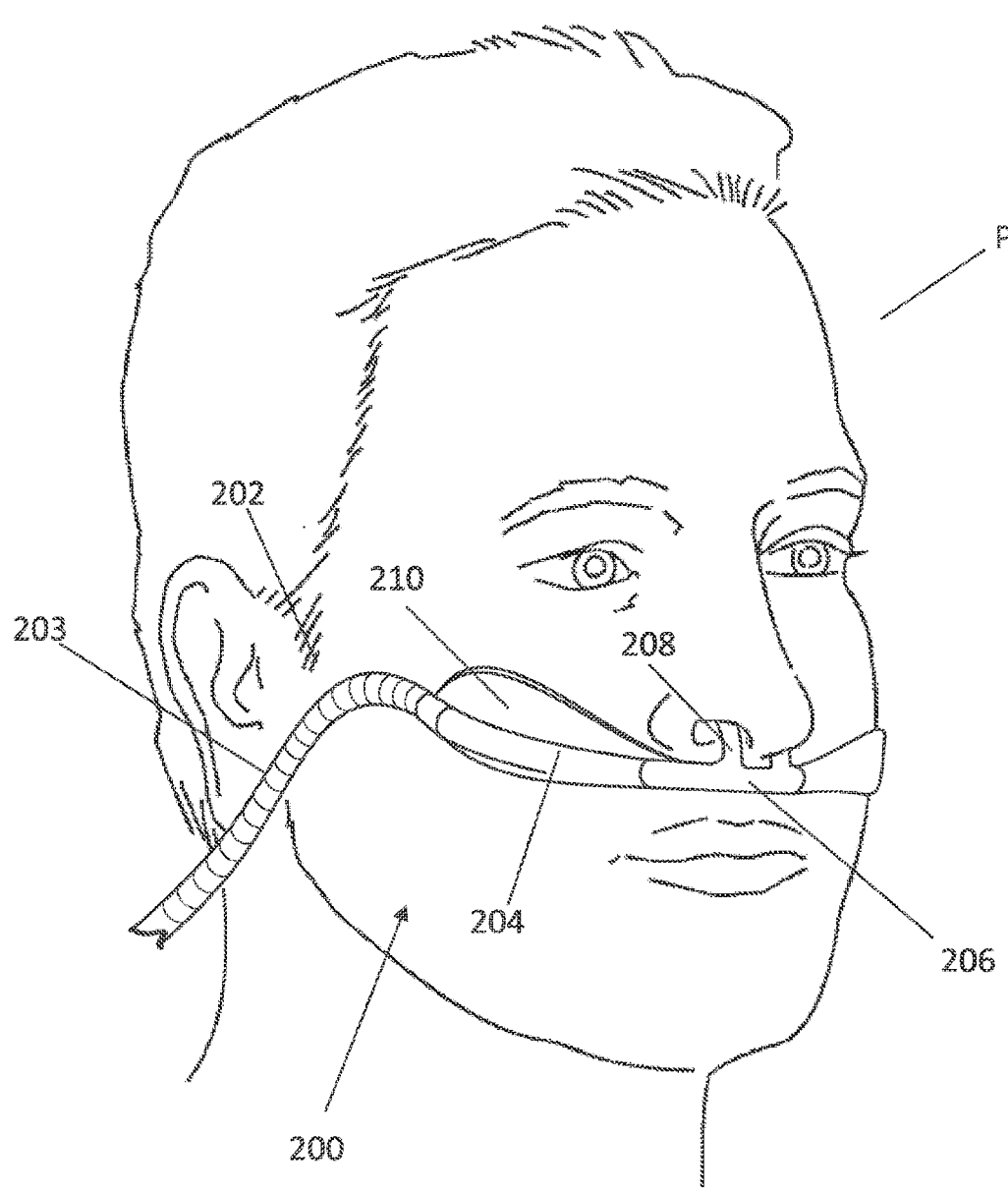
FIG. 2 shows a patient wearing a patient interface.

FIG. 2 shows a user or patient P wearing a patient interface 200, for example the patient interface 200 of the respiratory system of FIG. 1. The patient depicted is an adult, however, the patient may be an infant or juvenile. In the illustrated non-limiting configuration, the patient interface 200 is a nasal cannula. The patient interface 200 comprises a first gas conduit 202, also referred to herein as conduit 202, first conduit lumen 202, or gas conduit 202. The first gas conduit 202 is adapted to receive gases from the respiratory therapy system 100 (for example, via the conduit 112 shown in FIG. 1) and channel the gases to the patient P. The first gas conduit 202 may comprise a reinforcement element 203 adapted to strengthen and/or add rigidity to the first gas conduit to prevent deformation or collapse of the first gas conduit 202 arising due to the application of forces against the first gas conduit 202. The reinforcement element 203 may include a number of structures, including but not limited to plastic or metallic reinforcing beads that lie in or on the wall of the first conduit lumen 202.

The first gas conduit 202 is in pneumatic communication with a flow manifold 206. The flow manifold 206 receives gases from the first gas conduit 202 and passes them to one or more nasal delivery elements 208, also referred to herein as nasal prongs 208. The one or more nasal delivery elements 208 extend outwardly from the flow manifold 206. The one or more nasal delivery elements 208 are adapted to be non-sealingly positioned in one or more nares of the patient P. As shown, the patient interface 200 comprises two nasal prongs 208 adapted to be positioned one in each of the patient's nares. Each nasal prong 208 may be shaped or angled such that it extends inwardly towards a septum of the patient's nose. Alternatively the first patient interface 200 may be a sealing nasal interface.

In the embodiment shown in FIG. 2, the flow manifold 206 receives flow from one lateral side of the flow manifold 206 (e.g. with respect to an imaginary vertical plane bisecting the face of the patient P) and channels flow to the manifold and each of the nasal prongs 208. In some embodiments a conduit may extend from the left hand side or from the right hand side of the manifold. In some situations providing the conduit on the left hand side of the patient interface may be preferred for access for a clinician, for example for intubation. Alternatively, a conduit extending from the right hand side may be preferred, for example in procedures such as endoscopies where the patient is typically lying on his or her left hand side. In other configurations, the patient interface 200 may comprise greater (for example, three or four) or fewer (for example, one) nasal delivery element 208. In other configurations, each nasal delivery elements 208 can have different properties. For example, one of a pair of nasal delivery elements 208 can be relatively long and the other nasal delivery element 208 can be relatively short.

In some configurations, the flow manifold 206 may be configured to receive flow from two lateral sides of the flow manifold 206 (e.g. from a 'left' and 'right' of the flow manifold 206 instead of just the patient's right hand side of the flow manifold 206 as seen in FIG. 2). In some such configurations, multiple gas conduits may be used to provide for pneumatic communication between the flow manifold 206 and the respiratory therapy system 100. For example, the patient interface may comprise dual conduits, the first gas conduit 202 extending from a first side of the interface (in the illustrated example the right hand side of the patient)

and a second gas conduit extending from a second opposite side of the interface. In some configurations, the flow manifold 206 may be configured to receive flow from a non-lateral side of the flow manifold 206 (e.g. from a 'bottom' or 'top' of the flow manifold 206).

The patient interface may further comprise mounts and/or supports, e.g., cheek supports 210, for attaching and/or supporting the gas conduit 202 or conduits on the patient's face. Alternatively or additionally, the patient interface may be held in place via one or more headstraps or headgear.

The first gas conduit 202 of the patient interface 200 comprises a first portion 204 configured to transition from a first configuration in which a first level of gases is able to pass through the first portion 204 to a second configuration in which a second level of gases is able to pass through the first portion 204.

Figure 3:
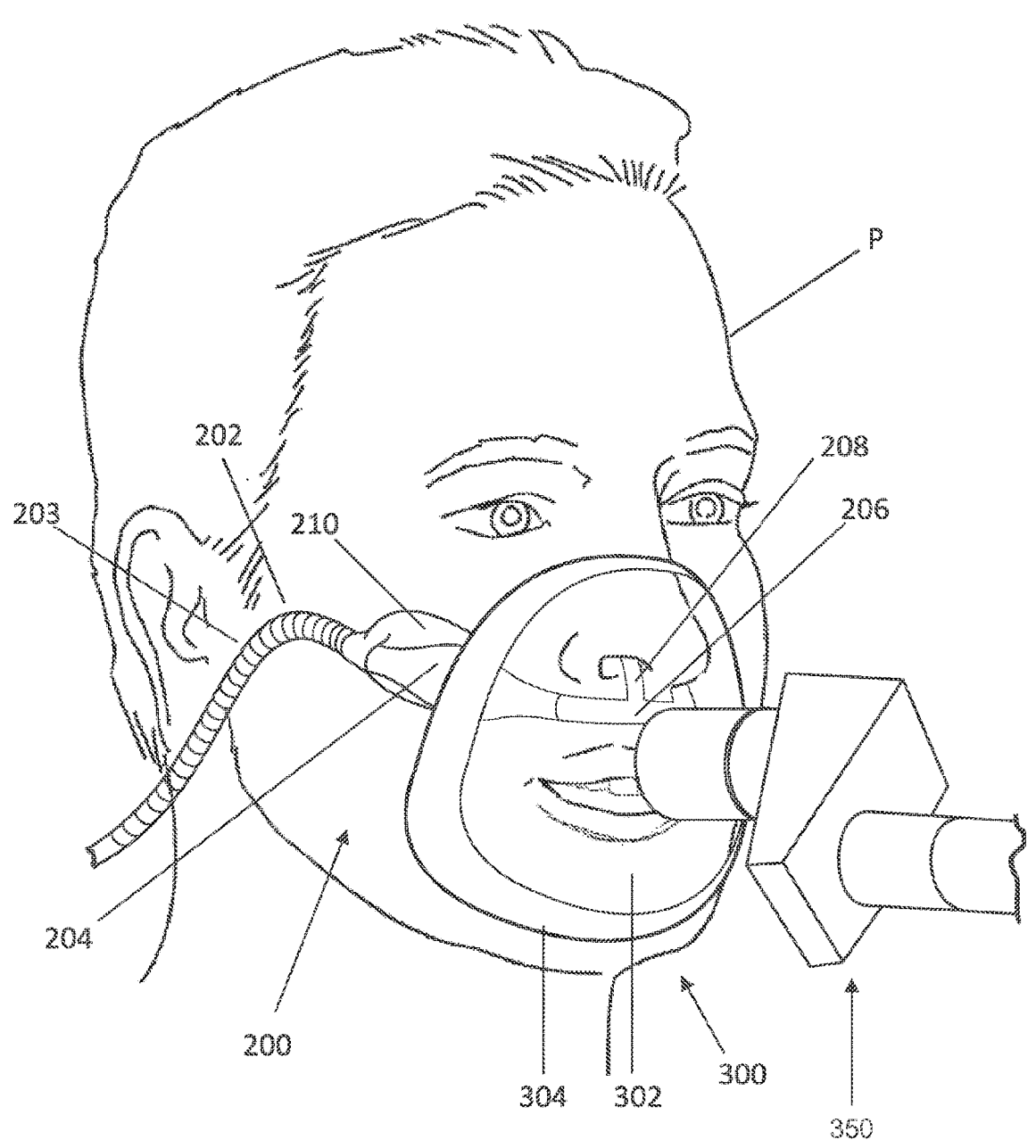
FIG. 3 shows a patient wearing a patient interface (a first patient interface) and a face mask (a second patient interface).

FIG. 3 shows a non-limiting exemplary embodiment of a patient P wearing the patient interface 200 as shown in FIG. 2 (a first patient interface) underneath a face mask 300, also referred to herein as face mask assembly 300, mask 300, mask assembly 300, or second patient interface 300. FIG. 3 schematically shows the face mask as a transparent structure in order to illustrate the patient interface 200 under it. The first patient interface 200 may be used with a first respiratory support subsystem and the second patient interface 300 may be used together with a second respiratory support subsystem.

A system may find benefit in the selective delivery of separate therapies to a patient using different patient interfaces, and/or in stopping or ceasing the delivery of a therapy from an interface and/or allowing gases provided by an interface to be sampled. The system and devices as described find particular application in emergency resuscitation, around intubation of a patient receiving high flow therapy, ear, nose, and throat (ENT) surgery, in assisting with conditioning of a patient in a pre-operative state prior to administration of anaesthetics, and during post-extubation and recovery.

Face mask assembly 300 may be used as or with a second respiratory support subsystem and/or to deliver one or more substances other than a substance delivered by the cannula 200, for example anesthetic agents or oxygen, to the patient, or the same substance but at different flow and/or pressure levels. Alternatively, the face mask assembly 300 may be used to stop the delivery of therapy from a first respiratory support subsystem. The face mask assembly 300 may also be adapted to measure respiratory gases, for example exhaled carbon dioxide from the patient, the measurements of which may otherwise be affected by flow from the patient interface 200 of the first respiratory support subsystem.

Accordingly, the embodiment shown in FIG. 3 allows for the alternation between the two different respiratory support subsystems. Additionally, this configuration may allow the patient interface 200 to be left on the patient throughout the surgical procedure and/or into recovery (whether or not the patient continues to receive flow therapy through the patient interface 200 throughout the procedure) without interfering with other clinical practices.

In the embodiment shown, face mask assembly 300 comprises a full face mask 302, also referred to herein as face mask 302 or mask 302, configured to cover both the patient's nose and mouth. In other configurations, the face mask 300 may be a nasal mask which is placed over the patient interface 200 to cover only the patient's nasal region.

As shown, the face mask 302 comprises a seal region 304 adapted to seal against the patient's face. The face mask assembly 300 is connected to a second gas source, for example via a filter element 350, which supplies the one or more other gases to the patient via the face mask. That is, the second gas source is preferably different from the source supplying gas (for example, supplementary gas source 124/ flow generator 102) to the patient interface 200.

In a preferred embodiment, the face mask assembly 300 is connected to a separate gas source or a separate respiratory support device. For example, the respiratory support can be a ventilator or a CPAP or a high flow therapy device or a manual resuscitator (for example a hand held face mask with bag). Alternatively or additionally the face mask assembly 300 may be connected to a device for measuring a characteristic of respiratory gases.

Alternatively the mask assembly 300 could be connected to an anesthetic device and anesthetic gas, or air, or oxygen, or a combination of gases, can be delivered via the mask 302.

The embodiment shown in FIG. 3 allows for the delivery of gas from multiple sources via at least two different respiratory support modes, and further allows a doctor, clinician or medical professional to quickly and easily change the type of respiratory support mode.

In one particular application, a patient preparing for anaesthesia can be pre-oxygenated by delivering a high flow of oxygen or humidified gases or mixture of both via a nasal cannula. In some circumstances, anesthesiologists managing the sedation of a patient may want to switch between delivery of gas flow from one patient interface (for example a nasal cannula 200) and delivery of gas flow from another patient interface, such as via a face mask 300.

Anaesthesiologists also use a mask with a bag to oxygenate a patient, and in some instances find it more beneficial to use a bag mask if a patient's vital signs begin to drop for example to deliver more pressure or have greater control over the variation in delivered pressure. In some situations a medical professional may wish to switch between different respiratory systems or support modes. In first mode respiratory support may be provided by first respiratory support system (for example via the patient interface 200) and in a second mode respiratory support may be provided by a second respiratory support system (for example via the patient interface 300), with the support from the first system switched off. For example, the additional flow from a high flow provided by nasal interface 200 may also modify the expected behaviour of the anaesthetic circuit provided by the face mask 300, and therefore it may be advantageous to be able to turn the additional flow from the first respiratory system off.

In some configurations, the switching between two respiratory support modes or subsystems may be facilitated by a structure of the first gas conduit 202, which has first portion 204 configured to transition from a first configuration in which a first level of gases is able to pass through the first portion 204 to a second configuration in which a second level of gases is able to pass through the first portion 204.

In some configurations, the first portion 204 is configured to be more collapsible or otherwise better adapted at changing the flow of gas through the first portion 204 (therefore reducing the flow of gas through the conduit and to the patient) than other portions of the conduit 202, and/or allowing a seal of a mask to seal over the top of the conduit. In other configurations the entire conduit may be configured to be collapsible. In some configurations a vent arrangement may be provided upstream of a collapsible portion, to vent gases from the conduit upstream of the collapsible portion to atmosphere.

In some embodiments, the first configuration or first condition is a substantially open configuration and the second configuration or second condition is a substantially closed configuration. That is, the conduit 202 is configured to be more collapsible, deformable or otherwise adapted to fully close off the flow at the first portion 204 than at other portions of the conduit 202.

Figure 4:
FIG. 4 shows a cross-section of a portion of a patient interface or conduit.
Figure 4:
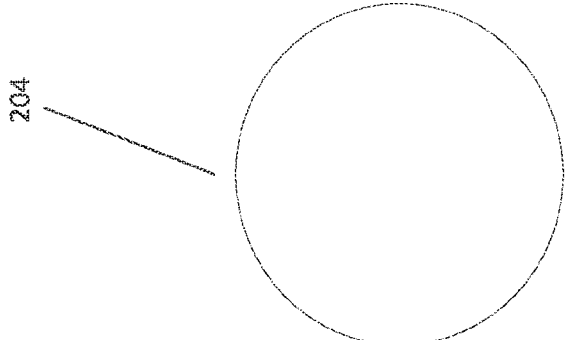

FIG. 4 shows one example of this configuration, in which the conduit (for example the conduit 202 of the nasal cannula 200 of FIG. 3) at a first portion 204 is substantially closed by the seal 304 of face mask 302. In such an embodiment, the first portion (i.e. the more collapsible or deformable section) of the first gas conduit should be of a length that is greater than a width of a section of a seal of the face mask that bears over the first portion of the first gas conduit. This ensures the seal of the face mask does not bear over a non-collapsible section of the first gas conduit. For example, the first portion may extend from a distance of 35 mm or less from the centre of a user's nose to at least 50 mm from the centre of a user's nose, the first portion having a length of at least 15 mm. In some embodiments the length of the first portion may be at least 15 mm, 20 mm, 25 mm, 30 mm, 35 mm, 40 mm, 45 mm, 50 mm or greater.

The first portion 204 may progress between the first and second configurations based on a relative level of force applied to the wall of the first portion 204. For example, as shown in FIG. 3, the force may be applied by the seal 304 of face mask 302. In this example, first portion 204 is configured to be positioned under the seal 304 of the face mask 302.

Alternatively, the force may be applied to first portion 204 by other means, e.g., clamps (not shown), or alternatively a medical practitioner may compress the conduit by pressing on the conduit wall with a finger or thumb.

In some embodiments, the seal of the face mask acting on the first portion of the gas conduit causes the first portion to form a seal or at least a partial seal between the nasal outlets of the first patient interface 200 and the flow generator 102. Additionally, the seal of the face mask forms a seal or at least a partial seal over the first portion of the gas conduit.

Switching between respiratory support therapies is therefore achieved simply by applying a mask to the patient's face so that the seal of the mask collapses (partially or completely) the first portion of the gas conduit of the first interface 200 to 'turn off' or reduce the therapy supplied by the first interface 200 and also provides a seal between the face mask 300 and the external surface of the first portion 204 of the conduit 202 such that therapy can be provided by the mask 300 with the therapy provided by the first interface shut off. The cannula with a collapsible conduit portion allows a user, e.g. an anesthetist or a nurse or a clinician to use a mask and prevent delivery of gases from multiple sources (e.g. the mask and cannula). The first interface 200 is structured and functions in a manner to prevent the delivery of high flow and other respiratory therapy or anesthesia gases through a mask. In some embodiments the removal of the mask from the patient's face allows the therapy supplied by the first interface to recommence, as the conduit returns from the collapsed configuration to the open configuration.

Figure 6A:
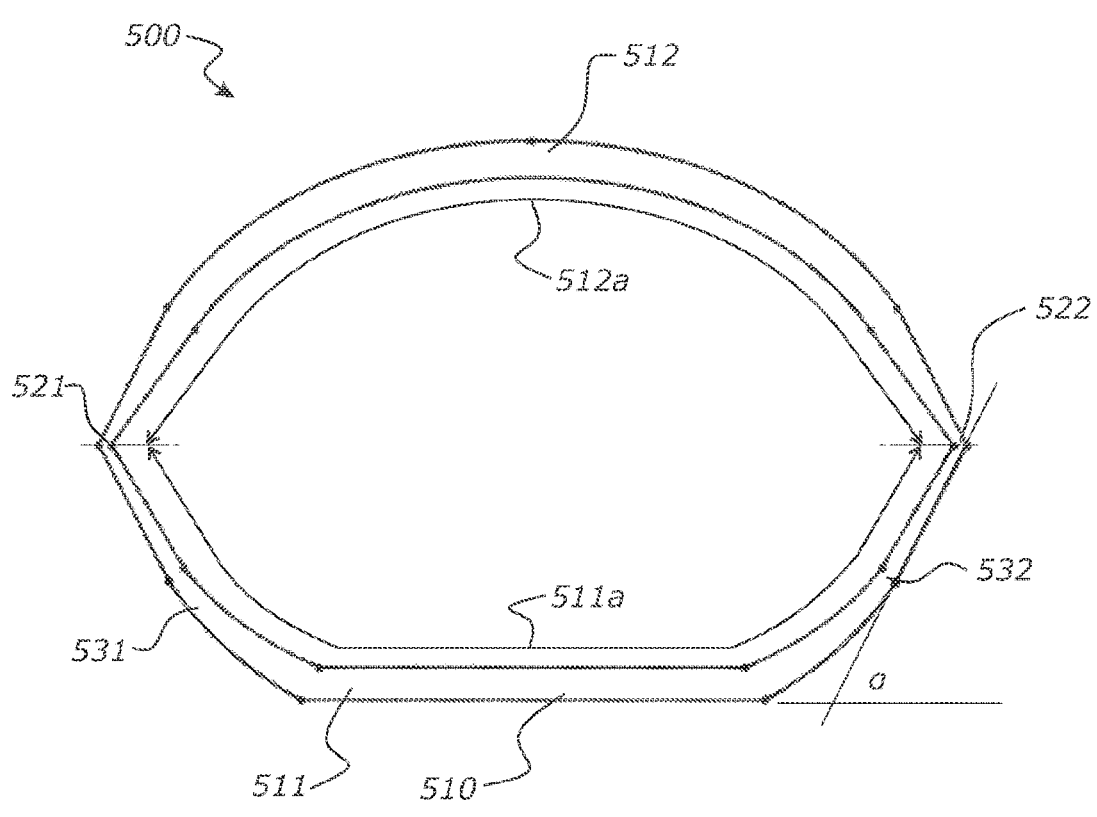
FIGS. 6A and 6B show a lateral (across the flow path of the conduit) cross section of a collapsible portion of a conduit.
Figure 6B:
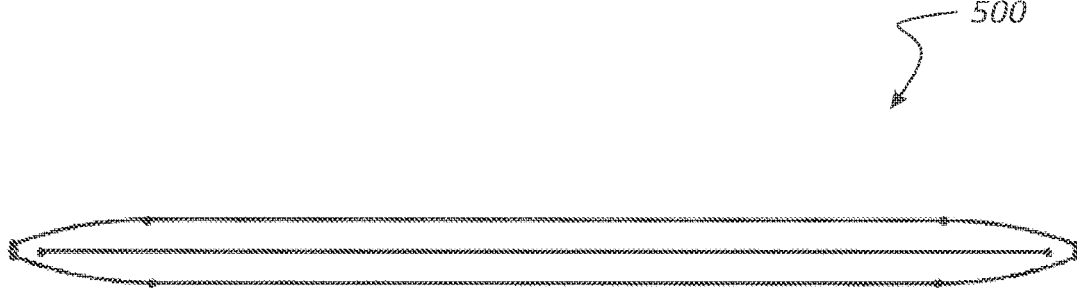

FIGS. 6a and 6b illustrate a lateral cross section of a collapsible portion of a conduit 500, which may be integrally formed with and as part of a patient interface, for example a high flow cannula. FIG. 6a shows the conduit 500 in a first or open configuration, and FIG. 6b shows the same conduit 500 cross section in a second or collapsed/closed configuration. In the open configuration gases may flow along the conduit and in the closed configuration the collapsible portion is substantially sealed/occluded so that gases flow along the conduit substantially ceases.

In the embodiment of FIG. 6a, the lateral cross section of the collapsible portion of the conduit 500 comprises a first side 511 with a flat portion 510 for positioning against a user's face. The flat portion is thought to assist with positioning the conduit on a user's face, for example assisting with holding the tube in a correct orientation on the user's face for when a mask is applied over the tube, and/or assist with the conduit moving from the open to the closed configuration. The flat portion may help the conduit to rest on the user's face and provide a stable mounting surface. A second side 512 of the conduit is opposite to the first side and faces away from the user's face. The first and second sides are joined by first and second fold points 521 and 522. In the open configuration the fold points are spaced away from the flat portion of the first side and therefore away from the user's face. In an alternative embodiment (not illustrated) the fold points may be coplanar with the flat section. The collapsible cross section may be such that the fold points are adjacent or rest on the face. In the configuration shown in FIG. 6A the internal length of the first side and the second side being equal allows for flat folding of the collapsible portion.

In a partially closed or closed configuration the second side is moved towards or against the first side with the collapsible portion folding at the first and second fold points. In the closed configuration the fold points 521, 522 may be moved to be against or adjacent the face of a user. In order to assist with the conduit sealing closed in the closed configuration to substantially prevent a flow of gases along the conduit and/or to assist with providing a substantially flat conduit over which the mask seal may seal against, an inner length of the first side between the fold points and an inner length of the second side between the fold points are substantially equal. This configuration may assist the collapsible portion to achieve a substantially flat configuration, or a configuration in which the inner surfaces of the first and second sides of the conduit come together in contact substantially fully along their lengths (e.g. without bubbles, ripples or wrinkles), when in the closed or collapsed configuration, as shown in FIG. 6b. The first and second fold points delimit or define the extent of the first and second sides. In other words, the first and second sides each extend fully between the fold points, e.g. from the first fold point to the second fold point. For example, the length of the first side 511 between the fold points 521, 522 is illustrated in FIG. 6A by double ended arrow 511a, and the length of the second side 512 between the fold points 521, 522 is illustrated in FIG. 6A by double ended arrow 512a In some embodiments, the first side may comprise an outwardly curved or arcuate portion 531, 532 between the flat portion 510 and each of the first and second fold points 521, 522 when in the open configuration. The two curved portions 531, 532 preferably have the same radius of curvature, such that the collapsible section has reflective symmetry about a centre line of the cross section. Preferably the cross section has reflective symmetry about a centreline of the cross section, the centreline extending through a centre of the first and second sides of the cross section. Having a symmetrical cross section may help to ensure that the collapsible portion collapsed to a flat shape with a minimum height profile to promote sealing of the mask seal over the collapsed conduit. In some embodiments, the outward curvature or curvature of the arcuate portions 531, 532 has a radius that is sufficiently large to prevent or reduce the occurrence of creases in the conduit or gaps between the first and second sides when in the collapsed configuration. In some embodiments the outward curvature or curvature of the arcuate portions 531, 532 may help to maintain the cross-section in the open configuration when no external force is applied. In some embodiments the outward curvature or curvature of the arcuate portions 531, 532 may help to reduce the resistance to flow of the cross-section by increasing the cross-sectional area and reducing the sharpness of internal corners.

In an alternative configuration, the curved or arcuate portions 531, 532 may be inwardly curved, or the portion of the cross section between the flat portion and between each fold point may be straight or without curvature.

In some embodiments the thickness of the curved portions 531, 532 tapers from the flat portion 510 towards the respective fold point 521, 522, from a greater thickness to a reduced thickness. The change in thickness is preferably gradual along the length of the side of the cross section to reduce or prevent the occurrence of folds or creases in the side away from the fold points 521, 522. Preferably the flat section is of a thickness that is greater than the thickness of the remainder of the first side of the cross section. The thicker flat portion provides additional structure to the conduit in an area in contact with the user's face so that the conduit does not crease or buckle or fold on the user's face which may reduce the effectiveness of the conduit sealing closed when in the closed configuration.

In some configurations, the second side 512 of the conduit is curved outwardly when in the open configuration, as shown in FIG. 6a. In some configurations the second side 512 is a continuous curved or arcuate portion, e.g. the second side is curved outwardly from the first fold point to the second fold point. In some embodiments the curvature of the second side may be about a single radius of curvature. In some configurations, the thickness of the second side 512 tapers towards each fold point 521, 522, from a greater thickness to a reduced thickness. In some embodiments, the second side is thickest at the centre or apex of the curved second side. The outward curve of the second side reduces a resistance to flow as compared to having a feature of the cross section that curves or extends inwardly towards a centre of the cross section.

Preferably the thickness of the fold points 521, 522 is less than the thickness of the remainder of the cross section of the collapsible portion. The relatively thin section of the fold points allows the section to be particularly adapted to fold or bend at the fold points to transition between the open and closed configurations. The conduit preferentially bends or folds at the fold points to move between the open and closed configurations. The thickness of the fold points relative to the thickness of other sections of the collapsible portion allows the collapsible portion to collapse flat so that preferably the collapsed portion substantially seals to substantially stop flow through the conduit, and additionally, to also facilitate the mask seal sealing over the top of the conduit and with the user's face at the edges of the collapsed portion. The thin fold points combined with the outwards curve of the second side may encourage a gradual tapering of the collapsed portion from the centre of the cross section towards the user's face in the collapsed configuration, reducing the chance of leaks between the conduit and the seal of the mask and the user's face.

In some embodiments, in the open configuration the first side adjacent each fold point is at an angle to the flat portion 510 such that an external angle (alpha) between the first side adjacent the fold point and the flat portion 510 is less than 80 degrees, or less than 75 degrees, or less than 70 degrees, or less than 65 degrees, or less than 60 degrees, or less than 55 degrees, or less than 50 degrees, or less than 45 degrees, or less than 40 degrees, or less than 35 degrees, or less than 30 degrees, or is between 50 and 70 degrees, or is between 60 and 70 degrees, or may be about 65 degrees. For example the angle is illustrated as being 62.6 degrees in FIG. 6a.

In some configurations, the first side diverges outwardly either side of the flat portion 510 towards the respective fold point 521, 522. Preferably the first side curves into (or from) the flat portion 510 so that the cross section is without a defined 'corner' at each extent of the flat portion. A sharp corner in the first side at the edge of the flat portion may cause upwards buckling on a lower surface of the cross section, creating a gap between the conduit and the face when in the collapsed configuration.

As described above, in some embodiments the flat portion may be thicker than other portions of the cross section. For example, in some embodiments, the flat portion may have a thickness of about 0.5 mm. In some embodiments, the fold points have a thickness of about 0.2 mm. In some embodiments, the flat portion may have a thickness of 0.5 mm to 1.5 mm. In some embodiments the fold point may have a thickness of 0.2 to 0.4 mm.

In some configurations, the ratio of the relative thicknesses between the (thicker) centre of the first and/or second sides of the lateral cross section and the (thinner) fold points is in the range of about 1 to 8, or about 1.5 to 3.5. In some configurations, the ratio of the relative thicknesses between the (thicker) flat portion of the first side and/or the apex of the second side of the lateral cross section and the (thinner) fold points is in the range of about 1 to 8, or about 1.5 to 3.5. In some configurations, the ratio of the thickest part of the lateral cross section to the thinnest part of the lateral cross section being the fold points is in the range of about 1 to 8, or about 1.5 to 3.5. If the ratios stated are greater than the stated range the thickest parts of the cross section may reduce the flexibility of the collapsible portion. If the ratios are less than the stated range the conduit may be too think and may collapse under its own weight and/or may result in creases, folds or wrinkles in areas outer than the fold points, which is undesirable for sealing of the conduit and also sealing with the seal of the mask over the top of the conduit. However, the walls of the collapsible section are sufficiently thin to ensure suppleness when used with the user so that the conduit is comfortable against the user's face. The above stated ratios relate to tested materials being silicone with a Shore hardness of 60 to 70A and thermoplastic polyurethane.

As an exemplary embodiment, in some configurations, the flat portion has a length of about 5 mm to 10 mm or about 7 mm, and/or a lateral width of the cross section of the collapsible portion is between 10 mm and 15 mm or about 13 mm. A distance between the fold points is greater than a width of the flat portion. In an alternative embodiment, the first side is without a flat portion 510. For example the first side may be curved between the fold points, the curvature (may include one or more radius of curvatures) extending from one fold point to the other fold point.

Figure 7A:
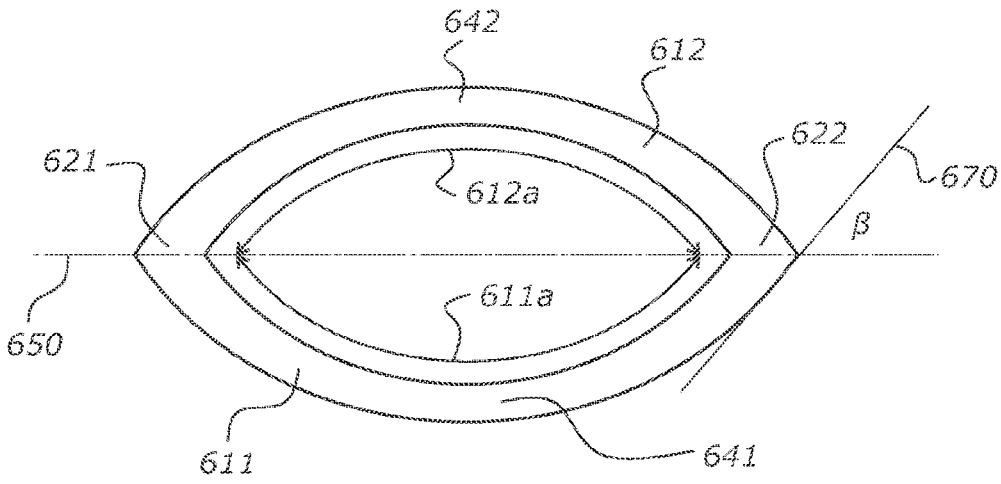
FIGS. 7A to 7C show alternative lateral cross sections for a collapsible conduit portion.
Figure 7B:
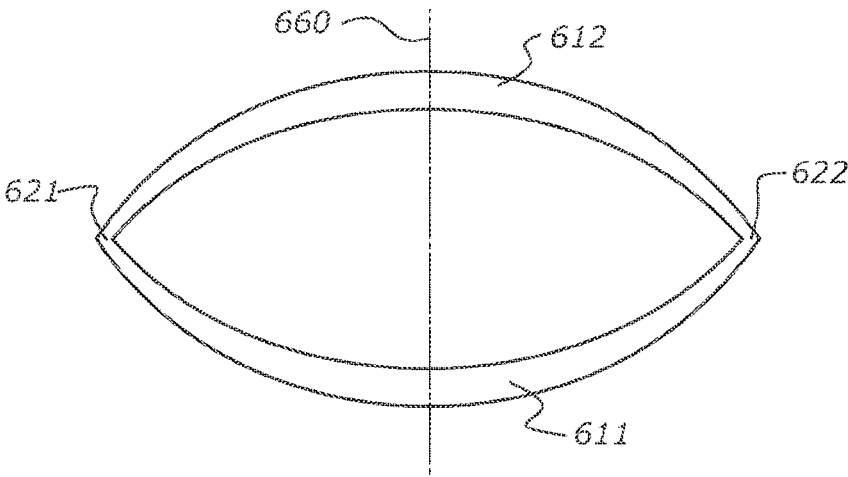
Figure 7C:
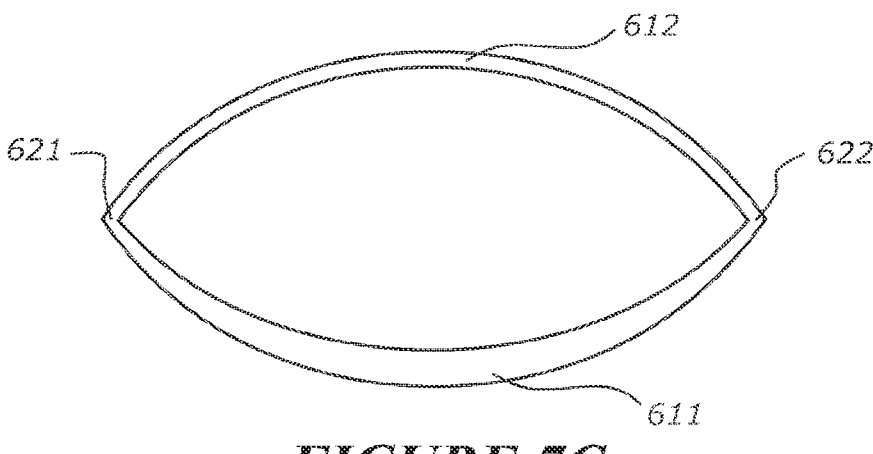

FIGS. 7a to 7c illustrate alternative cross sections for a collapsible conduit portion. With reference to FIG. 7a, the cross section has a first side 611 for positioning against a user's face, and a second side 612 opposite the first side to face away from the user's face. Unlike in the earlier described embodiment with a flat portion 510, in the embodiments of FIGS. 7a to 7c, the first side 611 is without a flat portion. The first and second sides are joined by first and second fold points 621, 622. The first and second fold points delimit or define the extent of the first and second sides, or in other words the first and second sides each extend fully between the fold points, e.g. from the first fold point to the second fold point. In the illustrated embodiments, a maximum width of the cross section is defined by a distance between the fold points.

In the illustrated embodiment the cross section is shaped so that the fold points 621, 622 are spaced away from the user's face in an open configuration. The first and second sides 611, 612 are curved outwardly when in the open configuration, so that the lateral cross section is substantially oval or elliptical; but in contrast to a true oval or elliptical shape which have rounded ends on a major axis of the oval or ellipse, in the lateral cross sections of FIGS. 7a to 7c the first and second sides converge to a point at each fold point of the cross section. When in the open configuration the fold points are spaced from the user's face and in the closed configuration the fold points are moved to be against or adjacent to the user's face.

In some embodiments, for example as shown in FIGS. 7b and 7c, the fold points are the thinnest points of the lateral cross section, such that the collapsible portion preferentially folds at the fold points when collapsing to a closed configuration. In some configurations, for example as shown in FIGS. 7b and 7c, the thickness of the first side and/or the second side tapers towards each fold point, from a greater thickness to a reduced thickness. The maximum thickness is preferably at an apex 641, 642 of each of the first side and second side respectively. In some configurations, the thickness of the fold points is less than the thickness of the remainder of the cross section of the collapsible portion. In some configurations, for example as described below in relation to the embodiment of FIG. 8b, the cross section may comprise an internal notch (780 on FIG. 8b) at the fold points so that the thickness at the fold points is reduced compare to other portions of the cross section. In some configurations, as shown in FIG. 7c, the second side may be thinner than the first side, to promote collapsing of the second side towards the first side when pressed by the seal of a mask.

In some embodiments, the ratio of the relative thicknesses between the (thicker) centre of the first and/or second sides of the lateral cross section and the (thinner) fold points is in the range of about 1 to 8, or about 1.5 to 3.5. In some configurations, the ratio of the thickest part of the lateral cross section to the thinnest part of the lateral cross section being the fold points is in the range of about 1 to 8, or about 1.5 to 3.5. As described above in relation to earlier embodiments, if the ratios stated are greater than the stated range the thickest parts of the cross section may reduce the flexibility of the collapsible portion. If the ratios are less than the stated range the conduit may be too think and may collapse under its own weight and/or may result in creases, folds or wrinkles in areas outer than the fold points, which is undesirable for sealing of the conduit and also sealing with the seal of the mask over the top of the conduit.

As described above in relation to the earlier described embodiments, it is desirable that the cross section achieves a flat shape when in the closed configuration, to substantially occlude a lumen of the conduit and present a flat shape over which a seal of a mask can rest and seal against the conduit and the user's face. To assist with achieving a flat shape when in the closed configuration the cross section may comprise a number of other features. For example, in some embodiments, the lateral cross section has reflective symmetry on a line 650 extending through the first and second fold points. In some embodiments, an inner length 611*a* of the first side between the fold points and an inner length 612*a* of the second side between the fold points are substantially equal. In some embodiments, the collapsible section has reflective symmetry about a centre line (e.g. line 660 in FIG. 7*b*) of the cross section, the centre line extending through a centre of the first and second sides of the cross section. Such features may assist with achieving a flat shape by avoiding creasing or folding other than at the fold points.

With reference to FIG. 7*a*, in some configurations, when in the open configuration a line 670 tangential to the portion of the first side adjacent to each folding point is an angle to a line 650 extending through the first and second fold points such that an angle (beta) between the line and the portion adjacent the fold point is less than 70 degrees, or less than 65 degrees, or less than 60 degrees, or less than 55 degrees, or less than 50 degrees, or less than 45 degrees, or less than 40 degrees, or less than 35 degrees, or less than 30 degrees, or is between 30 and 60 degrees, or is between 40 and 50 degrees, or may be about 45 degrees. Making this angle (beta) acute may assist in the cross section collapsing to a flat state.

Figure 8A:
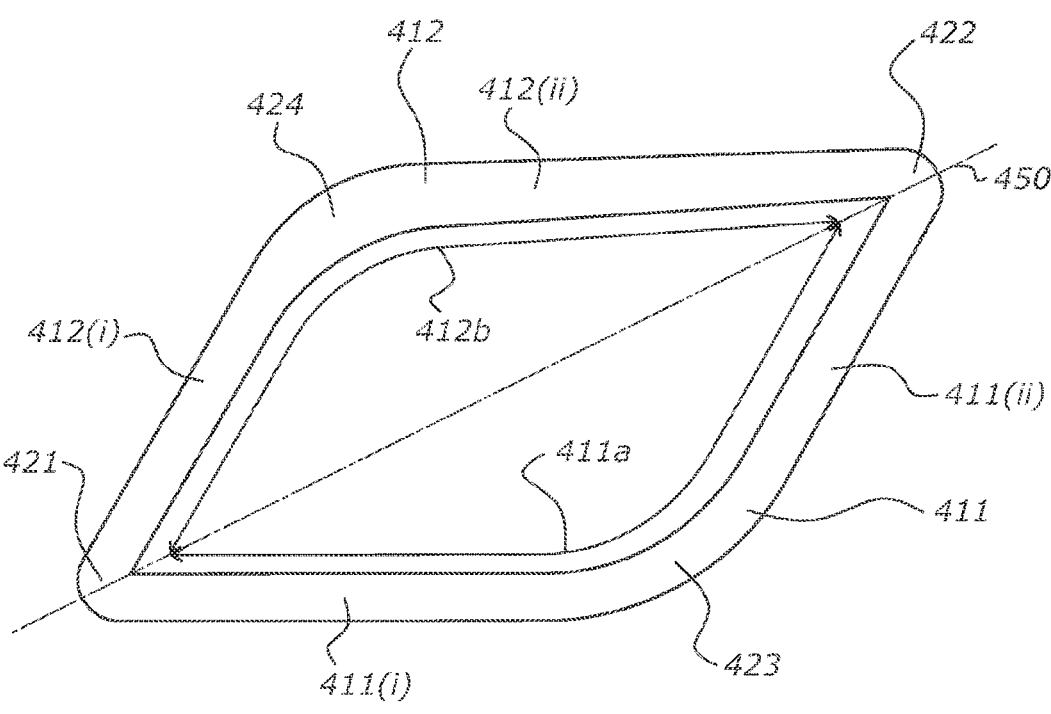
FIGS. 8A and 8B show alternative lateral cross sections for a collapsible conduit portion.
Figure 8B:
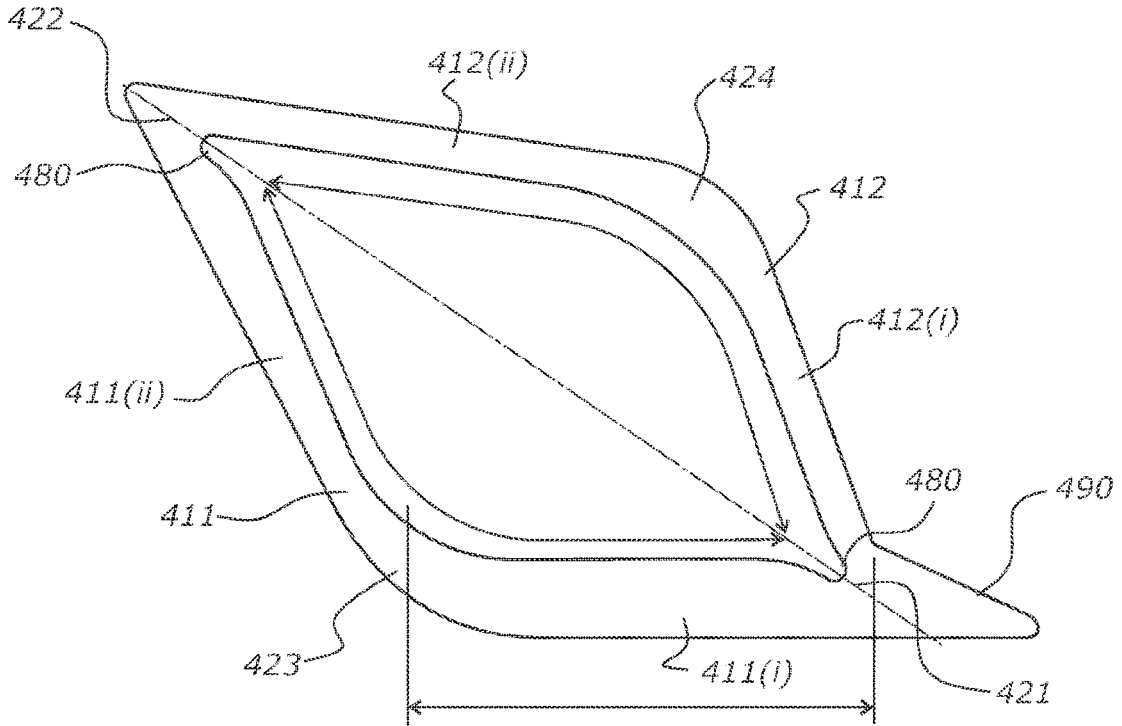

FIGS. 8*a* and 8*b* illustrate further alternative cross sections for a collapsible conduit portion. In some embodiments, the cross section may be substantially a rhombus or parallelogram shape. In FIGS. 8*a* and 8*b* the shape of the illustrated cross sections is substantially parallelogram shaped, however, one skilled in the art will understand features of the parallelogram shaped cross sections described below may be applied in a rhombus shaped cross section, unless the context suggests otherwise. The four corners of the parallelogram shaped cross section provide fold points 421 to 424, also referred to herein as corners 421, 422, 432, 424. In an open configuration the four sides of the parallelogram are spaced apart, and in a closed configuration the cross section folds at the corners 421, 422, 423, 424 so that adjacent sides of the parallelogram come together into contact. In the closed configuration the corners 421 and 422 comprising acute internal angles are located at edges of the collapsed cross section.

In some embodiments, the cross section is arranged so that a long side of the parallelogram is located against a user's face in use. Having a long side positioned against a user's face may assist to ensure the conduit is correct situated to be collapsed by the seal of a mask pressing over the conduit. Having the long side resting against face also reduces the profile of the collapsible portion of the conduit on the user's face and provides a cleaner more aesthetically pleasing, less intrusive look. In some embodiments however, the cross section may be configured such that a short side of the parallelogram rests against the user's face. This may be particularly useful for use with infants, as an infant or juvenile provides limited facial area to support the conduit.

To assist with collapsing of the conduit, preferably the acute corner angle of the parallelogram is less than 70 degrees, or less than 65 degrees, or less than 60 degrees, or less than 55 degrees, or less than 50 degrees, or less than 45 degrees, or less than 40 degrees, or less than 35 degrees, or less than 30 degrees, or is between 45 and 65 degrees, or is between 55 and 65 degrees, or may be about 60 degrees.

As described previously, preferably the fold points have a thinner cross section that other portions of the lateral cross section. In some configurations the thickness of the sides of the parallelogram (or rhombus) taper towards each corner (fold point) 421, 422 with an acute angle, from a greater thickness to a reduced thickness. In some configurations, the thickness of the acute angled corners (fold points) is less than the thickness of the remainder of the cross section of the collapsible portion. As shown in FIG. 8*b*, the cross section may comprises an internal notch 480 at the corners 421, 422 comprising an acute angle so that the thickness at the corners 421, 422 comprising an acute angle is less than the thickness of the sides 411, 412 of the cross section. The thickness of the corners 423, 424 with an obtuse angle may have a thickness similar to sides of the cross section. In some configurations, the sides of the rhombus or parallelogram have a thickness of about 0.5 mm to 1.0 mm, or about 0.7 mm, and wherein the corners comprising an acute angle have a thickness of about 0.2 mm.

In some embodiments, a first side 411 of the lateral cross section extends between the two corners 421, 422 or fold points comprising an acute angle, the first side comprising two adjacent sides 411(*i*) and 411(*ii*) and a corner 423 comprising an obtuse angle of the parallelogram. An opposite second side 412 of the lateral cross section extends between the two corners 421, 422 or fold points comprising an acute angle, the second side comprising two adjacent sides 412(*i*) and 412(*ii*) and an obtuse angled corner 424 of the parallelogram. In some embodiments, an inner length 411*a* of the first side between the fold points 421, 422 and an inner length 412*a* of the second side between the fold points 421, 422 are substantially equal. In some configurations the second side between the fold points 421, 422 is thinner than the first side between the fold points 421, 422.

In some configurations, a ratio of the relative thicknesses between the (thicker) sides of the lateral cross section and the (thinner) fold points is in the range of about 1 to 8, or about 1.5 to 3.5, or the ratio of the thickest part of the lateral cross section to the thinnest part of the lateral cross section being the fold points is in the range of about 1 to 8, or about 1.5 to 3.5.

In some embodiments, a side 411(*i*) of the parallelogram cross section that rests against a user's face is thicker than other sides. For example, side 411(*i*) may be thicker than the adjacent side 411(*ii*) joined to side 411(*i*) by an obtuse angle of the parallelogram, and/or side 411(*i*) may be thicker than the adjacent side 412(*ii*) joined to side 411(*i*) by an acute angle of the parallelogram, and/or side 411(*i*) may be thicker than the side 412(*i*) opposite to side 411(*i*). In some embodiments, the ratio of the thickness of a thinner side of the cross section to the thickness of side 411(*i*) (i.e. the base of the cross section) is in the range of 0.3 to 0.7. In one preferred embodiment, the ratio is 0.5. For example, in one embodiment the base 411(*i*) of the parallelogram is about 1.4 mm and the thickness of the other sides is about 0.7 mm.

In some embodiments, the ratio of the length of the base (the side 411(*i*) in contact with the user's face) between an obtuse corner and an acute corner of the cross section and the thickness of the base is in the range of 4 to 6.

With reference to FIG. 8*b*, in some configurations the cross section of the collapsible portion comprises a tail portion 490, also referred to herein as ramp portion 490, extending from one or both corners 421, 422 of the section comprising acute internal angles. The tail portion 490 provides a ramp at the edge of the collapsed section, from the user's face onto a top of the collapsed section in the closed configuration. The ramp portion 490 thus provides a tapering or transitioning thickness at the edge of the collapsed section, allowing the seal of a mask to gradually compress from the user's face onto the collapsed section to provide an improved seal against the user's face and the collapsed portion of the conduit. In some configurations the cross section has reflective symmetry on a line 450 extending through the corners 423, 424 comprising an obtuse angle, for example such that the same ramp feature is provided at each corner 421, 422 comprising an acute angle.

In some embodiments, the tail portion tapers from a height of approximately the thickness of the side of the cross section that contacts the user's face to a reduced height, for example 0.5 mm or less, or may taper to a point. The height of the tail portion (where the tail portion connects to a side of the cross section, for example side 412(*ii*)) may be about 1 mm to 3 mm, or about 1 mm to 2 mm, or 1 mm to 1.5 mm, or about 1.2 mm. In some configurations the height of the tail portion may be similar to the thickness of the side of the cross section that contacts the user's face. In some configurations, the height of the tail portion may be similar to the thickness of the side of the cross section that contacts the user's face plus the thickness of the opposite side of the cross section (e.g. side 412(*i*)) that comes into contact with the side that contacts the user's face when the cross section is in a collapsed configuration. In some configurations the height of the tail portion is about the same as the height of the collapsed cross section. A ratio of the height of the tail portion and the thickness of the thinnest section of the cross section may be about 1.2 to 1.9.

The tail portion may have a length of about 2 mm to 6 mm, or about 10% to about 50% of the width of the collapsible cross section, or about 30% of the width of the collapsible cross section.

Figure 8C:
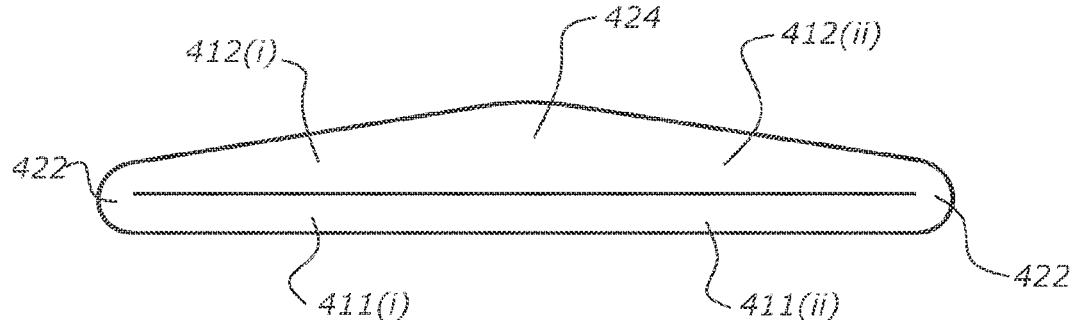
FIG. 8C illustrates a possible collapsed profile for the cross section of FIG. 8*a*.
Figure 8D:
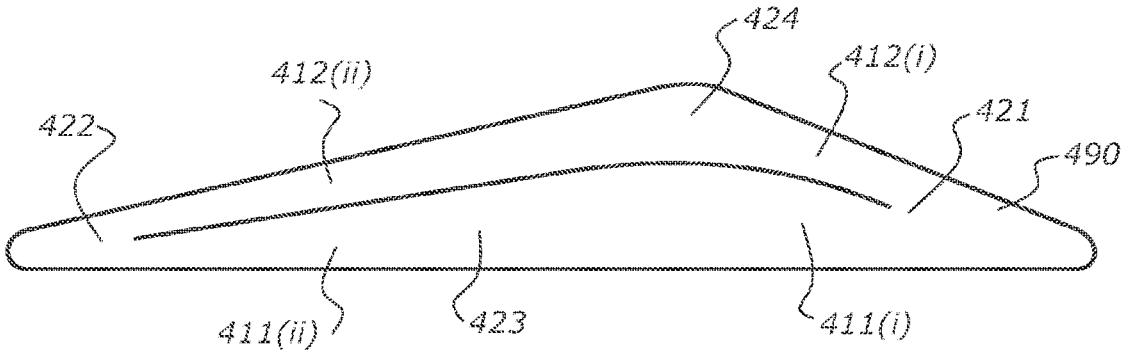
FIG. 8D illustrates a possible collapsed profile for the cross section of FIG. 8*b*.

In some embodiments, the collapsible portion may have a lateral cross section configured so that in a collapsed or closed configuration the cross section forms a profile that tapers from a deeper or thicker cross section to thinner section at the edges of the collapsed section, for example as shown in FIGS. 8*c* and 8*d*.

FIG. 8*c* represents a possible collapsed profile of the cross section of FIG. 8*a* or a cross section similar to that of FIG. 8*a*. FIG. 8*d* represents a possible collapsed profile of the cross section of FIG. 8*b* or a cross section similar to that of FIG. 8*b*. In some embodiments, one or both of the sides of the cross section may taper in thickness from each corner 421, 422 comprising an acute angle that form the fold points of the profile towards the corner(s) comprising an obtuse angle. Once collapsed the acute angle corners are located at the edges of the collapsed section. The tapering of the thickness of the side or sides from the acute angled corners to the obtuse angled corners creates a collapsed section that has a greater thickness in a portion in between the edges collapsed section, as shown in FIGS. 8C and 8D. In FIGS. 8*c* and 8*d* the tapering of the thickness of the sides from the acute to the obtuse angled corners is exaggerated to illustrate the concept of having a tapering thickness to achieve a tapering collapsed section. In FIG. 8*a*, the second side 412 of the cross section comprising two adjacent sides 412(*i*) and 412(*ii*) and corner 424 comprising an obtuse angle of the parallelogram tapers in thickness, from the corner 422 comprising an acute angle to the corner 424 comprising an obtuse angle. The thickness of side 412 is greatest at the obtuse angled corner. The resulting collapsed profile should taper in thickness from a maximum thickness at or adjacent to the corner 424 comprising a flattened obtuse angle towards the folded acute angled corners at the edges of the collapsed section. Similarly, in the cross section of FIG. 8*b*, the thickness of the side 412 tapers to be greater at the corner 424 comprising an obtuse angle.

As described above, in some embodiments, a side 411(*i*) of the parallelogram cross section that rests against a user's face may be thicker than other sides of the parallelogram, for example as shown in FIG. 8*b*. In a collapsed configuration, the cross section is thinner through the thinner adjacent sides 411(*ii*) and 412(*ii*) when collapsed together, and the cross section is thicker through the thicker side 411(*i*) and adjacent side 412(*ii*) when collapsed together. The thinner section through the thinner sides may provide a tapering of the cross section from the fold point 422 to the thicker section resulting from the thicker side 411(*i*). To provide a tapering of the thickness from the other fold point 421 of the collapsed section, preferably, the cross section has the ramp portion 490 at the acute angled corner at the thicker side of the cross section. The collapsible conduit of any one of the above described embodiments may be formed from any suitable material but in one preferred embodiment may be formed from a elastomeric/resilient material such as for example silicone. The material is substantially soft and is biocompatible. In some embodiments, the collapsible portion is formed so that a natural or undeformed cross section of the collapsible portion is the open configuration. The collapsible portion is elastically deformed to move from the open configuration to the collapsed configuration, by an external force applied to a side of the conduit. When the force is removed, the conduit returns to its undeformed open configuration due to the resiliency of the conduit material. Furthermore, the collapsible portion is biased to move from the collapsed configuration to the open configuration by an internal pressure of a gases flow within the conduit expanding the conduit to the open configuration.

The above described collapsible cross-sections may form only a portion of a length of a conduit. Remaining portions of the conduit may have relatively thicker wall sections or have a different cross-section (for example round) to prevent unintended collapse of portions of the conduit other than the collapsible portion. The shape and/or wall thickness may gradually change from a cross section in a non-collapsible portion to the cross section in the collapsible portion. In some embodiments the internal cross-sectional area (e.g. the cross sectional area of the lumen of the conduit) along the collapsible portion is similar to the cross-sectional area of the inspiratory tube 112 to avoid large changes in area that could lead to turbulence and an increased resistance to flow.

As described earlier, in some embodiments, a collapsible conduit or collapsing portion of a conduit may be integrally formed with and as part of a patient interface. An example of a nasal cannula 700 comprising a collapsible conduit portion is now described with reference to FIGS. 9A to 9H.

The nasal cannula 700 comprises a manifold portion 701, also referred to herein as manifold 701 from which nasal prongs 702, also referred to herein as nasal outlets 702, nasal prong 702, outlet 702, or prongs 702, extend. A side arm or member 703, 704, also referred to herein as left side member 703, right side member 704, extends from one or each side of the manifold portion 701. A collapsible conduit portion 704 may be integrally formed in or with a side member of the cannula. In some embodiments, a side member 703 is a conduit 705 for transporting a flow of gases from a patient conduit 112 to the manifold 701, e.g. the cannula comprises a conduit 705 extending from a side of the manifold 701. Substantially a full length of the conduit 705 may be configured to collapse, or a portion of the length of the conduit 705 may be configured to collapse.

In an embodiment where the cannula comprises a left side member 703 (left with respect to a patient) and a right side member 704, one or both side members may form a conduit for transporting gases to the conduit. Where both side members are conduits, two patient conduits 112 are provided, one conduit to a distal end of each side member. In some embodiments, as illustrated in FIGS. 9A to 9H, one of the side members 703, 704 may be configured as a conduit

705 and the other of the side members 703, 704 may be configured to collapse but in use to not provide a flow of gases to the manifold. With both the conduit 705 and the side member 704 configured to collapse, a face mask may be provided over the cannula with the cannula remaining on the face of the user. A seal of the face mask presses against a portion of each of the side member 704 and conduit 705 so that they collapse, allowing the seal of the face mask to form a satisfactory seal with the user's face and the cannula, as described earlier with reference to FIG. 3.

In some embodiments, the left and right side members 703, 704 may comprise the same cross section. For example, the side members 703, 704, whether used as a conduit or not, may have a collapsible cross section as described with reference to FIG. 6A. If both side members have the same cross section this may allow the members to exhibit the same collapsing behaviour when the user applies an even force onto the patient's face and thus a similar seal of the facemask over both cannula side members may be achieved. In some embodiments, each of the side members may be a conduit, and a plug 708, also referred to herein as plug 708 may be provided to a distal end of one side member and a conduit connector 707 may be provided to the distal end of the other side member, so that the cannula is configured as a single inlet cannula for use with a single patient conduit 112. The cannula may be configured to a dual inlet cannula by replacing the plug 708 with another connector to connect a second patient conduit. Alternatively, the cannula may be configured to a single inlet cannula with a patient conduit attached to the distal end of either the left side member or the right side member, and a plug attached to the distal end of the other one of the left and right side members. In other words, the cannula may be configurable between a left hand inlet and a right hand inlet cannula, by connecting a conduit connector and plug to the appropriate side member. In some embodiments, the conduit connector and plug and cannula side members may be configured so that the connector 707 and plug 708 may each be fitted to both the left and right side members, such that the cannula may be configured between a left or right inlet by swapping the connector and plug from the left and right side members.

Figure 9A:
FIGS. 9A to 9H show a nasal cannula.
Figure 9B:
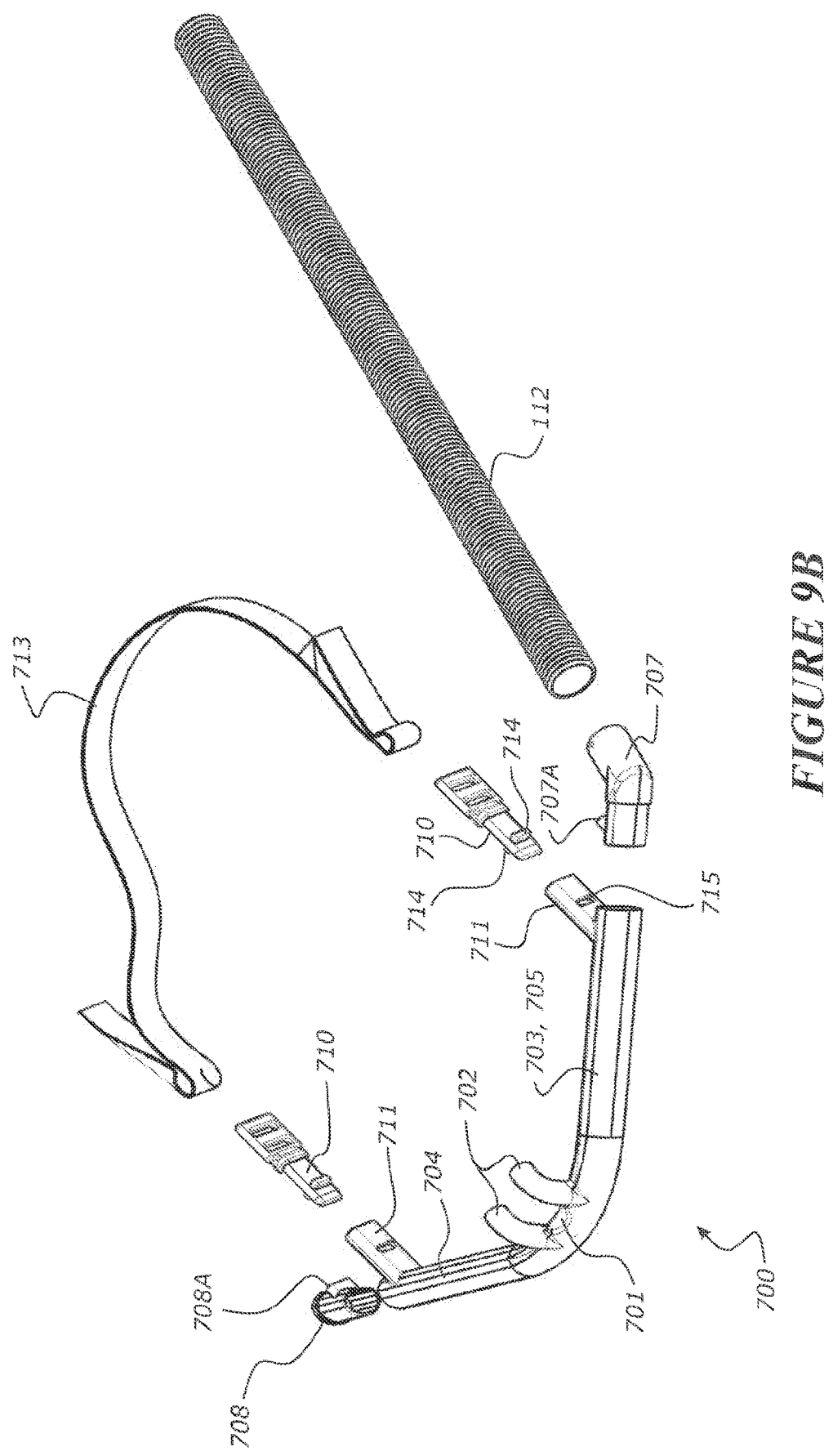
Figure 9D:
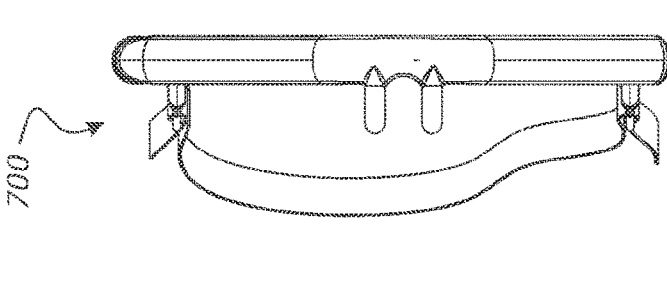
Figure 9C:
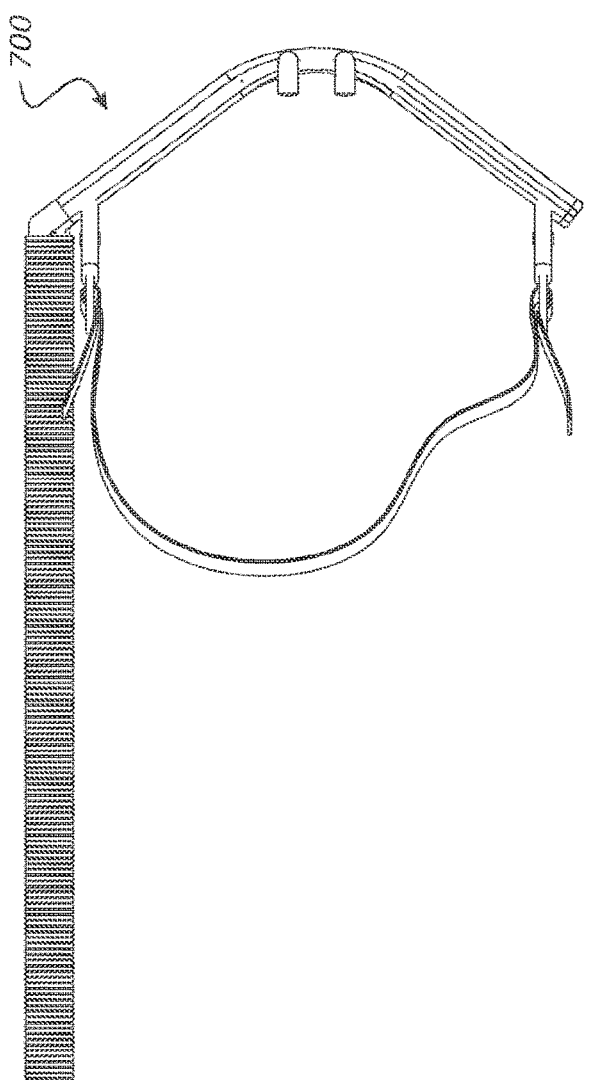
Figure 9E:
Figure 9E:
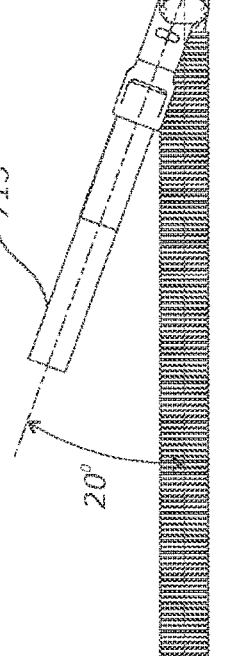
Figures 9F, 9G, 9H:
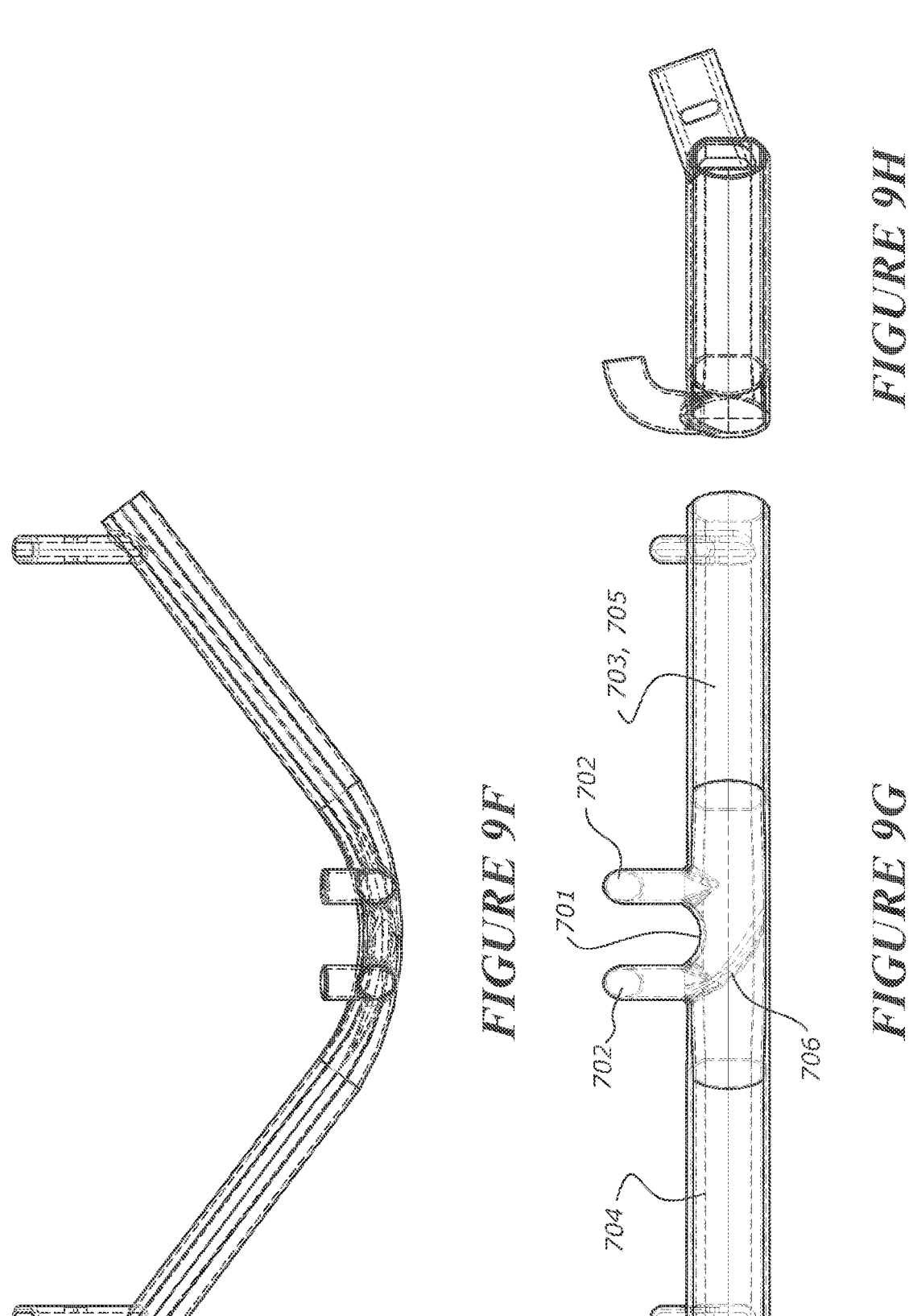

As best illustrated in FIG. 9G, in some embodiments, the cannula 700 may comprise a barrier or wall 706 to separate a lumen of one side member from a lumen of the other side member. In the illustrated configuration, the cannula is a single inlet cannula. However, the cross section of the two side members may be the same, but with only one side member used as a conduit to provide a flow of gases from the patient conduit 112 to the manifold 701. In some embodiments the wall is curved to assist with directing a flow of gases from the conduit 705 into the prongs 702. This may assist with reducing the resistance to flow compared to a sharp corner. Further, this wall may act as a rib to help keep the gas path open near the prongs and prevent kinking of the cannula (for example if the cannula is bent around a patient with a small or narrow face). The wall separates the lumen or interior volume of one side arm 704 from the other side arm 703. One side arm that is not in fluid communication with the nasal prongs 702 may have a relief hole or holes, so that the interior volume or lumen of the side member is open to the atmosphere, to allow air to escape from the interior of the side member as it is collapsed. Alternatively a relief hole may be provided in the plug 708, or no plug may be provided, e.g. the distal end of the side member may be left open. In some embodiments the interior volume of the side member not in communication with the nasal prongs may be in fluid communication with a user's exhaled breath, e.g. via a CO2 sampling tube, and a hole in the side member may be used to sample exhaled breath.

In some embodiments, the side members 703, 704 and manifold may be a unitary integrally formed member, for example from a thermoplastic elastomer (TPE), silicone or the like. In some embodiments, the side members 703, 704, manifold 701 and nasal prongs 702 may be a unitary integrally formed member. In some embodiments, the plug and/or conduit connector may be formed from a rigid material, for example HTPE, polypropylene, ABS, polycarbonate, or the like. The term rigid is used relatively with respect to the material that is used to form the side arms, which is substantially less rigid (more resilient or compliant to elastic deformation). A relatively more rigid plug or conduit connector may assist in maintaining the tube cross section in a normally open configuration. In some embodiments the side members may be formed separately to the manifold and attached or connected to the manifold. The manifold may comprise a relatively rigid material, to be more rigid that the soft or compliant side members.

In some embodiments, a headgear connector 712 is provided to each side member 703, 704. The headgear connector comprises a first part 710, also referred to herein as half 710, male connector part 710, or male part 710, and a second part 711, also referred to herein as female connector half 711, female connector part 711, or half 711, that releasably mate together. For example there may be a female connector part 711 and a male connector part 710 that releasably fit together. The female part 711 of the connector 712 may be formed of a resilient or flexible/compliant material, and the male part 710 may be formed from a relatively rigid material. In some embodiments, one of the connector parts may be attached to a side member of the cannula, and the other one of the connector parts attached to a headgear strap. In some embodiments, one of the connector parts may be integrally formed with a side member of the cannula, for example as illustrated in FIGS. 9A to 9H. In the embodiment of FIGS. 9A to 9H, a female part or half 711 of the headgear connector is integrally formed with a side member 703, 704, and a male part or half 710 of the connector is attached to a headgear strap 713. In such an embodiment the plug 708 and conduit connector 707 may pneumatically block an opening through the female connector half that would otherwise communicate with a lumen of the side members. For example, the plug and conduit connector 708, 707 each comprises a projection 708A, 707A that fits into an inside of the female connector half 711. The projection 708A, 707A may be a projection that is received in a recess within the side arm to assist retaining the plug or connector 708, 707 within the side member against a pulling force to remove the plug or connector.

As shown in FIGS. 10A to 10D, in some embodiments a headgear connector half 810, also referred to herein as headgear connector 810, headstrap connector 810, male connector half 810 or male part 810, is integrally formed with a conduit connector 807, hereinafter referred to as connector 807 or inspiratory tube connector 807, or plug 808 fitted/attached to a distal end of a side member 703, 704 of the cannula 800. Having the headgear connector 812 and the conduit connector 807 integrally formed together in one relatively rigid component may increase stability compared to an arrangement where the headgear connector and conduit connector are separately connected to the relatively soft cannula body.

Figure 10A:
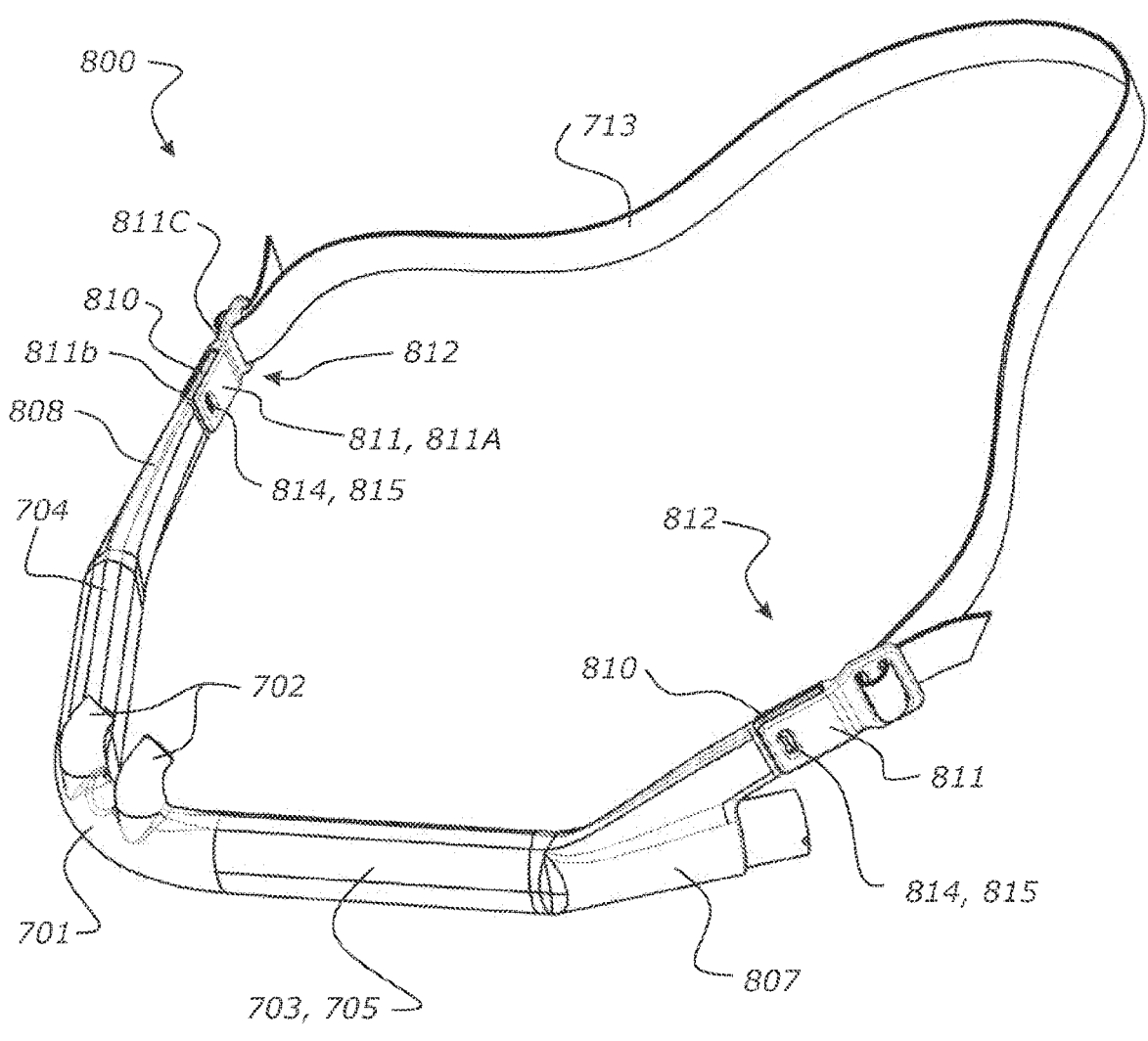
FIGS. 10A to 10D show a nasal cannula.
Figure 10B:
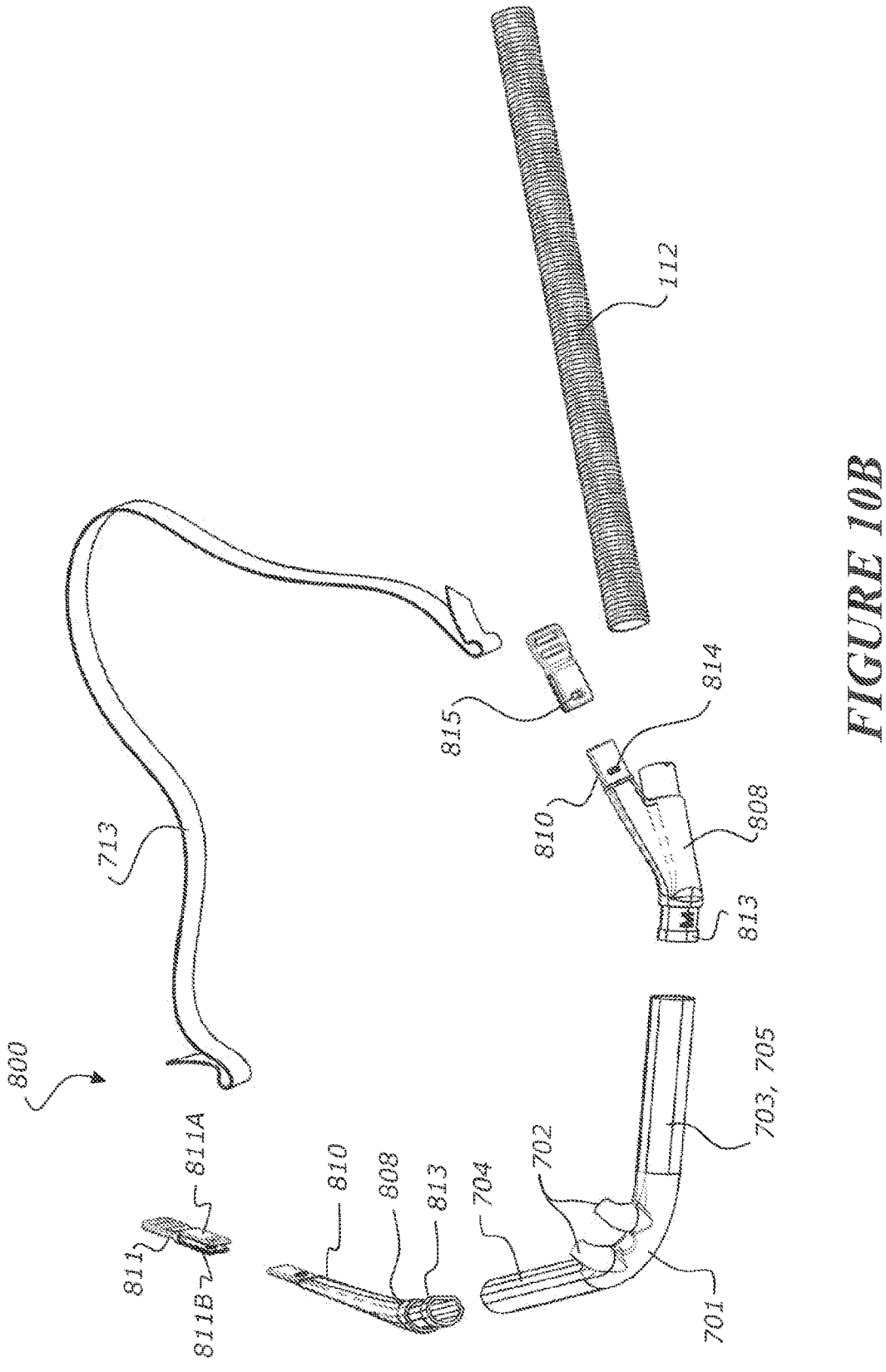
Figures 10C, 10D:
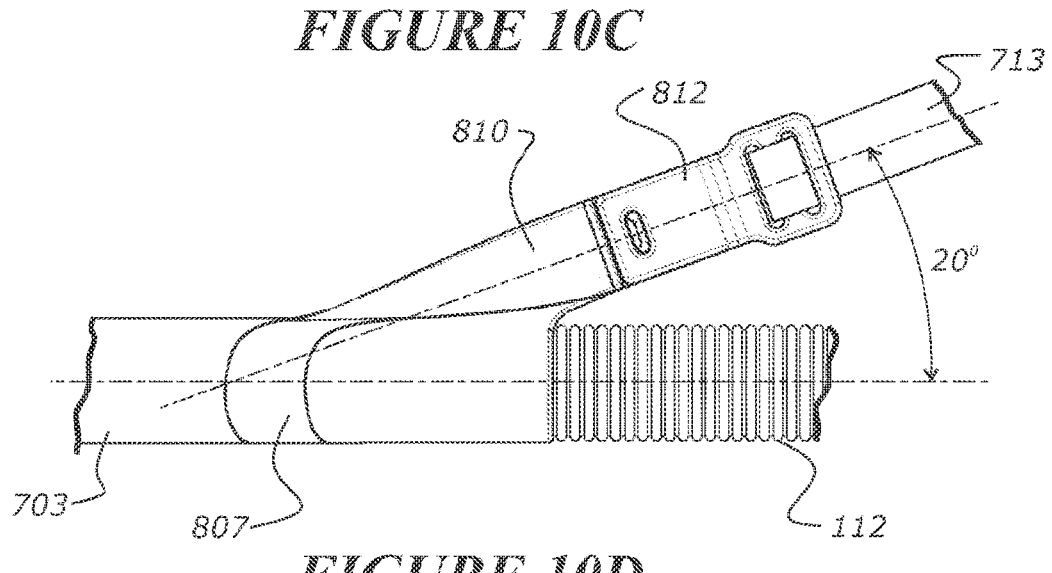

In FIG. 10C the cannula is illustrated with a conduit connector 807 fitted to both side members which in some embodiments can configure the cannula into a dual inlet cannula. In such an embodiment, a wall (e.g. like wall 706 in FIG. 9G) may be provided in the manifold 701 between the prongs 702, so that the prongs are pneumatically separate. A left hand prong or outlet 702 is provided a flow of gases via the lumen of the left hand side member 703, and a right hand prong or outlet 702 is provided a flow of gases via the lumen of the right hand side member 704. Alternatively both the left and right hand side members 703, 704 may be in fluid communication with both nasal outlets 702.

In some embodiments, as shown in FIG. 10B, the plug 708, 808 and/or the connector 707, 807 may comprise a raised rib 813 to be received in a corresponding recess within the side member (not shown) to retain the plug or connector within the side member. In the illustrated embodiment of FIG. 10B, the raised rib 813 is a continuous cannula rib or rim about the connector and plug, to fit in an annular recess within the side member. The rib or rim and corresponding recess may also act as a seal to prevent or minimise leakage of gases from the lumen of the side member between the side member and the connector/plug.

As shown in FIGS. 9A to 9H, and in FIGS. 10A to 10D, in some embodiments the female connector half 711, 811 may comprise an aperture 715, 815 to receive a lateral projection 714, 814 of the male connector half 711, 811 to secure the connector halves together. In some embodiments the male connector half 710, 810 has a lateral projection 714, 814 on each of two lateral sides of the male connector half, and the female connector half 711, 811 has two corresponding apertures 715, 815, each configured to receive a said lateral projection 714, 814. Alternatively, in some embodiments, the male connector part may comprise an aperture to receive a lateral projection of the female part. For example, the female part may comprise a lateral projection extending from one or each lateral internal side, to mate with a corresponding aperture in the sides of the male part. The male part may comprise an aperture that extends laterally through the male part and lateral projections of the female part may engage the aperture of the male part from either side. Each lateral projection 714, 814 preferably has a bevelled edge to deflect the lateral sides of the female part. This allows the parts to be easily connected when pushed together axially. In some embodiments the or each aperture 715, 815 is a slot oriented with a major axis lateral to a longitudinal axis of a headgear strap to be attached to the patient interface, as illustrated.

In the embodiment of FIGS. 9A to 9H, the female connector half is formed as a socket for receiving the male connector half. To disengage the two halves of the connector one half is pulled axially from the other, to remove the male connector half from the socket of the female connector half. When pulling the connector halves 710, 711 apart, the female half elastically deflects so that sides of the female connector half ride over the lateral projections of the male connector half to release the lateral projections 714 from the apertures 715 in the female half.

Figure 11A:
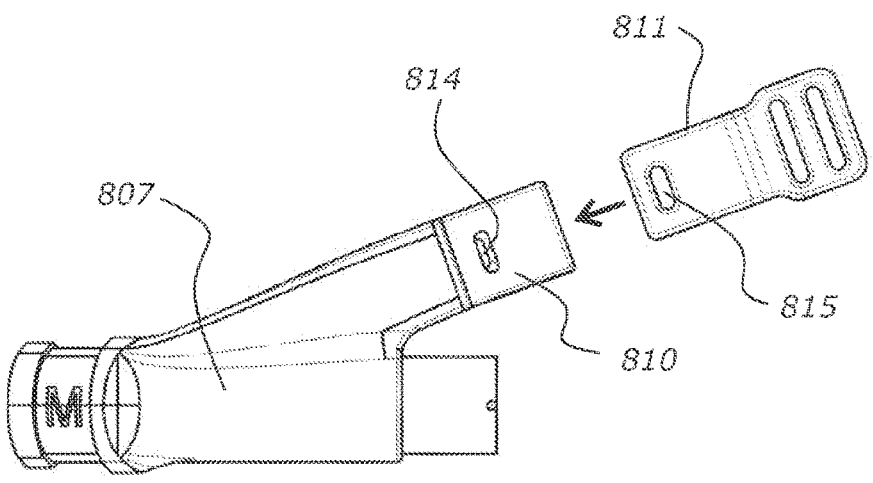
FIGS. 11A to 11D illustrate parts of a headgear connector engaging and disengaging.
Figure 11B:
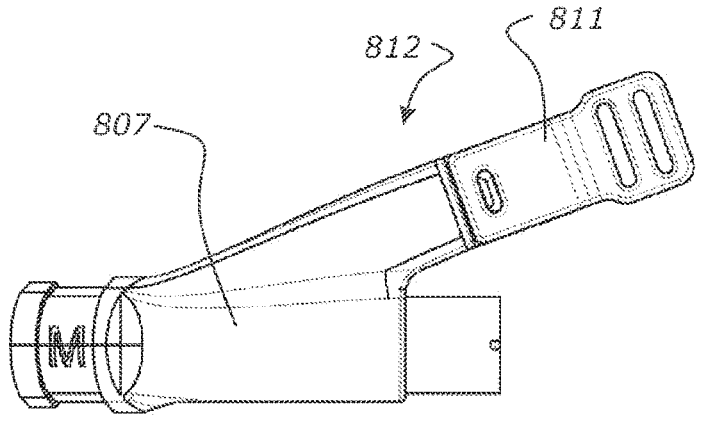
Figure 11C:
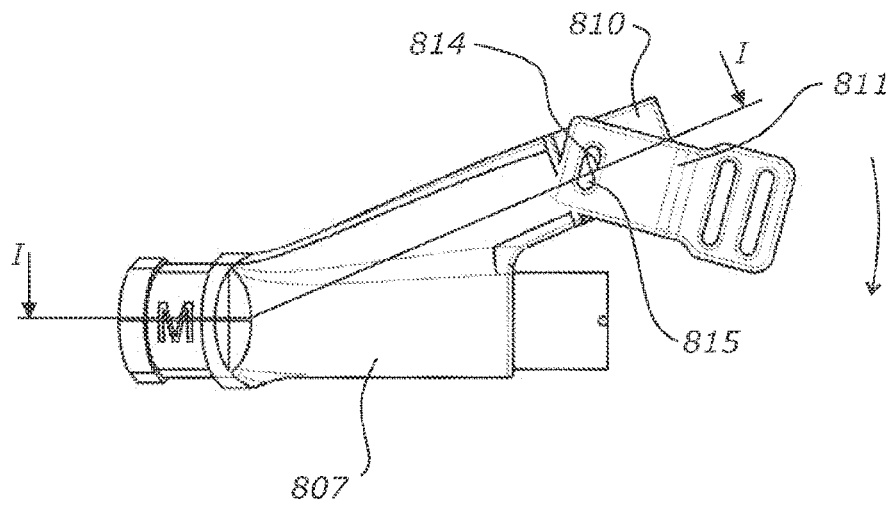
Figure 11D:
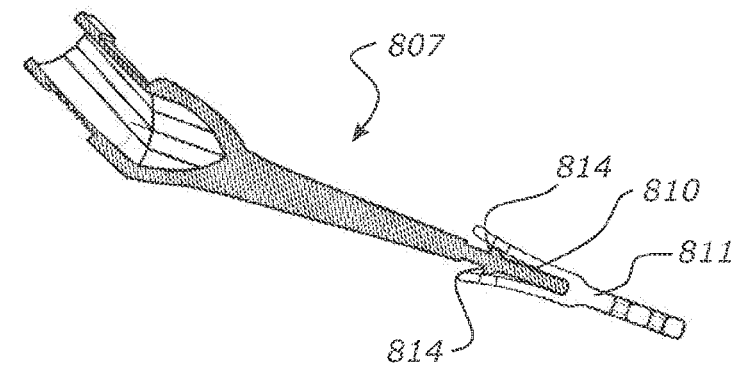

In the embodiment of FIGS. 10A to 10D, the female connector half 811, hereinafter referred to as female half 811 or female part 811, comprises two spaced apart tines or prongs 811A, 811B. The tines may form sides of the female part. The tines extend from a base 811C of the female connector half, such that a free end of each tine distal from the base may deflect laterally relative to the base. The way in which the connector halves 810, 811 are connected together and disconnected is illustrated in FIGS. 11A to 11D. As shown in FIG. 11A, to connect the two halves 810, 811 together, the halves are pushed axially together represented by the arrow in FIG. 11A, so that the male part is received between the tines of the female part. An axial direction is with respect to a direction that a headgear strap is to extend from the connector 812. When the halves are connected, the lateral projections 814 engage the apertures 815 in the tines, as shown in FIG. 11B. Pulling the halves axially apart can take a significant amount of force, to allow the tines to deflect and spread apart to ride over the projections 814. Under normal use, any axial force applied to the connectors, for example from tightening the headgear, is less than the axial force required to axially separate the connector halves. However, to disengage the female part 811 from the male part 810, the female part may be rotated about an axis lateral to the connector parts 810, 811 or lateral to the axial direction, e.g. lateral to a headgear strap extending from the connector 812, as represented by the arrow in FIG. 11C. The apertures 815 are shaped so that relative rotation between the male and female parts causes the projection to release from the aperture and deflect a said tine over the projection. For example, where the aperture is a slot and the corresponding projection is elongated to fit the slot, relative rotation between the parts causes the tines to spread as the projection interferes with an area of the tine around the slot. In FIGS. 11C and 11D, the female part is rotated so that the male and female parts are only partially engaged, with the tines deflected outwards to ride over the lateral projections, to disengage the female part from the male part. A force required to rotate the female part relative to the male part is reduced compared to a force required to separate the parts axially, because the projections 814 and corresponding apertures 815 are elongated with a major axis aligned perpendicular to the length direction of the head strap. With the major axis of the apertures and projections perpendicular to the strap an area over which an axial force may act is increased, creating a more secure attachment. The tines configuration of the female connector therefore achieves a connector that is secure in an axial direction on which forces in the headgear strap are aligned, yet allows for a relatively easy or reduced disconnection force by relative rotation between the male and female parts 810, 811. Relative rotation of the male and female parts does not occur in normal operation, other than when rotated by a person wishing to disconnect the headgear from the interface, and thus the described arrangement prevents or reduces accidental detachment. This configuration therefore allows for easily release of the cannula from the headgear which may assist in reducing the difficulty in removing the cannula from a user's face. Further, the female half 811 may be disengaged from the male half by a user singlehandedly, by simply twisting the female part relative to the male part. In another embodiment, the apertures and projections may be circular, with another feature such as complementary ramps or cam surfaces on the male and female parts arranged so that relative rotation between the parts cases the tines to spread apart to disengage each projection from the corresponding aperture.

To create an effective seal between a mask 300 and the cannula 700, 800 and the user's face, it may be desirable to have a section of the cannula side member or conduit that extends across the mask seal positioned on softer parts of the user's face. Correspondingly, it may be desirable to avoid hard parts of the patient's face. This may allow the user's face to deform around the cannula, to increase the chance of achieving an effective sealing of the mask seal over the cannula and with the user's face. Positioning the cannula on soft parts of the user's face may also help to improve patient comfort by not applying pressure on bony/hard parts of the user's face such as cheekbones. In general, it may also be comfortable to have other cannula components, such as head straps, lying on soft parts of the face.

Figure 12A:
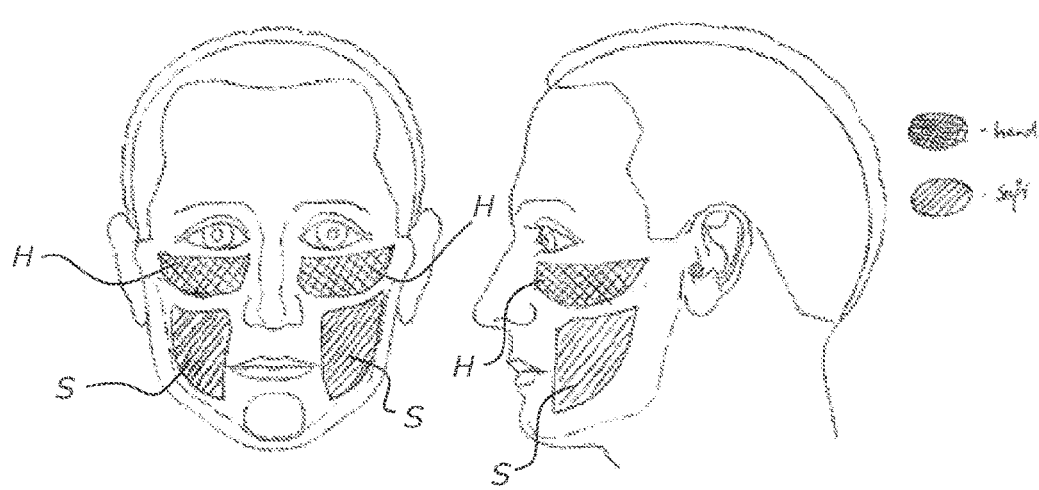
FIGS. 12A and 12B illustrate soft portions of a user's face.
Figure 12B:
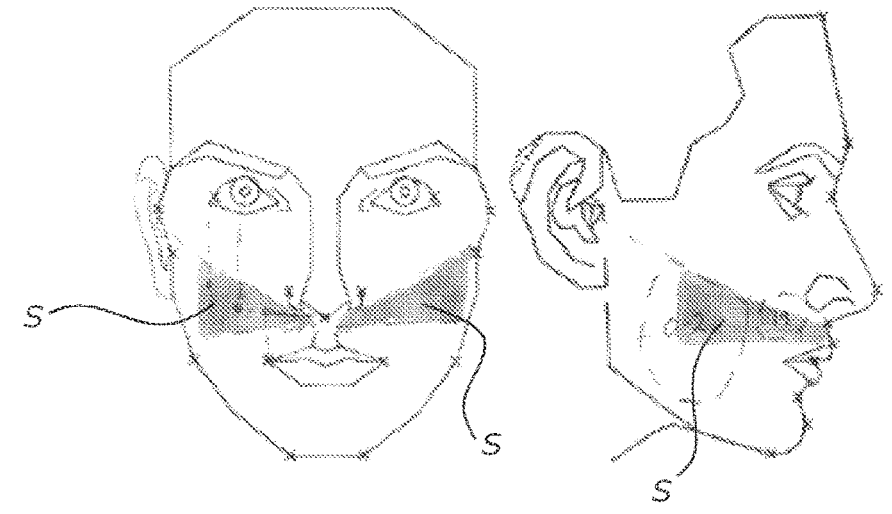
Figure 12C:
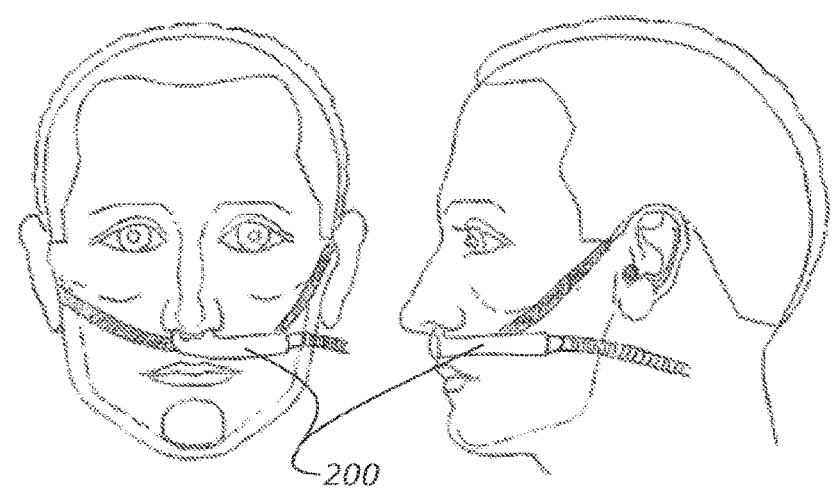
FIG. 12C illustrates a cannula positioned across a soft portion of a user's face.

FIG. 12A illustrates relatively soft areas S compared to relatively hard areas H of a user's face. FIG. 12B further highlights the soft areas S of the user's face, which may be described as an area bounded by a line extending from the bottom of the users nose to a centre area of the user's ear, and a line running from a user's upper lip (bottom of the philtrum) approximately horizontally with the user in a standing position, e.g. above the user's lower jawbone. As shown in FIG. 12C, preferably the cannula is positioned in the softer area of the user's face.

In order to position the cannula side members in a softer area of the user's face, in some embodiments the cannula is arranged so that the headgear strap extends from the side members at an angle to the side members when the cannula is viewed from a side of the cannula. For example, the angle may be 10 to 30 degrees, or 15 to 25 degrees, or about 20 degrees. In FIGS. 9E and 10D the headgear strap 713 is shown to extend from the side members of the cannula at an angle of about 20 degrees. To position the headgear strap at the desired angle, the headgear connector is preferably oriented at the desired angle. For example, in FIG. 9E, the female connector half 711 is integrally formed with the side member at an angle to the side member to orientate the strap correctly to the cannula. In FIG. 10D, the male connector half 810 is integrally formed with the conduit connector 807 at an angle to the side member with the conduit connector attached to the side member to orientate the strap correctly to the cannula 800. In the embodiments of FIG. 9A to 9H and 10A to 10D, the angle of the strap is positioned to locate the cannula approximately horizontally across the user's face (when the user is in a standing position) and with the headgear strap extending above the user's ears. As the head strap is directed over the patient's ears, the medical practitioner can apply a jaw thrust to the patient without obstruction. As shown in FIG. 10D, the conduit connector 807 is arranged so that the conduit 112 extends from the cannula in line with the side member 703. Also, as shown in FIG. 10C, in plan view, the angle of the conduit connector 807 and the headgear connector 812 relative to the side member 703, 704 are the same (or are similar) such that the conduit extends in line with the headgear strap in plan view. The arrangement of the conduit connector relative to the side member and headgear connector forces the inspiratory tube to lie alongside the patient's face when he or she is lying on his or her back. This configuration controls where the weight of the inspiratory tube lies and reduces the chance of the weight of the inspiratory tube kinking the collapsible portion of the cannula.

The cannulas 700, 800 described above are again illustrated in FIGS. 13A and 13B, with some indicated geometries (in FIG. 13B the conduit connector 707 and plug 708 are omitted). In the Figures, and including in FIGS. 13A and 13B, the cannula is illustrated in an unbent or un-deflected configuration, (e.g. a neutral or relaxed state). In some embodiments, in plan view, there is an obtuse angle between the side members. In some embodiments the angle between the side members is in the range of 100 to 130 degrees, or about 100 to 120 degrees, or about 100 to 110 degrees, or about 105 degrees. In the illustrated embodiments the angle is 106 degrees. Such an angle allows the cannula to contour around the user's face without the manifold or side members kinking. In particular, this angle may be equal to or greater than the angle that is required to conform the cannula to a typical adult's face. In this case the cannula will lie on the face or may be slightly bent or deformed inwards to conform to the user's face as the headstrap is tightened. Bending the cannula inward (i.e. around the user's face) is much less likely to kink the flexible cannula than bending the cannula outward (i.e. away from the user's face, such as when a smaller angle is used). A large angle is also particularly useful to fit patients who receive this therapy who are likely to be high BMI and thus have larger head circumferences.

In some embodiments, in a plan view of the cannula, a distance between distal ends of the side arms, and/or between the pair of headgear connectors 712, 812 (distance X in FIG. 13B), is about 100 mm to 150 mm, or about 110 mm to 140 mm, or about 110 mm to 130 mm or about 120 mm. This distance is a sufficient width for a non-invasive ventilation mask to overlay the cannula with the edges of the seal falling within X (a non-invasive ventilation mask may typically have a width of approximately 100 mm). In some embodiments, the connector 807 is relatively rigid and is positioned as close as possible to the prongs 702, while still allowing for the collapsible portion to be long enough for a mask to fit over (dimension X). Such an arrangement may improve comfort, as having the connector 807 as close as possible to the prongs (i.e. to the centre of the user's face) positions the connector away from the side of the patient's head so that with the patient lying on his or her side the connector may not be directly under the patient's face between the patient's head and pillow.

Figure 13A:
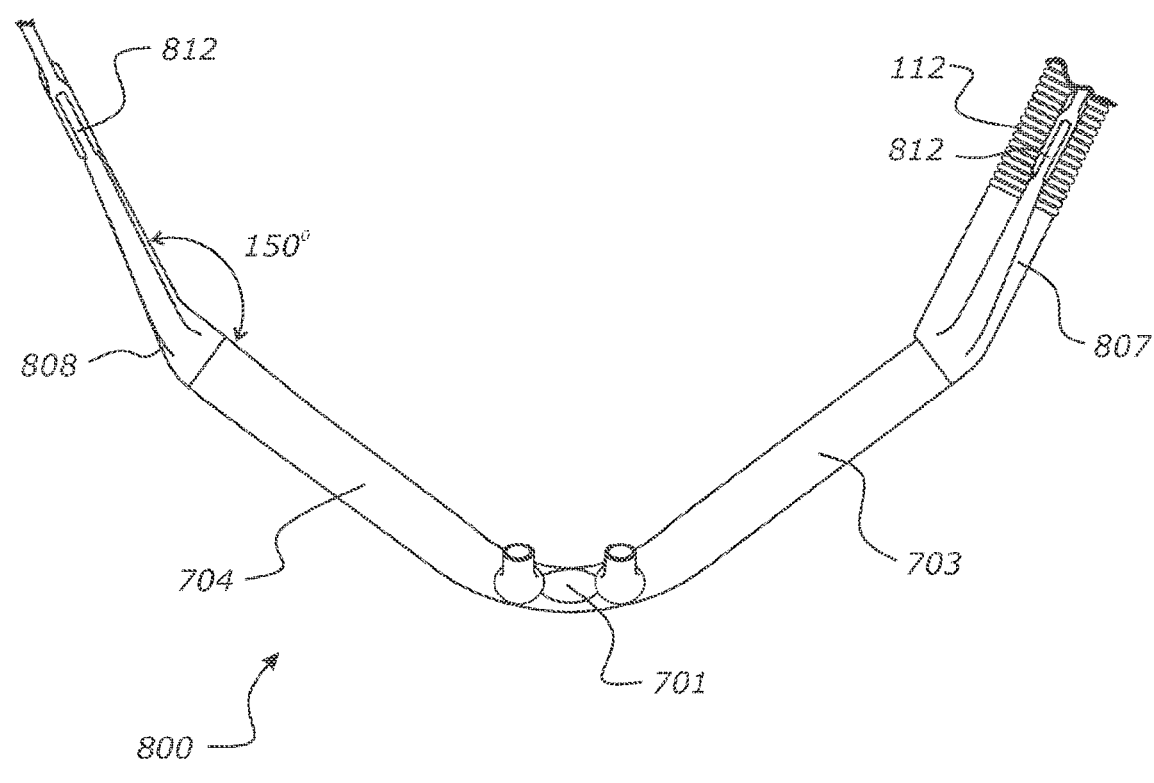
FIGS. 13A and 13B illustrate geometries of two embodiments of a cannula.
Figure 13B:
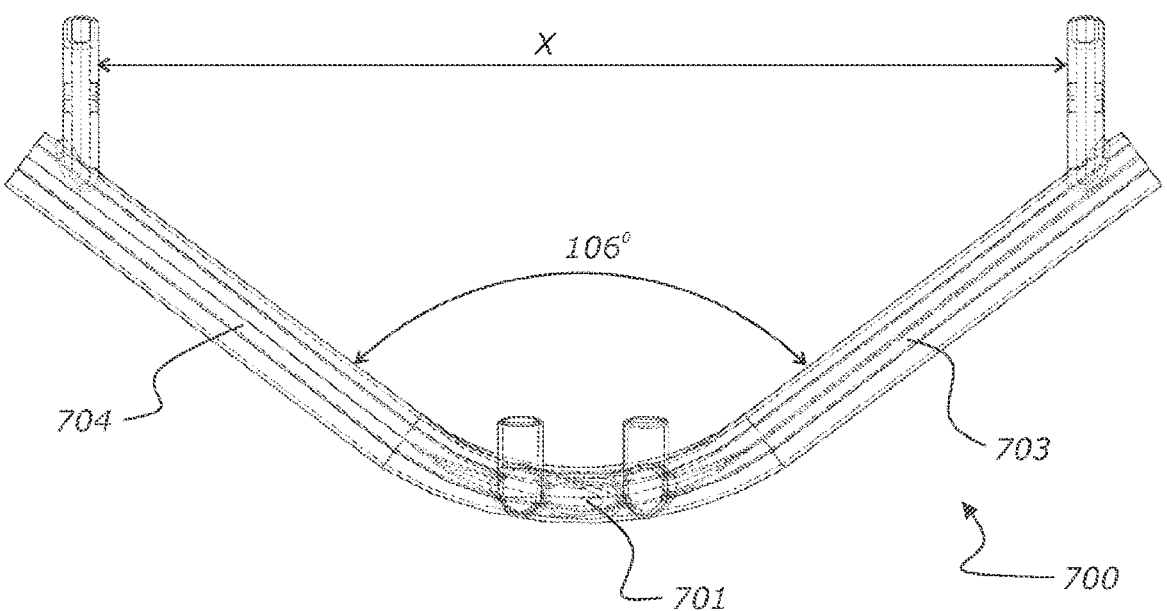

In some embodiments, in plan view there may be an obtuse angle between the headgear connector and the side arm. For example, as shown in FIG. 13A, the cannula 800 comprises an angle of about 150 degrees between the headgear connector 812 and the side members 704, 703. In some embodiments this angle may be in the range of 130 degrees to 170 degrees, or 140 degrees to 160 degrees, or 145 degrees to 155 degrees.

The above described geometries and arrangements may provide a number of benefits. Having the cannula horizontal across the face under the nose means the collapsible portion of the cannula intersects the facemask seal at a perpendicular angle and so the area over which the seal acts is as small as possible, reducing the required force to cause the collapsible portion to collapse. Further, a horizontal section encourages the cannula to lie in the soft sections of the face as the soft area just next to the nose is relatively small. The described arrangements may reduce the risk of the cannula and/or conduit 112 angling up towards the user's ears and lying across the user's hard cheekbone. The obtuse angle between the inspiratory tube and the cannula conduit described above removes sharp (sudden) corners in the gases flow path which can lead to turbulence and increase resistance to flow. The arrangement also aligns the conduit connector 807 close to the user's face to reduce leverage from the weight of conduit 112 which could cause kinking of the cannula. In some embodiments, the conduit connector 807 could be angled inwards towards the user's face for even closer positioning of the conduit to the face. For example, in FIG. 10C the conduit connector is arranged approximately parallel to a sagittal plane of the user, whereas in some embodiments the connector 807 could be angled in inwards by 15 degrees relative to the sagittal plane. As described above, the headstrap connector 810 and the conduit connector 807 may be substantially in the same plane (vertically above) to reduce leverage from the weight of conduit which could cause kinking of the cannula. In some embodiments, the headgear connector 810 may be centred over the inspiratory tube connector 807 also to reduce leverage from weight of conduit which could cause kinking.

Figure 14A:
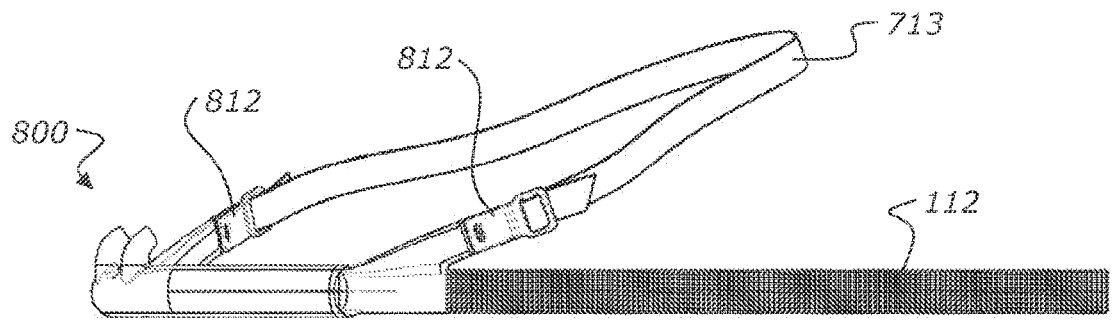
FIGS. 14A to 14B illustrate a cannula with alternative headgear.
Figure 14B:
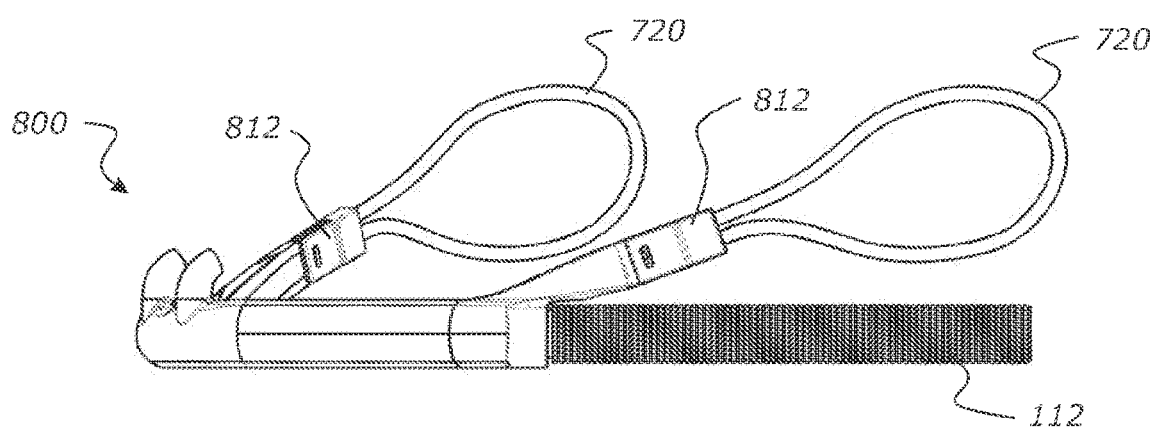
Figure 14C:
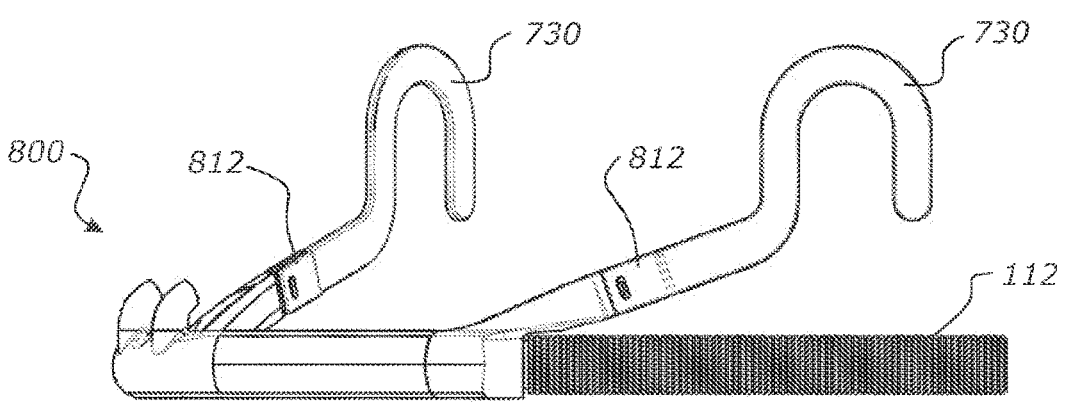

FIGS. 14A to 14C illustrate alternative headgear. In FIG. 14A, the headgear comprises a strap 713. In FIG. 14B, the headgear comprises a pair of elastic loops 720, each loop configured to loop around an ear of the user. In FIG. 14C, the headgear comprises a pair of arms 730 similar in function the arms of a pair of spectacles. The arms 730 preferably extend down past the back of the ears to ensure secure retention of the cannula to the user's face. The described headgear may all have identical connectors and so be interchangeable as the user or patient desires. A headgear 720, 730 that does not go around the back of the patient's head may be particularly advantageous if the clinician does not wish to move the patient's head to apply or remove the cannula, or to prevent the patient's hairnet being removed by the headstrap or the patient's hair becoming tangled in the headstrap. All headgear may be adjustable for different patient sizes (e.g. the elastic loops 720 may be pulled through the connector 812 to tighten).

Figure 15:
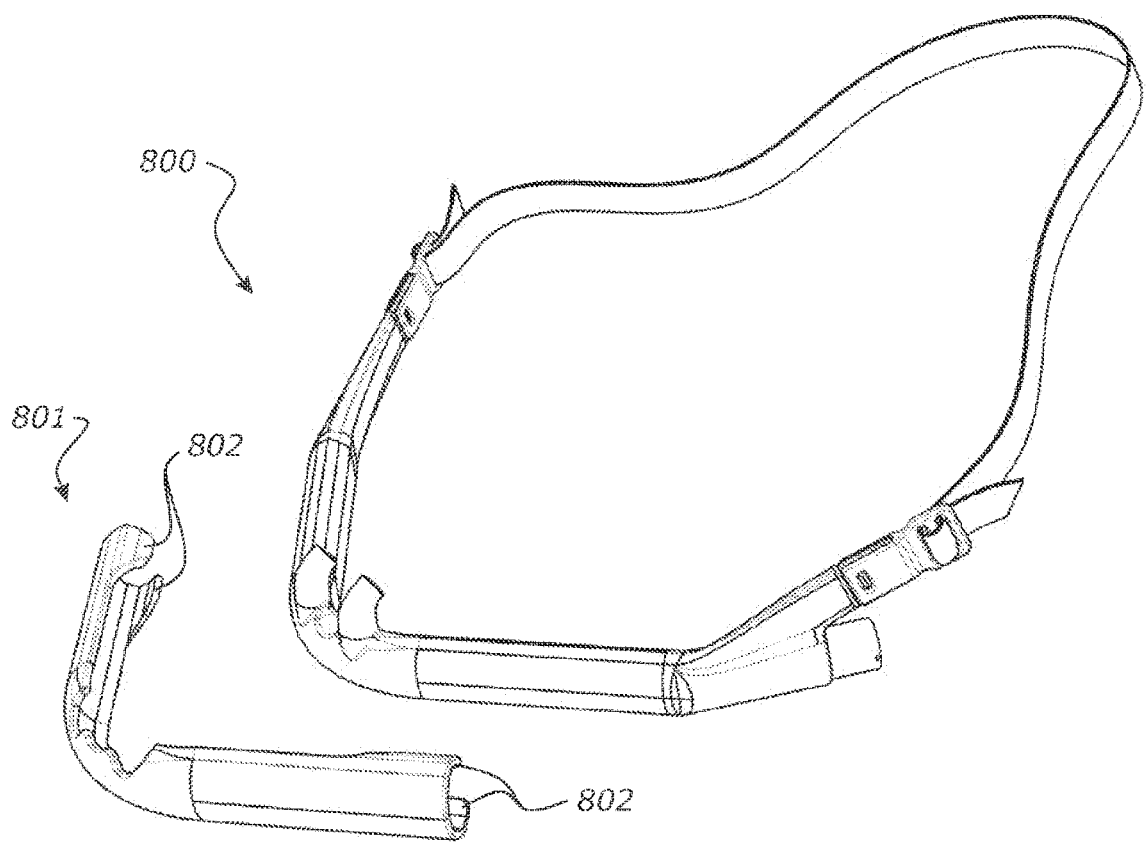
FIG. 15 is a perspective view of a cannula and a shield configured to attach to the cannula to support the cannula against collapse.

In some embodiments the cannula 700, 800 may be configured to be used without collapsing, by providing a shield or support member (e.g. a frame) to fit over and/or cover a side member, or both side members and the manifold. For example, as illustrated in FIG. 15, a removable shield 801, hereinafter referred to as shield 801 or frame 801, may be provided to fit over the side members and manifold. The shield 801 may be formed from a relatively rigid material to support the cannula against collapse, for example against collapsing as a result of an external force applied to the cannula. The shield may comprise one or more (e.g. two) pairs of jaws 802 that are configured to grab around a portion of the cannula side arm or manifold or the plug or conduit connector to hold the shield to the cannula. In the illustrated embodiment the shield comprises a pair of jaws at each end of the shield, each pair of jaws configured to grip around a portion of a corresponding side member. The cannula may comprise a cannula body formed of a relatively flexible material, the cannula body comprising the manifold and at least one nasal prong or outlet, and a side member extending from each side of the manifold, as described earlier. The shield or frame is formed of a relatively rigid material (compared to the cannula body material). The shield attaches to the cannula body, to support the cannula body against collapse of the side arms.

In the above described cannula, in preferred embodiments, the cannula is 'slim' to reduce the size of the interface on the patient's face. Also, the relatively rigid headgear connector 712, 812 is slim to reduce bulk between the patient and a pillow supporting the patient's head when the patient is lying on his or her side to improve patient comfort.

FIGS. 16A to 16E illustrate a further embodiment of cannula 900 comprising a cannula body 935 formed of a relatively flexible material and a frame 950 formed of a relatively rigid material. The cannula body 935 comprises a manifold 901 and at least one nasal prong or outlet 902, and a side arm or member 903, 904, also referred to herein as left hand side member 903, left side member 903, right hand side member 904, right side member 904, extending from each side of the manifold, as described earlier. A left side member 903 extends from a left side of the manifold and a right side member 904 extends from a right side of the manifold. Each side member comprises a lumen to provide a conduit for a flow of gases from an inlet of the cannula to the manifold. In some embodiments the conduit of each side arm comprises a collapsible portion as described in earlier embodiments. The frame 950 is attached to the cannula body 935 and may prevent collapse of the cannula body and conduit. In some embodiments, the frame 950 supports the cannula body 935 but allows for the body 935 to collapse when a force is applied to a front surface of the frame 950, to occlude the lumen. The frame 950 may be adapted to deform elastically so that a force applied to the front of the cannula frame 950 bends the frame and collapses a side member 903, 904 and lumen of the cannula body. Once the force is removed from the frame the frame 950 and cannula body 935 return to an un-collapsed configuration. Alternatively, in some embodiments, the frame 950 can act as a strut or support for the cannula body 935 to prevent collapsing of the cannula body. The frame can be used with the body in procedures where collapsing of the cannula is undesirable. The frame may be removably attachable to the body.

The cannula body 935 may comprise a gases inlet portion 924 to a lumen of the cannula body. The gases inlet portion 924 may be located at or towards an end of a side arm 903, 904. As illustrated, in some embodiments the cannula comprises a gases inlet portion 924 at each side arm 903, 904. The frame 950 may comprise an inspiratory tube connector 925 to attach an inspiratory tube 112 to the cannula. In some embodiments, the inspiratory tube connector 925 receives the gases inlet portion 924 of the cannula body. When gases are supplied to the cannula 900, a pressure of the gases forces the gases inlet portion 924 (e.g. inflates the inlet portion) against an inside of the inspiratory tube connector 925. An outer surface of the gases inlet portion 924 contacts an inner surface of the inspiratory tube connector 925 to create a seal to substantially prevent gases leaking.

Figure 16A:
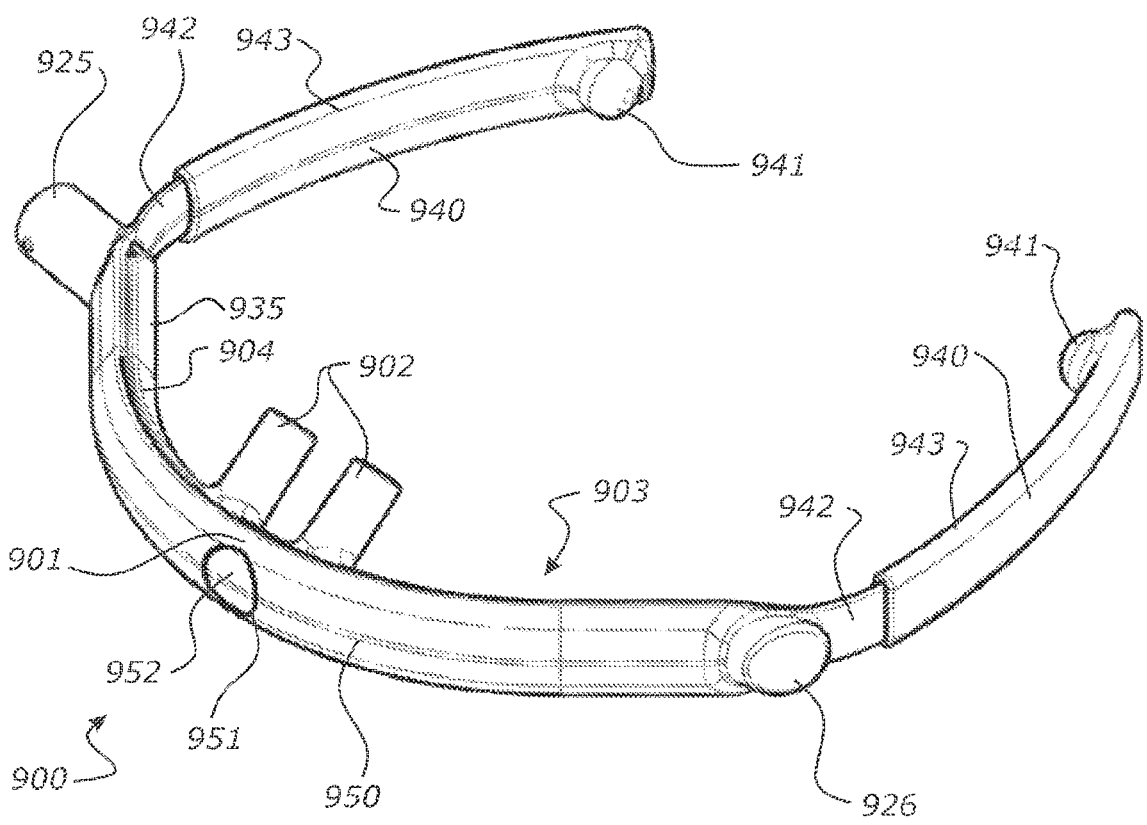
FIGS. 16A to 16E show a nasal cannula.
Figure 16B:
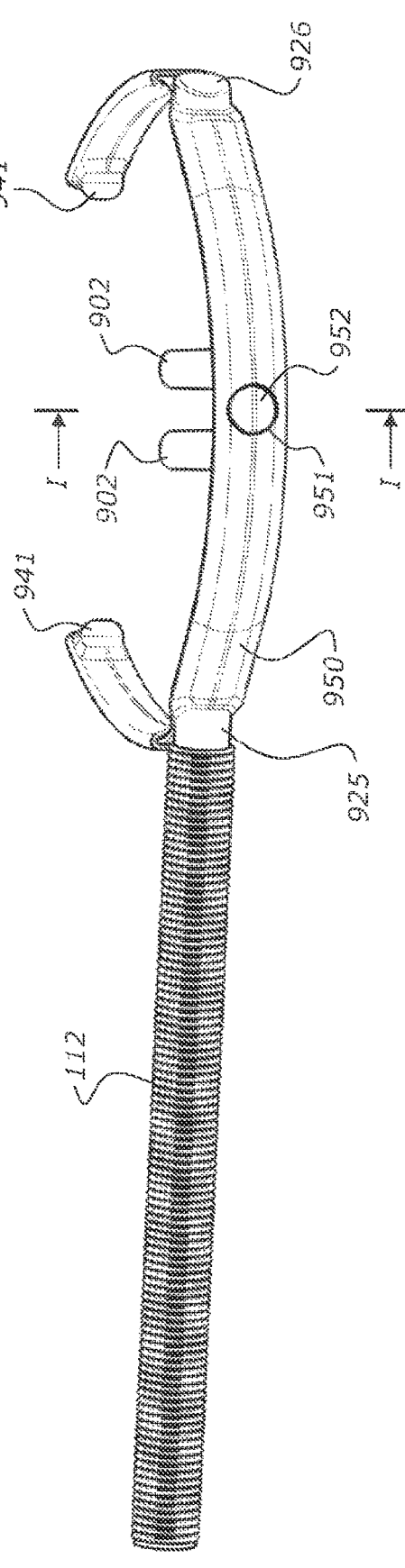
Figure 16C:
Figure 16D:
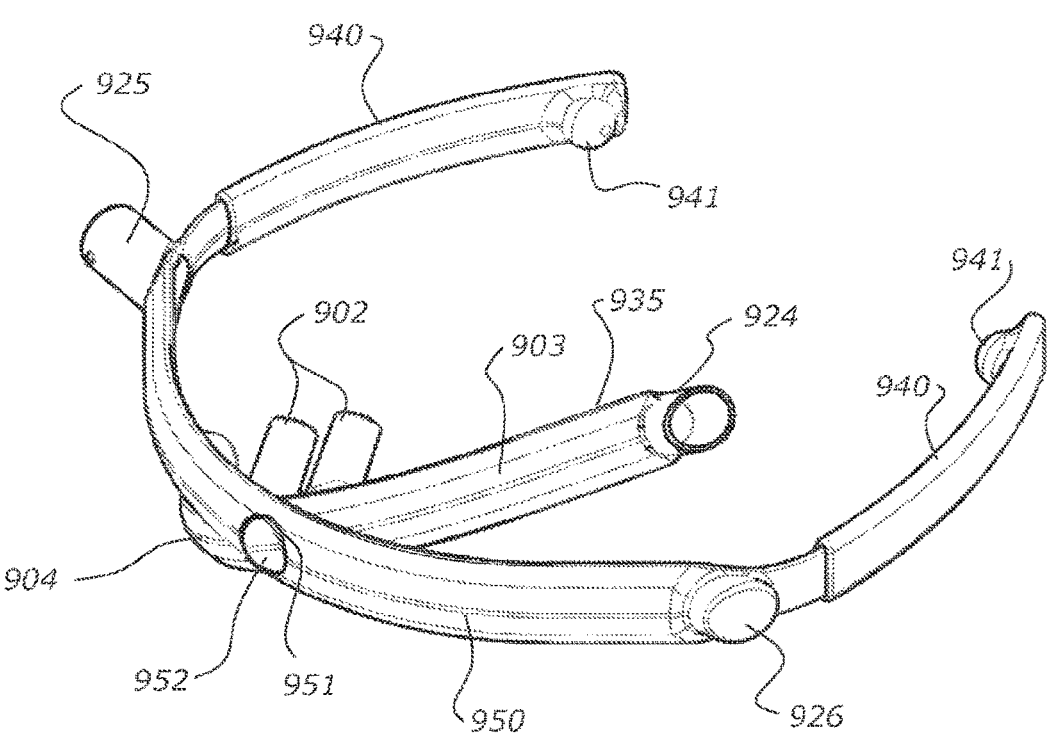

The cannula body 935 and frame 950 are movably attached together. For example, in some embodiments, the frame 950 may be pivotally (rotationally) attached to the cannula body 935, so that the frame may be rotated relative to the cannula body. In the illustrated embodiment, the cannula body may comprise a post 952 and the frame may comprise an aperture 951, also referred to herein as recess 951, for receiving the post, the frame 950 rotating on the recess 951 about the post 952. The post may be formed of a relatively rigid material compared to the material generally forming the cannula body. The post may be overmoulded into the softer or resilient material of the cannula body. In an alternative configuration the cannula body 935 may comprise an aperture or recess to receive a post of the frame 950. In some embodiments, the cannula body comprises a gases inlet portion 924 at each side arm 903, 904 (e.g. towards or at an end of each side arm). The frame comprises an inspiratory tube connector and a blanked hollow projection 926, also referred to herein as recess 926 (e.g. a blanked tubular projection). The inspiratory tube connector 925 is adapted to receive a said gases inlet portion 924 of the cannula body 935. When gases are supplied to the cannula 900, a pressure of the gases within the cannula forces the gases inlet portion 924 (e.g. inflates the inlet portion) against an inside of the tube connector 925. An outer surface of the gases inlet portion contacts an inner surface of the tube connector to create a seal to substantially prevent gases leaking from between the tube connector 925 and the cannula body 935. Similarly, the hollow projection 926 is adapted to receive a said gases inlet portion 924 of the cannula body 935. When gases are supplied to the cannula, a pressure of the gases within the cannula forces the gases inlet portion 924 (e.g. inflates the inlet portion) against an inside of the hollow projection 926. An outer surface of the gases inlet portion 924 contacts an inner surface of the hollow projection 926 to create a seal to substantially prevent gases leaking. Rotation of the cannula body 935 relative to the frame 950 selectively configures the cannula 900 between a left hand conduit inlet and a right hand conduit inlet. FIG. 16D illustrates the frame rotated relative to the cannula body partway between the left and right hand configurations. Alternatively or additionally, the frame 950 may be removably attached to the body 935 and attachable to the body in two orientations, a first orientation providing a left hand inlet and a second orientation providing a right hand inlet. The cannula is configured as a left hand inlet cannula when the gases inlet portion 924 at the left hand side member 903 of the cannula body is received in the inspiratory tube connector 925 of the frame and the gases inlet portion 924 at the right hand side member 904 of the cannula body is received in the hollow projection 926 of the frame 950. The cannula is configured as a right hand inlet cannula when the gases inlet portion 924 at the right hand side member 904 of the cannula body is received in the inspiratory tube connector 925 of the frame and the gases inlet portion 924 at the left hand side member 903 of the cannula body is received in the hollow projection 926 of the frame 950 (as illustrated in FIG. 16A).

In an alternative embodiment, the cannula body may include a pair of gases inlet portions 924, each located at or towards a distal end of each side arm, and the frame comprising a pair of inspiratory tube connectors 925 located at opposing ends or located at opposed sides of the frame to correspond with and receive one of the pair of gases inlet portion 924 so that the cannula is configured for use as a dual entry cannula. A pair of inspiratory tubes may be attached to the pair of tube connectors 925 to supply gases to the cannula.

Figure 16E:
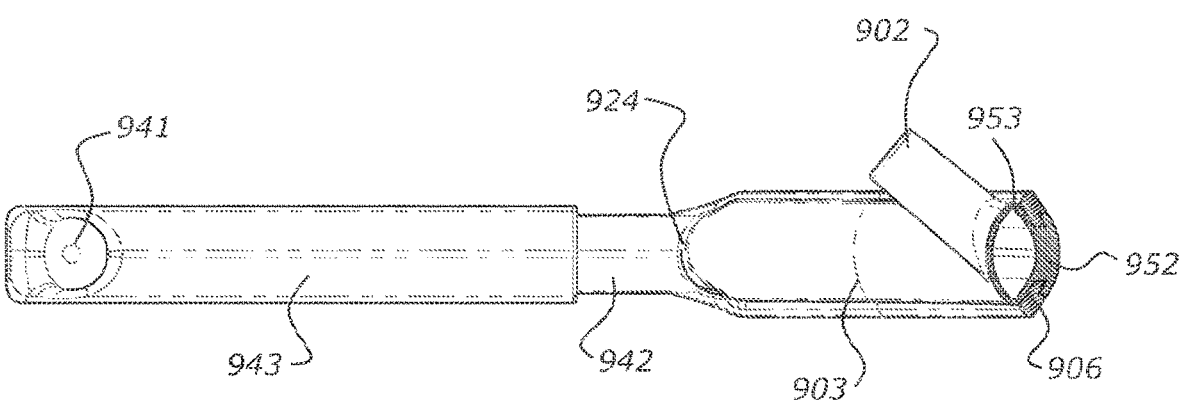

As illustrated in FIG. 16E, the frame 950 may comprise a concave rear side 953 (the side that faces towards a user's face in use to receive the cannula body 935. A front 906 of the cannula body (facing away from the user's face in use may be complementarily convex to fit within the frame.

As illustrated by example in FIGS. 16A to 16E, in some embodiments a patient interface comprises a headgear, the headgear comprising a pair of ear plugs 941. Each ear plug 941 is adapted to fit within a user's ear, to retain the cannula 900 in position on the user's face. The headgear may comprise a pair of arms 940, each ear plug provided on a respective said arm. One or both arms may be length adjustable. For example, one or both arms may comprise a telescopic configuration. One or both arms may comprise two or more parts that are arranged in a nested, telescoping configuration. In the illustrated embodiment, each arm comprises a first portion 942 slidingly received in a second portion 943, relative movement between the first and second portions achieving a variable length. This allows the interface to be easily sized for different patients. The arms may include a telescoping configuration with a ratchet assembly. The ratchet assembly may include a locking mechanism adapted to lock the telescoping arms one or more predetermined positions. For example the locking mechanism may comprise a moveable latch movably secured to one part 942, 943 of an arm to movably engage a series of grooves or apertures in another part 943, 942 of the arm. As shown, in some embodiments the patient interface is a nasal cannula. One of the first and second portions 942, 943 of each arm 940 may be integrally formed with a side of the cannula. In the illustrated embodiment, the first portion 942 of each arm 940 is integrally formed with the frame 950 that is attached to the cannula body 935. One of the first and second portions 942, 943 of the arms 940 may be more rigid than the other one of the first and second portions of the arms. For example, the first portion 942 received in the second portion 943 may be more rigid than the second portion 943. Preferably the ear plugs are formed of a soft material for comfort and grip in the ears of the user. For example the ear plugs may be formed of a silicone or other suitable plastics material or a foam material. In an alternative embodiment the arms 940 comprises first and second portions 942, 943 may be without ear plugs 941 to be received above and rest on top of the user's ears.

The cannula body 935 and frame 950 are generally curved to match the shape of a human face. A human face is substantially curved when moving from the nose to along the cheeks. The curved shape of the cannula body and the frame follow the general shape of the human face. The curved shape allows for a lower profile on the face and a better fit on the patients face. The cannula of FIGS. 16A to 16E may comprise the geometry features described above with reference to FIGS. 13A and 13B. The cannula body and frame have a curved shape. The cannula body and frame both have a convexly curved front surface (954 and 906 in FIG. 16C). The convex curvature of the front surface of the cannula body and frame is a curvature from top to bottom of the body and frame (e.g. relative to a person wearing the cannula) as shown in the cross section of FIG. 16E.

The cannula of FIGS. 16A to 16E is configured to rest or be positioned horizontal across the patient's face (e.g. with respect to the patient in a standing position). Such an arrangement ensures that when a face mask is applied over the top of the cannula the seal of the face mask is approximately perpendicular to the collapsible portion of the cannula, for a range of mask sizes and including larger masks. Also, the disclosed arrangement is useful in situations where a clinician does not want to lift the patient's head to apply or remove the cannula. The configuration of FIGS. 16A to 16E may be particularly easy to apply when the patient is lying down as no attachment is required behind the patient's ears and so the cannula may be applied straight onto the patient's face with the clinician standing directly over the patient.

Figure 17:
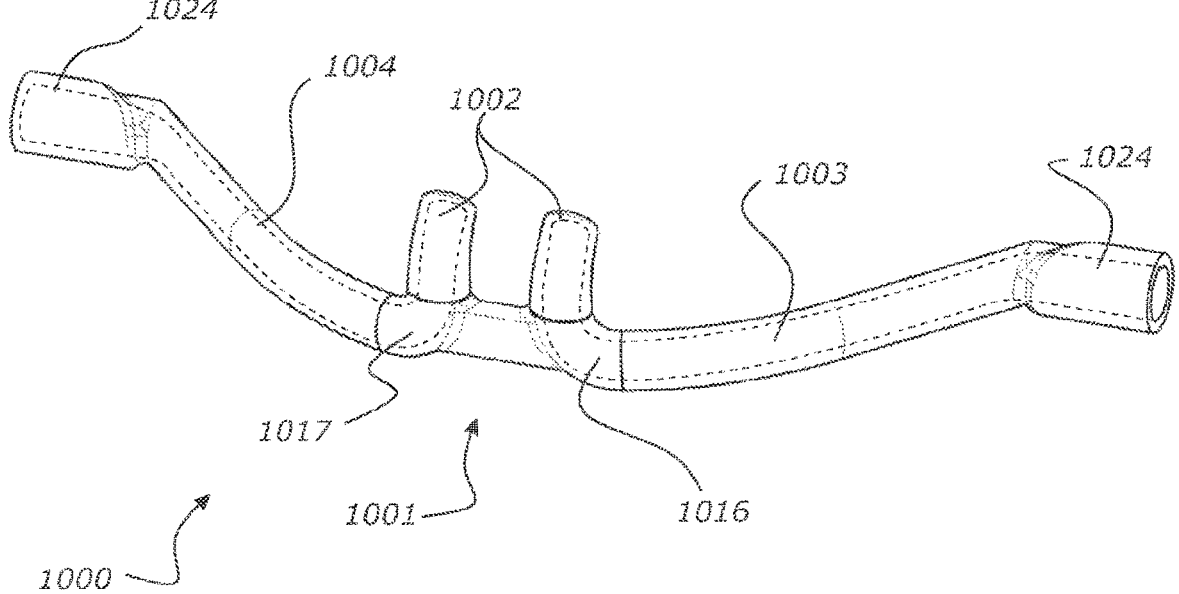
FIG. 17 is a perspective view of a nasal cannula.

FIG. 17 illustrates a further embodiment of a cannula 1000 with inlet sections 1024, also referred to herein as left hand gases inlet 1024, right hand gases inlet 1024, inlet 1024, or right inlets 1024. The cannula comprises a manifold 1001 and a pair of nasal prongs 1002, also referred to herein as outlets 1002, outlet 1002, left hand prong 1002, or right hand prong 1002, or outlets extending from the manifold, and a side member 1003, 1004 extending from each side of the manifold 1001. The term 'manifold', as used in this specification and claims is intended to broadly mean, unless the context suggests otherwise, a member comprising at least two separate lumens, or a member comprising a single lumen with at least two inlets or at least two outlets. In the illustrated embodiment, the manifold 1001 comprises two separate manifold lumens 1016, 1017, each manifold lumen in fluid communication with a respective prong or outlet 1002, such that the prongs or outlets are pneumatically separate. The side members 1003, 1004 each comprise a lumen to provide a conduit for a flow of gases from an inlet 1024 to a corresponding manifold lumen 1016, 1017 and associated nasal prong or outlet 1002. A flow of gases is provided to the cannula via the two inlets 1024. In some embodiments the inlets 1024 may be formed from a rigid material which may provide an improved connection with a gases supply tube or conduit. A rigid element may help to achieve a sealed connection with a connector of a gases supply conduit. The rigid connector may be moulded or overmoulded or co-moulded to the cannula body.

Each side member 1003, 1004 is configured to be collapsible, and is independently collapsible of the other. In normal use, if one member 1003, 1004 was to be collapsed or its lumen inadvertently obstructed, the other side member 1003, 1004 would continue to provide a flow of gases to the user via the associated nasal prong or outlet 1002. In some embodiments, as illustrated, the cannula 1000 is preferably formed in a single integrally formed body of flexible material. In some embodiments, in addition to the single integrally formed cannula body, the cannula may comprise a rigid frame or shield, for example frame 801 as described above with reference to the embodiment of FIG. 15, or frame 950 described with reference to FIGS. 16A to 16E. An interface that delivers flow from two sides may allow the size of the inspiration conduits 112 to be smaller than a single delivery conduit while still being able to deliver the same flow rate. This would be advantageous in reducing the size of the interface on the face and allowing the clinician greater access to the patient's face and airway.

In an alternative embodiment, the manifold includes a gases pathway that allows fluid communication between the lumens of the left and right side members 1003, 1004. The gases pathway in the manifold also allows fluid or gases communication between the lumen of the left side member 1003 and the right hand prong 1002 and the lumen of the right side member 1004 and the left hand prong 1002. In such an alternative embodiment, gases can be received by both prongs from either of the left and right inlets 1024 in case one prong is unexpectedly occluded. Such an arrangement may be advantageous because the inspiratory demand can be met and a sufficient flow rate be provided to an apnoeic patient to ensure there is enough O2 delivered and flushing of CO2 occurs.

In some embodiments the cannula 1000 is formed in a curved configuration to conform to the facial features of a user and may comprise geometry features as described above with reference to FIGS. 13A and 13B. The cannula 1000 may include appropriate headgear connectors, for example as described with reference to FIGS. 11A to 11D. The headgear connectors may be attached to the cannula at a location on the side members or may be connected to the inlet sections 1024. A force from headgear may pull the cannula against the user's face such that flexible body of the cannula deforms to conform to the face of the patient. With the cannula conforming to the patient's face the cannula achieves a low profile on the patient's face.

FIGS. 18A to 18D provide a further example of a nasal cannula 1100, also referred to herein as cannula 1100, comprising a collapsible conduit portion. The cannula comprises a side member 1103, also referred to herein as collapsible conduit portion 1103, conduit member 1103, side 1103, or single side member 1103, that forms or comprises a collapsible conduit portion. The nasal cannula 1100 comprises a manifold portion 1101, also referred to herein as manifold 1101, from which nasal prongs 1102 extend. A side arm or member 1103 extends from one side of the manifold portion 1101. In some embodiments a side member 1103 extends from each side of the manifold portion as described in earlier embodiments. A collapsible conduit portion 1103 may be integrally formed in or with a side member of the cannula. In some embodiments, a side member 1103 is a conduit for transporting a flow of gases from a patient conduit (e.g. conduit 112 in FIG. 1) to the manifold 1101, e.g. the cannula comprises a conduit 1103 extending from at least one side of the manifold 1101. Substantially a full length of the conduit 1103 may be configured to collapse, or a portion of the length of the conduit 1103 may be configured to collapse. In the illustrated embodiment, the cannula 1100 comprises a conduit 1103 with a collapsible portion 1103a and a non-collapsible portion 1103b. The collapsible portion 1103a may be formed from a relatively soft flexible material, such as a silicone material. The non-collapsible portion 1103b may be formed from a relatively hard or rigid material, compared to the material of the collapsible portion. In some embodiments the collapsible portion 1103a is located between the manifold 1101 and the non-collapsible portion 1103b of the conduit. In some embodiments the non-collapsible portion 1103a comprises an inlet 1124 to receive a flow of gases to the cannula 1100.

Figures 18A, 18B, 18C, 18D:
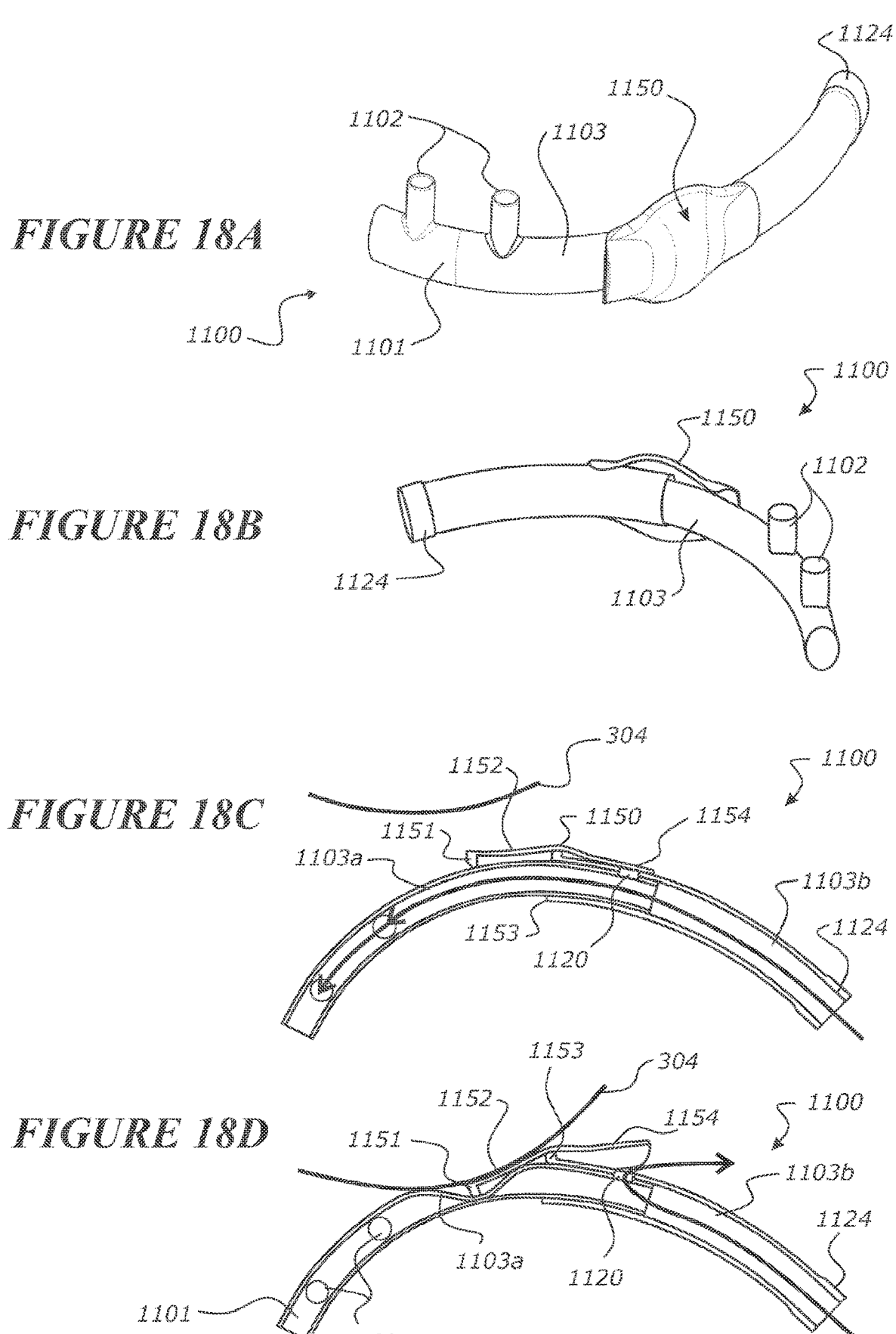
FIGS. 18A to 18D show a nasal cannula.

In some embodiments the cannula 1100 further comprises a mechanism to collapse the collapsible portion of the conduit. In some embodiments the mechanism is a rigid component (rigid relative to the collapsible conduit portion) attached to an outside of the cannula to move from a first configuration in which the collapsible portion is in the open configuration to a second configuration in which the component presses against an outside of the collapsible portion to pinch or flatten the collapsible portion into the closed configuration. In the illustrated embodiment the component is a lever 1150, also referred to herein as manifold portion 1150, that is actuated by an externally applied force, for example a force provided by the seal 304 of a face mask pressing against the lever 1150 as the face mask 300 is applied to a user's face over the top of the cannula 1100. In some embodiments the lever 1150 is pivotally supported by or attached to the non-collapsible portion 1103b of the conduit 1103. In use a user may press the lever (e.g. by pressing a face mask seal against the lever) to pivot the lever 1150 to press the lever against the collapsible portion 1103a to collapse the collapsible portion 1103a and occlude or partially occlude the lumen of the collapsible portion 1103a. The lever 1150 is pivotable between a first configuration as shown in FIG. 18C in which the collapsible portion is open, and a second configuration as shown in FIG. 18D in which the collapsible portion is closed. In the second configuration the lever presses against an outside of the collapsible portion 1103a of the conduit to pinch or flatten the conduit. In some embodiments, the lever may be pivotally attached to the manifold portion 1101, should the manifold have sufficient rigidity to pivotally support the lever to pivot between the first and second configurations. When a force is removed from the lever 1150, gases flow through the collapsible portion and force the lever to return to the first configuration. The lever may comprise a projection such as a rim 1151 that contacts and pinches the conduit in the closed configuration. The projection or rim 1151 is preferably wider than the collapsible portion so that the rim applies across the full width of the conduit.

In some embodiments, the lever 1150 comprises a first arm 1152 extending from a first side of a pivot 1153 and a second arm 1154 extending from an opposite second side of the pivot 1153. When in the first configuration (FIG. 18C) the lever 1150 is pivoted about the pivot 1153 so that the first arm does not pinch or flatten the conduit and the second arm 1154 covers or closes or obscures a vent aperture 1120 in the conduit 1103. In the second configuration (FIG. 18D) the lever 1150 is pivoted so that the first arm 1152 pinches or flattens the conduit 1103 and the second arm 1154 lifts away from the vent aperture 1120 to allow gases in the conduit upstream of the collapsible portion 1103a to vent to atmosphere. In such an embodiment the lever 1150 operates in a seesaw fashion to, in the first configuration, occlude the collapsible portion 1103a and vent the conduit upstream, and in the second configuration, to allow the collapsible portion 1103b to open and close the vent aperture 1120.

In some embodiments the cannula 1100 is formed in a curved configuration to conform to the facial features of a user. The cannula 1100 is illustrated with a single side member 1103 however in some embodiments may comprise a left hand side member and a right hand side member as described in earlier embodiments, and may comprise geometry features as described above with reference to FIGS. 13A and 13B. Further, the cannula 1100 may include appropriate headgear connectors, for example as described with reference to FIGS. 11A to 11D. The headgear connectors may be attached to the cannula at a location on the side members. A force from headgear may pull the cannula against the user's face such that flexible body of the cannula deforms to conform to the face of the patient. With the cannula conforming to the patient's face the cannula achieves a low profile on the patient's face.

In some embodiments, a conduit, e.g. inspiratory conduit 112 may comprise a collapsible portion and a lever 1150 as described above.

In some embodiments, the patient interface or a conduit may comprise a collapsible portion and a rigid shield or member attached to the outside of the collapsible portion. The member is rigid relative to the conduit portion and therefore is adapted to distribute an external force applied to the member over a predetermined collapsible area of the collapsible portion. The rigid member assists to ensure the collapsible portion is pinched off adequately to substantially occlude the conduit and avoid creasing or folding of the conduit that might otherwise provide a leak path through the collapsed portion of the conduit.

Aspects of the present invention are described above with reference to nasal cannulas. However, aspects of the present invention may be applied in other interfaces, such as for example an oral interface. An example oral interface 1200 is illustrated in FIG. 19, general features of which are described in U.S. Pat. No. 9,155,855. The interface 1200 comprises a vestibular shield 1221, an outer flap 1225, and a connector 1235 that connects the outer flap to the vestibular shield. In use the vestibular shield 1221 is received in the user's mouth and sits inside the user's lips, and the outer flap 1225 sits outside the user's mouth about the outside of the user's lips. A seal is formed by pressure caused by the outer flap 1225 on the outside of the user's lips and an opposing force of the vestibular shield 1221 on the inside of the user's lips. The interface 1200 provides a flow of gases to the user through the connector and via outlets 1223, 1224 from the connector. The outlets 1223, 1224 may be received in outlets 1232, 1233 of the shield 1221. In the illustrated embodiment a manifold 1201 is provided to attach to the connector. A side member or conduit comprising a lumen extends from each side of the manifold, a left side member 1203 and a right side member 1204 (with respect to a user). An inspiratory conduit (e.g. conduit 112) is connected in use to at least one of the side members 1203, 1204 to provide a flow of gases via the side member or members and the manifold 1201 to the connector 1235 via an inlet 1234 of the connector and to the user's airway via the connector outlets 1223, 1224. In some embodiments the interface may comprises a body comprising the manifold 1201 and outlet 1202 from the manifold (e.g. to be connected with connector inlet 1234) and the side members 1203, 1204. In some embodiments, the body may also be integrally formed with the outer flap 1225 or connector 1235 or both. In some embodiments, the outer flap 1225, connector 1235 and shield 1221 may be integrally formed, and may be integrally formed together with the manifold 1201 and side members 1203, 1204. In some embodiments, an oral interface may be without a manifold and may comprise an elbow connector to configure the interface as a single inspiratory conduit embodiment. The side members 1203, 1204 each comprise a collapsible conduit portion, as described previously with reference to cannula embodiments. In some embodiments the side members 1203, 1204 wrap around and/or are closely adjacent to the outer flap 1225. In some embodiments, the side members or conduits are integrally formed with the outer flap and/or may be positioned between a patient face side of the outer flap that contacts a user's face or lips and an outer (opposite) side of the outer flap. The oral interface 1200 may further comprise any one or more features of cannula embodiments described above in relation to collapsible conduit portions and/or configurability, e.g. as a dual or single inlet interface.

Where, in the foregoing description reference has been made to integers or components having known equivalents thereof, those integers are herein incorporated as if individually set forth.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

The invention claimed is:

1. A nasal cannula comprising:
   a manifold comprising at least one nasal prong or outlet extending from the manifold, wherein the at least one nasal prong or outlet is, during use, received by a user's nare;
   a first side member extending from a first side of the manifold;
   a second side member extending from a second side of the manifold; and
   wherein, in a planar view, the first side member and the second side member form an obtuse angle when the nasal cannula is in a neutral or unbent configuration;
   wherein the nasal cannula comprises a wall near to and on an inlet side of the at least one nasal prong or outlet, wherein the wall is configured to separate a lumen of the first side member from the manifold and the second side member such that only the first side member acts as a conduit to provide a flow of gases from an inlet of the nasal cannula to the manifold; and
   wherein a collapsible conduit portion is integrally formed in or with the first side member of the nasal cannula, wherein the collapsible conduit portion is configured to transition between an open configuration wherein the conduit provides the flow of gases from the inlet to the manifold, and a collapsed configuration wherein flow of gases is from the inlet to the manifold is reduced or stopped.

2. The nasal cannula of claim 1, wherein the obtuse angle is between 100 to 130 degrees, between 100 to 120 degrees, between 100 to 110 degrees, or between 105 to 106 degrees.

3. The nasal cannula of claim 1, wherein the first side member and the second side member are straight in an unbent configuration, and the manifold is curved to provide the obtuse angle between the first side member and the second side member.

4. The nasal cannula of claim 1, wherein the nasal cannula further comprises a first headgear connector part and a second headgear connector part, wherein the first headgear connector part and the second headgear connector part are configured to attach a headgear to the nasal cannula.

5. The nasal cannula of claim 4, wherein a distance between a distal end of the first side member and the second side member, or a distance between the first headgear connector part and the second headgear connector part is between 100 mm to 150 mm, between 110 mm to 140 mm, between 110 mm to 130 mm, or 120 mm.

6. The nasal cannula of claim 4, wherein the first headgear connector part is arranged at a first angle to the first side member, in a planar view of the nasal cannula, between 130 degrees and 170 degrees, 140 degrees and 160 degrees, or 145 degrees and 155 degrees; and/or wherein the second headgear connector part is arranged at a second angle to the second side member, in a planar view of the nasal cannula, between 130 degrees and 170 degrees, 140 degrees and 160 degrees, or 145 degrees and 155 degrees.

7. The nasal cannula of claim 4, wherein the first headgear connector part is arranged at a first angle to the first side member in a side view of the nasal cannula so that in use the nasal cannula is positioned horizontally on a user's face and with the headgear extending above a user's ears; and/or wherein the second headgear connector part is arranged at a second angle to the second side member in a side view of the nasal cannula so that in use the nasal cannula is positioned horizontally on the user's face and with the headgear extending above the user's ears.

8. The nasal cannula of claim 7, wherein the first angle and/or the second angle is between 10 degrees to 30 degrees, between 15 degrees to 25 degrees, or 20 degrees.

9. The nasal cannula of claim 1, wherein either the first side member or the second side member is a conduit for transporting a flow of gases from a patient conduit to the manifold.

10. The nasal cannula of claim 9 further comprising a plug or a conduit connector, wherein the plug or the conduit connector is adapted to fit to an end of at least one of the first side member or second side member.

11. The nasal cannula of claim 10, wherein the first side member and the second side member are soft or compliant relative to the plug or the conduit connector.

12. The nasal cannula of claim 1, wherein a lateral cross section of the collapsible conduit portion comprises:

a first side for positioning against a user's face;

a second side opposite the first side and facing away from the user's face;

wherein the first side and the second side are joined by first and second fold points; and wherein a thickness of the first and second fold points is less than a thickness of a remainder of the lateral cross section of the collapsible conduit portion.

13. The nasal cannula of claim 1, wherein the wall is curved to assist with directing the flow of gases from the conduit into the at least one nasal prong or outlet.

14. The nasal cannula of claim 1, wherein the wall acts as a rib to help keep a gas path open near the at least one nasal prong or outlet and prevent kinking of the nasal cannula.

15. The nasal cannula of claim 1, wherein the nasal cannula is a single inlet cannula.

16. The nasal cannula of claim 1, wherein the first side member, the second side member, and the manifold are a unitary integrally formed member or wherein the first side member, the second side member, the manifold, and the at least one nasal prong or outlet are a unitary integrally formed member.

17. The nasal cannula of claim 1, wherein the nasal cannula comprises a cannula body formed of a flexible material, and the cannula body comprising the manifold, the at least one nasal prong or outlet, the first side member, and the second side member.

18. The nasal cannula of claim 1, wherein, when in use, the nasal cannula:

conforms to a user's face, achieves a low profile on the user's face, contours around the user's face without any of the manifold, the first side member, or the second side member kinking, or is non-sealing.

* * * * *